(12) United States Patent
Murphy et al.

(10) Patent No.: US 7,160,868 B2
(45) Date of Patent: Jan. 9, 2007

(54) NR-CAM GENE, NUCLEIC ACIDS AND NUCLEIC ACID PRODUCTS FOR THERAPEUTIC AND DIAGNOSTIC USES FOR TUMORS

(75) Inventors: Gerald P. Murphy, Seattle, WA (US); Alton L. Boynton, Redmond, WA (US); Anil Sehgal, Seattle, WA (US)

(73) Assignee: Northwest Hospital

( * ) Notice: Subject to any disclaimer, the term of this patent is extended or adjusted under 35 U.S.C. 154(b) by 0 days.

(21) Appl. No.: 09/301,380

(22) Filed: Apr. 27, 1999

(65) Prior Publication Data

US 2004/0224909 A1    Nov. 11, 2004

Related U.S. Application Data

(60) Provisional application No. 60/112,098, filed on Dec. 14, 1998, provisional application No. 60/083,152, filed on Apr. 27, 1998.

(51) Int. Cl.
    *A61K 31/70* (2006.01)
    *C07H 21/04* (2006.01)

(52) U.S. Cl. ........................................ 514/44; 536/24.5

(58) Field of Classification Search ............... 514/44; 536/23.1, 24.5; 435/6, 91.1, 91.31, 395, 435/366, 325

See application file for complete search history.

(56) References Cited

OTHER PUBLICATIONS

Lisa M. Moscoso et al., Expression of Four Immunoglobulin Superfamily Adhesion Molecules (L1, Nr-CAM/Bravo, Neurofascin/ABGP, and N-CAM) in the Developing Mouse Spinal Cord, The Journal of Comparative Neurology, 352, pp. 321-334.*
W. Michael Flanagan et al., Cellular penetration and antisense activity by a phenoxazine-substituted heptanucleotide, RESEARCH, pp. 1-5.*
Andrea D. Branch, A good antisense molecule is hard to find, TIBS 23—Feb. 1998, pp. 45-50.*
PE Blackshear, Toxicologic Pathology, "Genetically Engineered Rodent Models of Mammary Gland Carcinogenesis: An Overview," 2001, vol. 29, No. 1, pp. 105-116.*
K-Y Jen et al., Stem Cells, "Suppression of Gene Expression by Targeted Disruption of Messenger RNA: Available Options and Current Strategies," 2000, 18: 307-319.*
L Resor et al., Human Molecular Genetics, "Unraveling human cancer in the mouse: recent refinements to modeling and analysis," 2001, vol. 10, No. 7, pp. 669-675.*
TV Chirila et al., Biomaterials,"The use of synthetic polymers for delivery of therapeutic antisense oligodeoxynucleotides,"2002, 23: pp. 321-342.*
H Fritz et al., Journal of Colloid and Interface Science,"Cationic Polystyrene Nanoparticles: Preparation and Characterization of a Model Drug Carrier System for Antisense Oligonucleotides,"1997, pp. 272-288.*
CF Bennett et al., Methods in Molecular Medicine:Antisense Therapeutics,"Pharmacology of Antisense Therapeutic Agents," 1996, Chap. 2, pp. 13-46.*
DDF Ma et al., Biotechnology Annual Review, "Synthetic oligonucleotides as therapeutics:the coming of age," Jul. 2000, vol. 5, pp. 155-196.*
S Agrawal et al., Molecular Medicine Today,"Antisense therapeutics: is it as simple as complementary base recognition?"Feb. 2000, vol. 6, pp. 72-81.*
DW Green et al., American College of Surgeons,"Antisense Oligoncleotides: An Evolving Technology for the Modulation of Gene Expression in Human Disease,"Jul. 2000, vol. 191, No. 1, pp. 93-105.*
Sehgal et al., International Journal of Cancer, vol. 76, pp. 451-458, 1998.*
Lane et al. Genomics, vol. 35, pp. 456-465, 1996.*
Schwab, G. et al., An Approach for New Anticancer Drugs: Oncogene-Targeted Antisense DNA, *Annals of Oncology* 5:55-58, 1994.
Matveeva, O. et al., A Rapid *In Vitro* Method For Obtaining RNA Accessibility Patterns For Complementary DNA Probes: Correlation With An Intracellular Pattern and Known RNA Structures, *Nucleic Acids Res.* 25:5010-6, 1997.
Flanagan, Michael W., Antisense Comes of Age, *Cancer and Metastasis Reviews* 17:169-176, 1998.
Ho, Siew Peng et al., Antisense Oligonucleotides for Target Validation in the CNS, *Current Opinion in Molecular Therapuetics* 1:336-343, 1999.
Holmlund, Jon T et al., Toward Antisense Oligonucleotide Therapy for Cancer: ISIS Compounds in Clinical Development, *Current Opinion in Molecular Therapeutics* 1:372-385, 1999.

* cited by examiner

*Primary Examiner*—James Schultz
*Assistant Examiner*—Jon B. Ashen
(74) *Attorney, Agent, or Firm*—Townsend and Townsend and Crew LLP

(57) ABSTRACT

The present invention relates to the identification of a novel role of Nr-CAM in cell transformation and aberrant cellular proliferation. In particular, the present invention relates to the altered gene expression of Nr-CAM in a number of primary tumors and cell lines derived from tumors, in addition to, the altered gene expression of ligands for Nr-CAM. Further, the present invention relates, in part, to the Applicants' surprising discovery that the inhibition of Nr-CAM gene expression or the inhibition of Nr-CAM activity in transformed cells reverses the transformed phenotype.

8 Claims, 36 Drawing Sheets

Figure 3A:

T N T N
C →
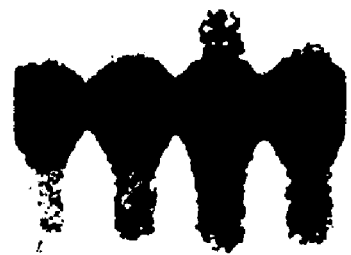
D4-1 →
FIG. 1

```
   1 cttcaaagtt ccccgcatga aaattactta aacgttgcac acaacgtttc agaaaatctt
  61 ttgtgaaaga agaaaaggaa attcagtgtg tgagtctcag caggagttaa gctaatgcag
 121 cttaaaataa tgccgaaaaa gaagcgctta tctgcgggca gagtgcccct gattctcttc
 181 ctgtgccaga tgattagtgc actggaagta cctcttgatc caaaacttct tgaagacttg
 241 gtacagcctc caaccatcac ccaacagtct ccaaaagatt acattattga ccctcgggag
 301 aatattgtaa tccagtgtga agccaaaggg aaaccgcccc caagctttc ctggacccgt
 361 aatgggactc atttttgacat cgataaagac cctctggtca ccatgaagcc tggcacagga
 421 acgctcataa ttaacatcat gagcgaaggg aaagctgaga cctatgaagg agtctatcag
 481 tgtacagcaa ggaacgaacg cggagctgca gtttctaata acattgttgt ccgcccatcc
 541 agatcaccat tgtggaccaa agaaaaactt gaaccaatca cacttcaaag tggtcagtct
 601 ttagtacttc cctgcagacc cccaattgga ttaccaccac ctataatatt ttggatggat
 661 aattccttc aaagacttcc acaaagtgag agagtttctc aaggttgaa tggggacctt
 721 tatttttcca atgtcctccc agaggacacc cgcgaagact atatctgtta tgctagattt
 781 aatcatactc aaaccataca gcagaagcaa cctatttctg tgaaggtgat ttcagtggat
 841 gaattgaatg acactatagc tgctaatttg agtgacactg agtttatgg tgctaaatca
 901 agtagagaga ggccaccaac atttttaact ccagaaggca atgcaagtaa caaagaggaa
 961 ttaagaggaa atgtgctttc actggagtgc attgcagaag gactgcctac cccaattatt
1021 tactgggcaa aggaagatgg aatgctaccc aaaaacagga cagtttataa gaactttgag
1081 aaaacctgc agatcattca tgtttcagaa gcagactctg gaaattacca atgtatagca
1141 aaaaatgcat taggagccat ccaccatacc atttctgtta gagttaaagc ggctccatac
1201 tggatcacag cccctcaaaa tcttgtgctg tccccaggag aggatgggac cttgatctgc
1261 agagctaatg gcaaccccaa acccagaatt agctggttaa caaatggagt cccaatagaa
1321 attgcccctg atgaccccag cagaaaaata gatggcgata ccattatttt ttcaaatgtt
1381 caagaaagat caagtgcagt atatcagtgc aatgcctcta atgaatatgg atatttactg
1441 gcaaacgcat ttgtaaatgt gctggctgag ccaccacgaa tcctcacacc tgcaaacaca
1501 ctctaccagg tcattgcaaa caggcctgct ttactagact gtgccttctt tgggtctcct
1561 ctcccaaccc tcgagtggtt taaaggagct aaaggaagtg ctcttcatga agatatttat
1621 gttttacatg aaaatggaac tttggaaatc aaagatgcta catggatcgt taaagaaatt
1681 cctgtggccc aaaaggacag tacaggaact tatcgtgtg ttgcaaggaa taattaggg
1741 atggcaaaga atgaagttca cttacagccc gaatatgcag ttgtgcaaag agggagcatg
1801 gtgtcctttg aatgcaaagt gaaacatgat cacaccttat ccctcactgt cctgtggctg
1861 aaggacaaca gggaactgcc cagtgatgaa aggttcactg ttgacaagga tcatctagtg
1921 gtagctgatg tcagtgacga tgacagcggg acctacacgt gtgtggccaa caccactctg
1981 gacagcgtct ccgccagcgc tgtgcttagc gttgttgctc ctactccaac tccagctccc
2041 gttacgatg tcccaaatcc tccctttgac ttagaactga cagatcaact tgacaaaagt
2101 gttcagctgt catggaccc aggcgatgac aacaatagcc cattacaaa attactcatc
2161 gaatatgaag atgcaatgca caagccaggg ctgtggcacc accaaactga agtttctgga
2221 acacagacca cagcccagct gaagctgtct ccttacgtga actactcctt ccgcgtgatg
2281 gcagtgaaca gcattggga gagcttgccc agcgaggcgt ctgagcagta tttgacgaaa
2341 gcctcagaac cagataaaaa ccccacagct gtggaaggac tgggatcaga gcctgataat
2401 ttggagatta cgtggaagcc cttgaatggt ttcgaatcta atgggccagg ccttcagtac
2461 aaagttagct ggcgccagaa agatggtgat gatgaatgga catctgtggt tgtggcaaat
```
FIG.2A

```
2521 gtatccaaat atattgtctc aggcacgcca acctttgttc catacctgat caaagttcag
2581 gccctgaatg acatggggtt tgcccccgag ccagctgtag tcatgggaca ttctggagaa
2641 gacctcccaa tggtggctcc tgggaacgtg cgtgtgaatg tggtgaacag taccttagcc
2701 gaggtgcact gggacccagt acctctgaaa agcatccgag gacacctaca aggctatcgg
2761 atttactatt ggaagaccca gagttcatct aaaagaaaca gacgtcacat tgagaaaaag
2821 atcctcacct tccaaggcag caagactcat ggcatgttgc cggggctaga gccctttagc
2881 cactacacac tgaatgtccg agtggtcaat gggaaagggg agggcccagc cagccctgac
2941 agagtcttta atactccaga aggagtcccc agtgctccct cgtctttgaa gattgtgaat
3001 ccaacactgg actctctcac tttggaatgg gatccaccga gccacccgaa tggcattttg
3061 acagagtaca ccttaaagta tcagccaatt aacagcacac atgaattagg ccctctggta
3121 gatttgaaaa ttcctgccaa caagacacgg tggactttaa aaaatttaaa tttcagcact
3181 cgatataagt tttatttcta tgcacaaaca tcagcaggat caggaagtca aattacagag
3241 gaagcagtaa caactgtgga tgaagctggt attcttccac ctgatgtagg tgcaggcaaa
3301 gttcaagctg taaataccag gatcagcaat cttactgctg cagctgctga gacctatgcc
3361 aatatcagtt gggaatatga gggaccagag catgtgaact tttatgttga atatggtgta
3421 gcaggcagca aagaagaatg gagaaaagaa attgtaaatg gttctcggag cttctttggg
3481 ttaaagggtc taatgccagg aacagcatac aaagttcgag ttggtgctgt ggggactct
3541 ggttttgtga gttcagagga tgtgtttgag acaggcccag cgatggcaag ccggcaggtg
3601 gatattgcaa ctcagggctg gttcattggt ctgatgtgtg ctgttgctct ccttatctta
3661 attttgctga ttgtttgctt catcagaaga aacaagggtg gtaaatatcc agttaaagaa
3721 aaggaagatg [cccatgctga ccctgaaatc cagcctatga aggaagatga tgggacattt
3781 ggagaataca gtgatgcaga agaccacaag cctttgaaaa aaggaagtcg aactccttca
3841 gacaggactg tgaaaaaaga agatagtgac gacagcctag ttgactatgg agaaggggtt
3901 aatggccagt tcaatgagga tggctccttt attggacaat acagtggtaa gaaagagaaa
3961 gagccggctg aaggaaacga aagctcagag gcaccttctc ctgtcaacgc catgaattcc
4021 tttgtttaat ttttaagctc aaagccaata ttccatttct ctagaatgtt tatcctaagc
4081 tcttgtttgt cagccctctc atactatgaa catgtgggta gagagtatat tttc
```

FIG. 2A (CONT')

"MPKKKRLSAGRVPLILFLCQMISALEVPLDPKLLEDLVQPPTIT
QQSPKDYIIDPRENIVIQCEAKGKPPPSFSWTRNGTHFDIDKDPLVTMKPGTGTLIIN
IMSEGKAETYEGVYQCTARNERGAAVSNNIVVRPSRSPLWTKEKLEPITLQSGQSLVL
PCRPPIGLPPPIIFWMDNSFQRLPQSERVSQGLNGDLYFSNVLPEDTREDYICYARFN
HTQTIQQKQPISVKVISVDELNDTIAANLSDTEFYGAKSSRERPPTFLTPEGNASNKE
ELRGNVLSLECIAEGLPTPIIYWAKEDGMLPKNRTVYKNFEKTLQIIHVSEADSGNYQ
CIAKNALGAIHHTISVRVKAAPYWITAPQNLVLSPGEDGTLICRANGNPKPRISWLTN
GVPIEIAPDDPSRKIDGDTIIFSNVQERSSAVYQCNASNEYGYLLANAFVNVLAEPPR
ILTPANTLYQVIANRPALLDCAFFGSPLPTIEWFKGAKGSALHEDIYVLHENGTLEIK
DATWIVKEIPVAQKDSTGTYTCVARNKLGMAKNEVHLQPEYAVVQRGSMVSFECKVKH
DHTLSLTVLWLKDNRELPSDERFTVDKDHLVVADVSDDDSGTYTCVANTTLDSVSASA
VLSVVAPTPTPAPVYDVPNPPFDLELTDQLDKSVQLSWTPGDDNNSPITKFIIEYEDA
MHKPGLWHHQTEVSGTQTTAQLKLSPYVNYSFRVMAVNSIGKSLPSEASEQYLTKASE
PDKNPTAVEGLGSEPDNLEITWKPLNGFESNGPGLQYKVSWRQKDGDDEWTSVVVANV
SKYIVSGTPTFVPYLIKVQALNDMGFAPEPAVVMGHSGEDLPMVAPGNVRVNVVNSTL
AEVHWDPVPLKSIRGHLQGYRIYYWKTQSSSKRNRRHIEKKILTFQGSKTHGMLPGLE
PFSHYTLNVRVVNGKGEGPASPDRVFNTPEGVPSAPSSLKIVNPTLDSLTLEWDPPSH
PNGILTEYTLKYQPINSTHELGPLVDLKIPANKTRWTLKNLNFSTRYKFYFYAQTSAG
SGSQITEEAVTTVDEAGILPPDVGAGKVQAVNTRISNLTAAAAETYANISWEYEGPEH
VNFYVEYGVAGSKEEWRKEIVNGSRSFFGLKGLMPGTAYKVRVGAVGDSGFVSSEDVF
ETGPAMASRQVDIATQGWFIGLMCAVALLILILLIVCFIRRNKGGKYPVKEKEDAHAD
PEIQPMKEDDGTFGEYSDAEDHKPLKKGSRTPSDRTVKKEDSDDSLVDYGEGVNGQFN
EDGSFIGQYSGKKEKEPAEGNESSEAPSPVNAMNSFV"

FIG. 2B

FIG. 2C

```
HUMAN Nr-CAM   4097    TCTCATACTATGAACATATGGGTAGAGAGTATATTTTC              4134
                       **************************************
D4-1           1       TCTCATACTATGAACATATGGGTAGAGAGTATATTTTCTGCTGT        44
                       ************ ************* **  ** *******  **
RAT Nr-CAM     3713    TCTCATACTATGGACATATGGGTAGAAAGAATGTTTTCTGCGGT        3757

D4-1           45      ATGTTAGTATTATGAGAATAGTTACAGCAAAAACATAACTCAGT        88
                       ** * ******** ****  **       **  * *  * * *****
RAT Nr-CAM     3758    ATATGAGTATTATAAGAACAGAGCAAGAACATAACTCAGTCAGT        3801

D4-1           89      CAAAGTATATGTTAATATGAACTGGAATGCAAAAGTGCATACTT        132
                       ** *  ***  *************** **  ***  *
RAT Nr-CAM     3802    CAGATGATACGTTAATATGAACTGGGGTGAAAAGG                 3836

D4-1           133     TTTCATTCAAAATGGGTATTCTTGATTTCCTAAAAAAAAAAAAA        176
```

FIG. 2D

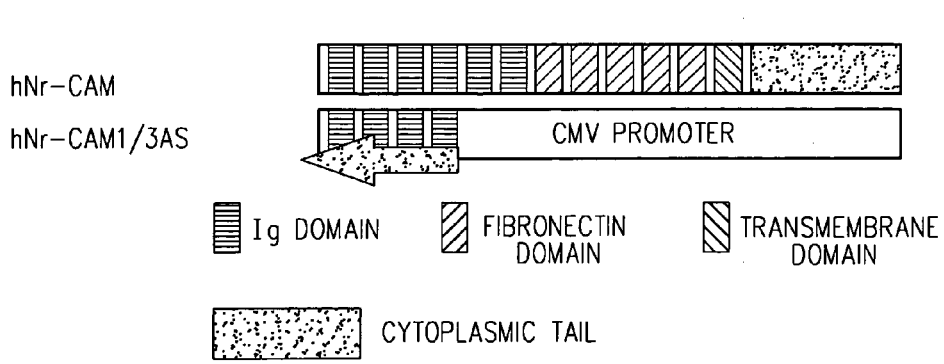

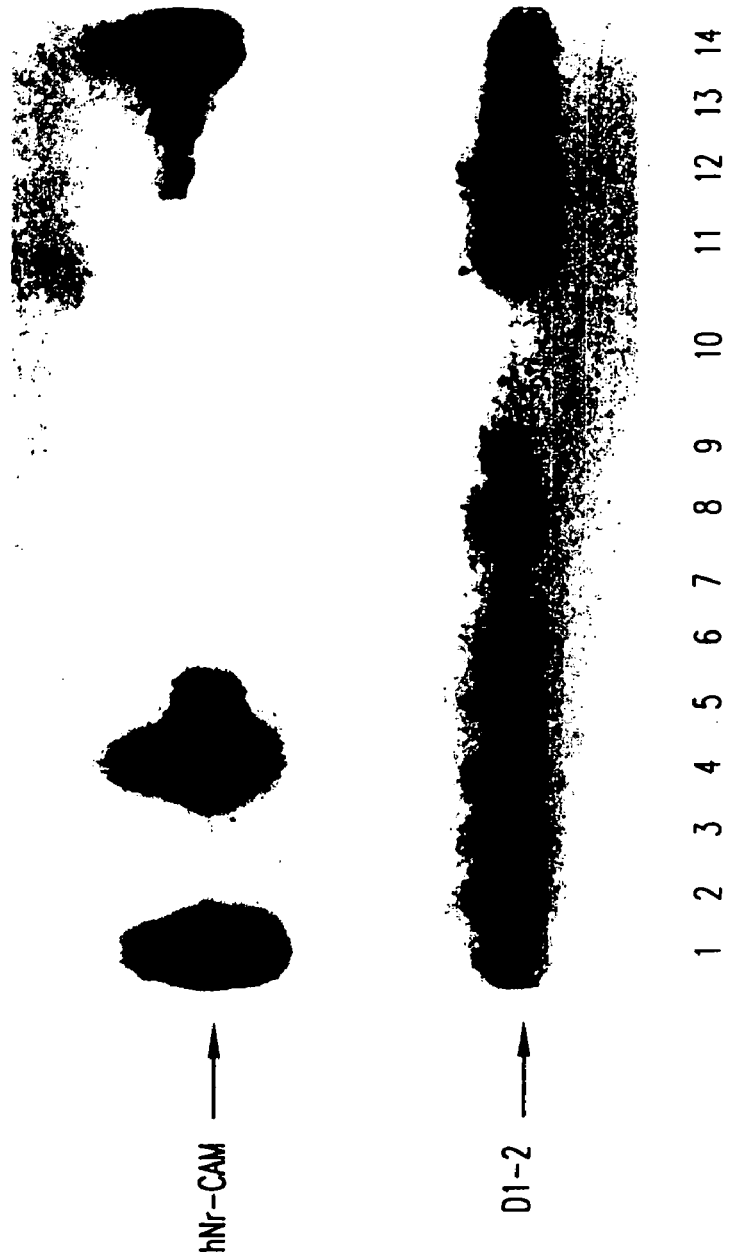

a　b
hNr-CAM　→　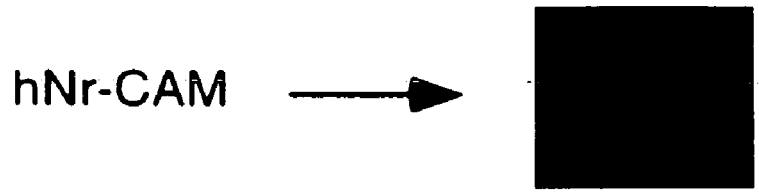
EGFR　→　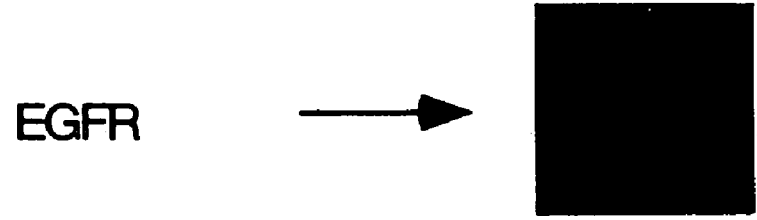
D1-2　→　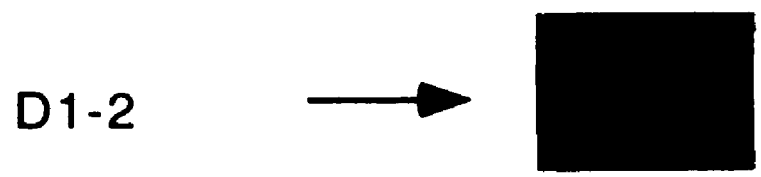
FIG.5A

← hNr-CAM
1  2  3  4
FIG.9

FIG.16A  FIG.16B
 
 
FIG.16C  FIG.16D

FIG.20A
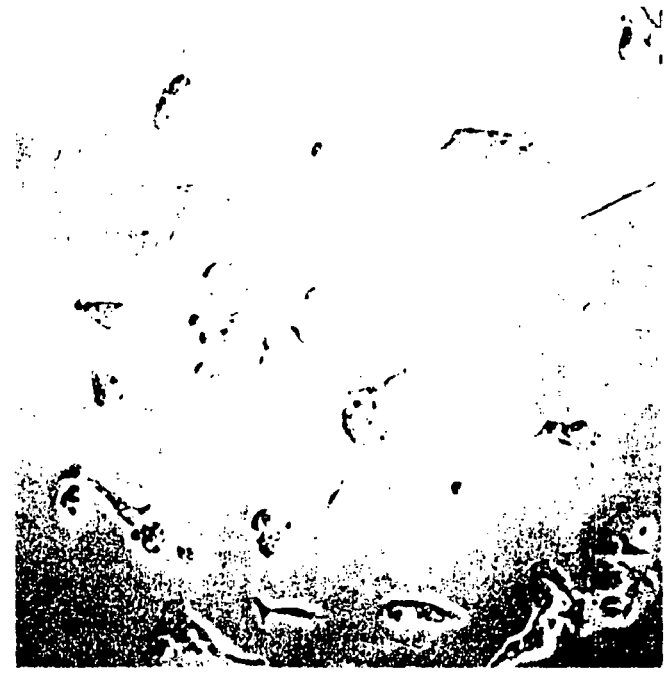
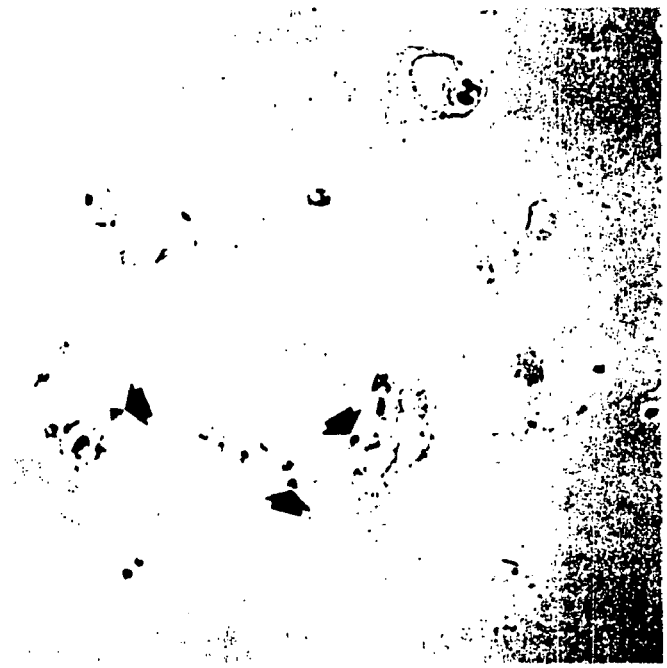
FIG.20B

```
Human Nr-CAM:   1 ATGCCGAAAAAGAAGCGCTTATCTGCGGGCAGAGTGCCCCTGATTCTCTTCCTGTGCCAG  60
                  ||||||||  ||||||| |||  |||||  |||||||  |||||||| ||||||||||||
Rat Nr-CAM:    19 ATGCCGAAGAAGAAGCCCTTGTCTGCAGGCAGAGCGCCCCTGTTTCTCTTCCTGTGCCAG  78

Human Nr-CAM:  61 ATGATTAGTGCACTGGAAGTACCTCTTGATCCAAAACTTCTTGAAGACTTGGTACAGCCT 120
                  |||||  ||  ||||| ||  ||||||||||||| || ||||| ||||||||||||||||
Rat Nr-CAM:    79 ATGATCAGCGCTCTGGATGTTCCTCTTGATCCAAAGCTCCTTGATGACTTGGTACAGCCT 138

Human Nr-CAM: 121 CCAACCATCACCCAACAGTCTCCAAAAGATTACATTATTGACCCTCGGGAGAATATTGTA 180
                  |||||  ||||| |||||||| ||||| | |||||||||||||| ||||||||||||||
Rat Nr-CAM:   139 CCAACTATCACTCAACAGTCACCAAAAGACTACATCATTGACCCACGGGAGAATATTGTA 198

Human Nr-CAM: 181 ATCCAGTGTGAAGCCAAAGGGAAACCGCCCCCAAGCTTTTCCTGGACCCGTAATGGGACT 240
                  |||||  |||||  |||||||||||| || || ||||||||||||||| || ||  || 
Rat Nr-CAM:   199 ATCCAATGTGAGGCCAAAGGGAAACCTCCTCCAAGCTTTTCCTGGACTCGTAACGGAACA 258

Human Nr-CAM: 241 CATTTTGACATCGATAAAGACCCTCTGGTCACCATGAAGCCTGGCACAGGAACGCTCATA 300
                  |||||||||| | || |||||||||||||||| ||||||||||| ||||| ||||| | |
Rat Nr-CAM:   259 CATTTTGACATAGACAAAGACCCTCTGGTCACTATGAAGCCTGGCTCAGGAACCCTTGTC 318

Human Nr-CAM: 301 ATTAACATCATGAGCGAAGGGAAAGCTGAGACCTATGAAGGAGTCTATCAGTGTACAGCA 360
                  || ||||||||| ||||| |||| |||||||||||||||| ||  || ||| |||| ||
Rat Nr-CAM:   319 ATCAACATCATGAGTGAAGGAAAGGCGGAGACCTATGAAGGGGTTTACCAGTGCACTGCA 378

Human Nr-CAM: 361 AGGAACGAACGCGGAGCTGCAGTTTCTAATAACATTGTTGTCCGCCCATCCAGATCACCA 420
                  ||||| ||  |||||||||| || || ||||||||||||||||||||  |  || ||||
Rat Nr-CAM:   379 AGGAATGAGCGCGGAGCTGCTGTCTCCAATAACATTGTTGTCCGCCCCTCTAGGTCACCC 438

Human Nr-CAM: 421 TTGTGGACCAAAGAAAAACTTGAACCAATCACACTTCAAAGTGGTCAGTCTTTAGTACTT 480
                  ||||||||||| ||||| ||||||||||| || | | |||||||||||||| |||||||
Rat Nr-CAM:   439 TTGTGGACCAAGGAAAGACTTGAACCAATAATCCTCCGAAGTGGTCAGTCACTAGTACTT 498

Human Nr-CAM: 481 CCCTGCAGACCCCCAATTGGATTACCACCACCTATAATATTTTGGATGGATAATTCCTTT 540
                  || || || || |||||||||||||||||| |||||||||||||||||||||| ||||||
Rat Nr-CAM:   499 CCATGTAGGCCTCCAATTGGATTACCACCGGCCATAATATTTTGGATGGATAACTCCTTT 558

Human Nr-CAM: 541 CAAAGACTTCCACAAAGTGAGAGAGTTTCTCAAGGTTTGAATGGGGACCTTTATTTTTCC 600
                  |||||||| ||||| ||||| |  |||||||||| || ||||||||||||| || |||
Rat Nr-CAM:   559 CAAAGACTGCCACAGAGTGAGCGGGTTTCCCAAGGACTGAATGGAGACCTTTACTTCTCC 618

Human Nr-CAM: 601 AATGTCCTCCCAGAGGACACCCGCGAAGACTATATCTGTTATGCTAGATTTAATCATACT 660
                  |||||||||||||||||||||||||| ||||| ||||| ||||| |||||||||||| |||
Rat Nr-CAM:   619 AATGTCCTCCCAGAGGACACCCGCGAAGACTATATCTGTTATGCTAGATTTAATCATACT 678

Human Nr-CAM: 661 CAAACCATACAGCAGAAGCAACCTATTTCTGTGAAGGTGATTTCAGTGGATGAATTGAAT 720
                  ||||| || || ||||| ||||||||||||||||||||||||||||||||||||||||||
Rat Nr-CAM:   679 CAAACAATTCAACAGAAACAACCTATTTCTCTGAAGGTGATTTCAGTGGATGAATTGAAT 738
```

FIG.24A

```
Human Nr-CAM:  721 GACACTATAGCTGCTAATTTGAGTGACACTGAGTTTTATGGTGCTAAATCAAGTAGAGAG 780
                   ||||||||||||||||||||||||||||||||||||||||||||||||||| |||| ||||
Rat Nr-CAM:    739 GACACTATAGCTGCTAATTTGAGTGACACTGAGTTTTATGGTGCTAAATCTAGTAAAGAG 798

Human Nr-CAM:  781 AGGCCACCAACATTTTTAACTCCAGAAGGCAATGCAAGTAACAAAGAGGAATTAAGAGGA 840
                   |||||||||||||| ||||||||||| ||||||| |||| |||| || ||||||||||||
Rat Nr-CAM:    799 AGGCCACCAACATTTCTAACTCCAGAGGGCAATGAAAGTCACAAGGAAGAATTAAGAGGA 858

Human Nr-CAM:  841 AATGTGCTTTCACTGGAGTGCATTGCAGAAGGACTGCCTACCCCAATTATTTACTGGGCA 900
                   || ||||||||| |||||||||||||||||||| ||||| ||| ||||||||||||| ||
Rat Nr-CAM:    859 AACGTGCTTTCCCTGGAGTGCATTGCAGAAGGCCTACCTACTCCAGTTATTTACTGGATC 918

Human Nr-CAM:  901 AAGGAAGATGGAATGCTACCCAAAAACAGGACAGTTTATAAGAACTTTGAGAAAACCTTG 960
                   |||||||||||||| ||| ||    ||| |||| ||||| ||||||| ||||||||||||
Rat Nr-CAM:    919 AAGGAAGATGGAACGCTTCCTGTCAACCGGACGTTTTATCGGAACTTTAAGAAAACCTTG 978

Human Nr-CAM:  961 CAGATCATTCATGTTTCAGAAGCAGACTCTGGAAATTACCAATGTATAGCAAAAAATGCA 1020
                   |||||||||||| || |||||||||||||||||||||| || || |||||||||| |||
Rat Nr-CAM:    979 CAGATCATTCATGTCTCTGAAGCAGACTCTGGAAATTATCAGTGCATAGCAAAAAACGCA 1038

Human Nr-CAM: 1021 TTAGGAGCCATCCACCATACCATTTCTGTTAGAGTTAAAGCGGCTCCATACTGGATCACA 1080
                   || ||||||| |||| ||||||||||||| ||||| |||||||||||  ||||||| | |
Rat Nr-CAM:   1039 TTGGGAGCCGTCCATCATACCATTTCTGTCACAGTTAAAGCGGCTCCCTACTGGATTGTT 1098

Human Nr-CAM: 1081 GCCCCTCAAAATCTTGTGCTGTCCCCAGGAGAGGATGGGACCTTGATCTGCAGAGCTAAT 1140
                    | ||||| || || |||||  |||||||| ||| |||||||| || |||||||||||||
Rat Nr-CAM:   1099 GCACCTCACAACCTCGTGCTTTCCCCAGGGGAGAATGGGACCCTCATCTGCAGAGCTAAC 1158

Human Nr-CAM: 1141 GGCAACCCCAAACCCAGAATTAGCTGGTTAACAAATGGAGTCCCAATAGAAATTGCCCCT 1200
                   |||||||| |||||||||||||||||||||||||||||||||||| ||||||||| | |
Rat Nr-CAM:   1159 GGCAACCCAAAACCCAGAATTAGCTGGTTAACAAATGGAGTCCCAGTAGAAATTGCTCTC 1218

Human Nr-CAM: 1201 GATGACCCCAGCAGAAAAAATAGATGGCGATACCATTATTTTTTCAAATGTTCAAGAAAGA 1260
                   ||||||||||| || ||||| ||| |||| |||||||| ||||||||||||||||||||
Rat Nr-CAM:   1219 GATGACCCCAGCCGAAAAATCGATGGTGATACCATTATGTTTTCAAATGTTCAAGAAAGC 1278

Human Nr-CAM: 1261 TCAAGTGCAGTATATCAGTGCAATGCCTCTAATGAATATGGATATTTACTGGCAAACGCA 1320
                   |||||||| || |||||||||||||||||||| ||||||||||||||||| ||||| |||
Rat Nr-CAM:   1279 TCAAGTGCGGTTTATCAGTGCAATGCCTCTAACAAATATGGATATTTACTAGCAAATGCA 1338

Human Nr-CAM: 1321 TTTGTAAATGTGCTGGCTGAGCCACCACGAATCCTCACACCTGCAAACACA         1371
                   |||||||||||||| ||||| |||||||| || || || || | ||||||||
Rat Nr-CAM:   1339 TTTGTAAATGTGCTCGCTGAACCACCTCGGATTCTTACCTCAGCAAACACA         1389
```

FIG. 24A (CONT')

GCGCCGGAATTCGTTAACCTCGAGGATCCGGCTGTG
EcoRI  HpaI  XhoI  BamHI

SEQ ID NO: 33 pCMV-1/3Nr-AS pCMV-neo

NR-CAM GENE, NUCLEIC ACIDS AND NUCLEIC ACID PRODUCTS FOR THERAPEUTIC AND DIAGNOSTIC USES FOR TUMORS

The present application is entitled to and claims priority benefits of U.S. Application No. 60/083,152, filed Apr. 27, 1998; and 60/112,098, filed Dec. 14, 1998, the entire disclosures of which are incorporated herein by reference.

1. FIELD OF THE INVENTION

The present invention relates to the identification of a novel role for the neuron-glia-related cell adhesion molecule (Nr-CAM) gene in tumorigenesis, in particular primary brain tumorigenesis. The present invention is related to the role of Nr-CAM nucleic acids and polypeptides as diagnostic tools to indicate a pre-cancerous condition or cancer, and therapeutic agents based thereon to inhibit Nr-CAM gene expression and/or activity as a method of treating, inhibiting and/or preventing tumorigenesis.

2. BACKGROUND OF THE INVENTION

2.1. Brain Tumors

Brain tumors are among the leading cause of death among young children and adults. A survey by the American Cancer Society has documented that 13,300 people died of brain tumors in 1995 and predicated that over 17,900 would die in 1996 (Parker et al., 1996, CA Cancer J. Clin., 46:5–28). The number of deaths due to brain tumors has been increasing at a significant rate each year. On average, 25,000 Americans are diagnosed with brain cancer yearly. Brain tumors claim the lives of more children than any other form of cancer except leukemia.

The increased incidence of brain tumors is not only evident in children but also in adults. It has been documented that a significant increase in mortality has occurred in adult primary malignant tumors between 1982 and 1996 (Parker et al., 1996). Glioblastomas, astrocytomas and meningiomas are the most common brain tumors that affect adults (Thapar and Laws, 1993, CA Cancer J. Clin., 43:263–271).

The transformation of normal human brain cells into gliomas occurs as a result of the accumulation of a series of cellular and genetic changes (Sehgal, 1998, Cancer Surv., 25:233–275; vonDiemiling et al., 1995, Glia 15:328–338; Furnari et al., 1995, J. Surg. Oncol. 67:234). These genetic alterations include the loss, gain or amplification of different chromosomes. These genetic changes lead to altered expression of proteins that play important roles in the regulation of normal cell proliferation. Several common genetic alternations at the chromosomal level (loss of 17p, 13q, 9p, 19, 10, 22q, 18q and amplification of 7 and 12q) have been observed (Sehgal et al., 1998 J. Surg. Oncol. 67:23; vonDiemiling et al., 1995, Glia 15:328–338; Furnari et al., 1995, Cancer Surv. 25:233–275). These alterations lead to changes in the expression of several genes (p53, RB, INFα/β, CDKN2, MMAC1, DCC, EGFR, PDGF, PDGFr, MDM2, GLI, CDK4 and SAS) during the genesis and progression of human gliomas (Sehgal, 1998, J. Surg. Oncol. 67:234; vonDiemiling et al., 1995, Glia 15:328–338). Recent studies have suggested that altered expression of several other genes (MET, MYC, TGFβ, CD44, VEGF, N-CAML1, $p21^{waf1/cip1}$, trka, MMRs, C4-2, D2-2) and proteins (cathepsins, tenascin, matrix metalloproteases, tissue inhibitors of metalloproteases, nitric oxide synthetase, integrins, IL 13 receptor, Connexin 43, uPAR's extracellular matrix proteins and heat shock proteins) are associated with the genesis of human gliomas (Sehgal, 1998, J. Surg. Oncol. 67:234). Taken together these findings point to the fact that accumulation of multiple genetic mutations coupled with extensive changes in gene expression may be a prerequisite in the etiology of human gliomas. Despite identification of these genetic alterations, the exact series of events that leads to the genesis of human gliomas is not clear.

Glioblastoma multiforme are high grade astrocytomas that grow very rapidly and contain cells that are very malignant (Thapar and Laws, 1993, CA Cancer J. Clin., 43:263–271). chromosomal level or at a gene expression level. These may include inactivation of tumor suppressor genes, activation of oncogenes or specific translocations at the chromosomal level. Some genetic changes at the chromosomal level and gene expression level have been well documented for other brain tumors (Fumari et al., 1995, Cancer Surv., 25:233–275). For example, it has been documented that loss of tumor suppressor(s) genes at chromosome 10, mutations in p53, or overexpression of epidermal growth factor receptor, may be major events leading to glioblastoma multiforme. A number of other genes such as EGFR, CD44, β4 integrins, membrane-type metalloproteinase (MT-MMP), p21, p16, p15, myc, and VEGF have been shown to be overexpressed in different types of brain tumors (Faillot et al., 1996, Neurosurgery, 39:478–483; Eibl et al., 1995, J. Neurooncol., 26:165–170; Previtali et al., 1996, Neuropath. Exp. Neurol. 55:456–465; Yamamoto et al., 1996, Cancer Res. 56:384–392; Jung et al., 1995, Oncogene, 11:2021–2028; Tsuzuki et al., 1996, Cancer 78:287–293; Chen et al., 1995, Nature Med 1:638–643; Takano, et al., 1996, CancerRes., 56:2185–2190; Bogler et al., 1995, Glia 15:308–327). Several cell adhesion molecules (CAMs), such as integrins, cadherins, IgSF proteins (carcinoembryonic antigen, N-CAM and VCAM-1) or lectins, are thought to be involved in tumorigenesis (Johnson, 1991, Cancer Metastat. Rev. 10:11–22). Over-expression of anti-sense to the secreted glycoprotein SPARC (secreted protein, acidic and rich in cysteine), results in suppression of the adhesive and invasive capacities of melanomas (Ledda et al., 1997, Nature (Med). 3:171–176). The cell-surface adhesion molecule MCAM (MUC18) when over-expressed may lead to increased adhesion and metastatic potential of human melanoma cells in nude mice (Xie et al., 1997, Proc. Nat'l Cancer Conf. 38:522). Expression of N-CAM or ICAM (Intercellular adhesion molecule) is related inversely to increased metastasis (Hortsch, 1996, Neuron 17:587–593). Other genes such as p53 show mutations in the majority of brain tumors (Bogler et al., supra). How the interplay of one or more of these genes leads to tumorigenesis is not known but most likely multiple steps are required for neoplastic transformation. The exact series of events that lead to initiation or progression of glioblastoma are not known at present and useful markers for early detection of brain tumors are lacking.

2.2. CAMs

A subfamily of the immunoglobulin superfamily (IgSF) proteins are termed "cell adhesion molecules" (CAMs) (Hortsch, 1996, Neuron 17:587–593).

Several CAM family members are implicated in the process of tumorigenesis including, N-CAM, CEA, (Carcinoembryonic Antigen), DCC (Deleted in Colon Carcinoma) and L1.

CEA is a cell surface glycoprotein of colon mucosal cells. High levels of CEA are observed in the serum of tumor patients (Benchimol, et al., 1989, Cell, 57:327–334). It was demonstrated that over-expression of CEA in malignant cells may disturb intercellular adhesion that may in turn cause tissue disruption leading to the metastasis of primary tumor cells (Albelda, 1993, Lab Invest, 68:4–14; Benchimol et al., 1989).

L1 is another cell adhesion molecule that belongs to the Ig superfamily and is expressed in neuroblastomas, melanomas, lymphocytes and Schwann cells (Izumoto, et al., 1996, Cancer Res, 56:1440–1444). Antibody neutralization experiments demonstrate that L1 is responsible for the highly invasive nature of the C6 glioma cells. Mutations in the L1 are known to be associated with a spectrum of neurological deficiencies including mental retardation (Izumoto et al., 1996).

The neural cell adhesion molecules (N-CAMs) are predominantly though not exclusively, expressed in developing peripheral and central nervous systems of a number of invertebrates and vertebrates. These proteins are generally present on the cell surface and consist of multiple Ig domains, multiple fibronectin type III repeats near the cell membrane and either a transmembrane domain or a glycophosphatidylinositol-linked membrane anchor at the C-terminus (Hortsch, 1996). The N-CAMs can be grouped into 2 major structural families, one resembling N-CAM and the other resembling the liver CAM (L-CAM) and its mammalian homologue uvomorulin or E-cadherins. Within N-CAM, 2 major types are observed, the N-CAM (neuronal CAM) and the neuron-glial CAM (Ng-CAM) (Grumet et al., 1991, J. Cell Biol. 113:1399–1412).

N-CAM is expressed in a wide variety of tissues and is implicated in embryonic development. Over-expression of N-CAM is observed in a variety of tumors including multiple myelomas, small cell carcinomas and adenoid cystic carcinomas. Down regulation of N-CAM is observed in malignant glioma cells (Albelda, 1993; Poley, et al., 1997, Anticancer Research, 17:3021–3024). In Wilm's tumor of kidney, the N-CAM exists in h-PSA form that is less adhesive to surrounding cells and fibers. In a recent study it was demonstrated that high levels of N-CAM were detected in patients with prostate carcinomas (Lynch, et al., 1997, Prostate, 32:214–220). In vivo studies in nude mice demonstrated that N-CAM may be involved not only in adhesive and motile behavior of cells but also in their growth regulation (Poley et al., 1997; Lynch et al., 1997).

DCC is a cell adhesion molecule that belongs to the N-CAM family. DCC was first shown to be expressed in a variety of tumors including the brain and lung but its expression was reduced and mutated in a number of colorectal carcinomas (Fearon, et al., 1990, Cell 61:759–767). The down-regulation or mutation of the DCC molecule leads to the disruption of normal cell-cell adhesion in the intestinal epithelium. This process is known to play an important role in the metastasis of colorectal carcinomas (Albelda, 1993; Fearon et al., 1990).

2.2.1. Nr-CAM

Nr-CAM (neuron-glia related CAM) was cloned from a chicken brain library when Ng-CAM cDNA Clones were being isolated (Grumet et al., 1991, J. Cell Biol. 113: 1399–1412). Monoclonal antibodies against E8 tectal surface protein identified a similar molecule that was cloned from a chicken brain library. This protein was designated Bravo/Nr-CAM (Grumet et al., 1991; Lane et al., 1986, Genomics 35:456–465). The Nr-CAM protein contains 6 Ig domains and 5 fibronectin repeats. Numerous studies on chicken Nr-CAM suggested that it may play an important role in cell-cell adhesion during the development of the vertebrate nervous system. The human homologue of the chicken Nr-CAM has been cloned (Lane et al., 1996, Genomics 35:456–465; see Lane et al., FIG. 1 at pages 458–9 for nucleotide and deduced amino acid sequences of hNr-CAM, incorporated herein by reference).

Sequence analysis of Nr-CAM proteins isolated from human rat, chicken, and mouse showed more than 80% identity. One unique characteristic of hNr-CAM is that the third fibronectin repeat contains a furin-like cleavage site (Grumet, 1991, Current Opinion in Neurobiology, 1:370–376; Suter, et al., 1995, J. Cell Biol., 131:1067–1081). It has also been reported that the 140KDa protein may exist as a doublet (Grumet, et al., 1991, J. Cell Biol., 113:1399–1412; Lane, et al., 1996, Genomics, 35:456–465).

The cytoplasmic tail of the hNr-CAM protein is known to interact with a cytoplasmic protein named ankyrin (Davis, et al., 1993, J. Cell Biol., 121:121–133; Davis, et al., 1996, J. Cell Biol., 135:1355–1367). This region of the hNr-CAM protein is highly conserved among other family members (Ng-CAM, L1, neurofascin and neuroglian protein). Neurofascin and L1 proteins contain a phosphorylation site that may modulate its interaction with ankyrin (Davis, 1993; Davis 1996). Phosphorylation status of hNr-CAM in this region of the protein has not been reported yet. The cytoplasmic tail of the hNr-CAM contains sequences that have potential to interact with PSD-95/discs- large/ZO-1 family of membrane associated proteins (Grumet, et al., 1991, J Cell Biol, 113:1399–1412).

cDNA analysis of rat Nr-CAM revealed two different forms of Nr-CAM as a result of alternative mRNA splicing. The alternatively spliced form of Nr-CAM contains 10-amino acids inserted between the Ig domain and fibronectin domain, and 15-amino-acids inserted after the fourth fibronectin repeat, and complete deletion of the fifth fibronectin repeat (Suter et al., 1995). The extracellular portion of the Nr-CAM protein contains twenty potential sites for N-linked glycosylation (Kayyem, et al., 1992, J Cell Biol, 118:1259–1270; Suter et al., 1995; Grumet, 1991; Cell Tissue Res. 290:423–428).

Nr-CAM is expressed in growing neurites and radial cells of the optic chiasm. Nr-CAM protein family members not only play an important role in cell adhesion but they can interact with other proteins, such as FGF-R, by phosphorylation events to bring about neurite extension. L1-CAM gene mutation may be involved in several neurological disorders (Hortsch, 1996). A number of transformed cells from a variety of tissues also express L1-CAM, and the expression is correlated inversely with the metastatic capacity of a lymphoma cell line in mice, leading to speculation that these CAMs may play a role in metastatic events (Hortsch, 1996). See generally, Albelda, 1993, Lab. Invest. 68:4–14.

It has been demonstrated that hNr-CAM is a brain specific protein and is expressed on neurons, Schwann cells, Muller cells and transiently in the cells of floor plate (Davis, et al., 1996, J Cell Biol, 135:1355–1367; Grumet, Cell Tissue Res, [1991] 290:423–428). The hNr-CAM protein is expressed preferentially on fiber tracts, in spinal cord, cerebellum, tectum, and telencephalon. It is also known to be concentrated in the node of Ranvier, thus demonstrating its potential role in the formation and maintenance of the nodes (Suter, et al., 1995, J Cell Biol, 131:1067–1081). The hNr-CAM is also expressed widely in the retina on cell bodies and fiber layers and on the ganglion cells (Suter et al., 1995; Davis, et al., 1994, J Biol Chem, 269:27163–27166).

The hNr-CAM protein is a cell adhesion molecule that can function as a receptor and as a ligand. It not only interacts with other hNr-CAM molecules on the cell surface but also with other CAMs and extracellular matrix proteins. Some of the proteins that interact with the hNr-CAM include: contactin/F11, axonin-1 ax-1), neurofascin (Nf), Receptor protein tyrosine phosphataseβ (RPTPβ), Ng-CAM, chondroitin sulfate proteoglycans neurocan, and phosphacan (Davis et al., 1994; Grumet et al., 1991; Cell Tissue Res. 290:423–428). Recent analysis has indicated that the cytoplasmic domain of hNr-CAM can directly interact with ankyrins, a family of spectrin-binding proteins (Davis, 1993; Davis, 1996). This interaction may be involved in sending signals from the extracellular domain to the cytoplasm of cells. Antibody binding analysis during the tectal neurite growth has demonstrated that the hNr-CAM can act as a receptor and as a ligand. Some of the major functions of the hNr-CAM are: a) modulation of axonal growth and guidance; b) modulation of the function of non-neuronal glial cells; c) synapse formation and maturation of the central nervous system; and d) as a heterophilic neuronal receptor (Grumet, 1991 Cell Tissue Res. 290:423–428).

Citation of references herein shall not be construed as an admission that such references are prior art to the present invention.

3. SUMMARY OF THE INVENTION

The present invention relates to the discovery of a novel role for Nr-CAM in the aberrant proliferative behavior of a number of cell types, including numerous primary tumors and derived cell lines. In particular, the present invention relates to the identification of the role of Nr-CAM in cell transformation and tumorigenesis, in particular, brain. The present invention encompasses therapeutic and diagnostic applications based on Nr-CAM proteins, nucleic acids, and agonists and antagonists, for the treatment, inhibition or prevention of tumorigenesis. The present invention further encompasses therapeutic and diagnostic applications based on a ligand of Nr-CAM proteins, nucleic acids, and agonists and antagonists, for the treatment, inhibition or prevention of tumorigenesis. The present invention further encompasses screening assays to identify modulators of Nr-CAM activity and/or expression as potential therapeutic agents for the treatment, inhibition and/or prevention of a transformed phenotype or tumorigenesis.

The present invention is based, in part, on the Applicants' surprising discovery that the Nr-CAM nucleotide sequence and encoded protein product is expressed at high levels in glioblastoma multiforme tissue, astrocytomas, gliomas, glioblastoma tumor tissues, as well as, certain other forms of tumors and cancers.

In one embodiment, the present invention encompasses nucleotide sequences complementary to the nucleotide sequence of Nr-CAM, such as primers, fragments or antisense nucleotides which may be used to determine the level of Nr-CAM expression in a tissue or cell culture sample as prognostic of a pre-cancerous or transformed cell phenotype; or to inhibit Nr-CAM expression as a method of treating, inhibiting or preventing a pre-cancerous or transformed cell phenotype. In a specific embodiment, the Nr-CAM gene is a human gene and the Nr-CAM protein is a human protein.

The present invention also encompasses inhibitors of Nr-CAM activities related to cellular transformation. Nr-CAM is a known protein thought to play a role in cell-cell adhesion, e.g. during development of not only the vertebrate nervous system but also by interaction with other proteins, such as FGF-R, in neurite extension. The present invention encompasses peptide fragments or antagonists, antibodies, or small compounds which may inhibit or compete with ligands binding to Nr-CAM and thus inhibit Nr-CAM activity. The invention further encompasses peptide fragments (and derivatives and analogs thereof) which comprise one or more domains of a Nr-CAM protein which may be used to prevent ligands binding to Nr-CAM. Antibodies to Nr-CAM, and to Nr-CAM derivatives and analogs, are additionally provided. Methods of production of the Nr-CAM proteins, derivatives and analogs, e.g., by recombinant means, are also provided.

The present invention further encompasses screening assays to identify compounds which inhibit Nr-CAM nucleic acid expression or nucleic acid product activity as potential therapeutics for the treatment and/or prevention of tumorigenesis. In particular, the present invention encompasses host cell lines or transgenic animals which express Nr-CAM at high levels which have utility as tools for screening assays to identify agents which inhibit Nr-CAM expression and/or activity as potential therapeutic agents for the treatment and prevention of tumorigenesis.

The present invention also encompasses therapeutic and diagnostic methods and compositions based on Nr-CAM proteins and nucleic acids. Therapeutic compounds of the invention include but are not limited to Nr-CAM proteins and analogs and derivatives (including fragments) thereof; antibodies thereto; nucleic acids encoding the Nr-CAM proteins, analogs, or derivatives; and Nr-CAM antisense nucleic acids.

The invention provides for treatment of disorders of overproliferation (e.g., tumors, cancer and hyperproliferative disorders) by administering compounds that decrease or antagonize (inhibit) Nr-CAM function (e.g., antibodies, antisense nucleic acids, ribozymes).

The invention also provides methods of treatment of disorders involving deficient cell proliferation (growth) or in which cell proliferation is otherwise desired (e.g., degenerative disorders, growth deficiencies, lesions, physical trauma) by administering compounds that promote Nr-CAM activity (e.g., an agonist of Nr-CAM; nucleic acids that encode Nr-CAM).

Animal models, diagnostic methods and screening methods for predisposition to disorders, and methods for identification of Nr-CAM agonists and antagonists, are also provided by the invention.

3.1. Definitions and Abbreviations

As used herein, underscoring or italicizing the name of a gene shall indicate the gene, in contrast to its encoded protein product, which is indicated by the name of the gene in the absence of any underscoring or italicizing. For example, "Nr-CAM" shall mean the Nr-CAM gene, whereas "Nr-CAM" shall indicate the protein product of the Nr-CAM gene.

As used herein, the following terms shall have the meanings indicated.

Nr-CAM nucleotides or coding sequences: DNA sequences encoding Nr-CAM mRNA transcripts, protein, polypeptide or peptide fragments of Nr-CAM protein, and Nr-CAM fusion proteins, and RNA sequences corresponding to Nr-CAM mRNA transcripts and RNA sequences which are complementary to the mRNA transcript, Nr-CAM nucleotide sequences encompass RNA, DNA, including genomic DNA (e.g. the Nr-CAM gene) and cDNA.

Nr-CAM: gene products, e.g., transcripts and the Nr-CAM protein. Polypeptides or peptide fragments of the protein are referred to as Nr-CAM polypeptides or Nr-CAM peptides. Fusions of Nr-CAM protein, polypeptides, or peptide fragments to an unrelated protein are referred to herein as Nr-CAM fusion proteins.

As used herein, the following terms shall have the abbreviations indicated.

CD: cytoplasmic domain
DD-PCR: differential display—polymerase chain reaction
ECD: extracellular domain
FNHA: fetal normal human astrocytes
GMTT: glioblastomas multiforme tumor tissue
MTB: multiple tissue blot
MTT: meningioma tumor tissue
NBT: normal brain tissue
ORF: open reading frame
RT-PCR: reverse transcription—polymerase chain reaction
TM: transmembrane domain
UTR: untranslated region
Brain Tumor Cell Lines:
  CCF-STTG1: astrocytoma grade IV
  D283 Med: medulloblastoma
  DBTRG-05MG: glioblastoma multiforme
  Hs 683: glioma
  IMR-32: neuroblastoma
  PFSK-1: primitive neuroectodermal tumor
  SW 1783: astrocytoma grade III

4. DESCRIPTION OF THE FIGURES

FIG. 1 is an autoradiogram of DD-PCR gel illustrating expression of hNr-CAM (designated D4–1) and of a control D1–2 gene in normal brain tissue (N) and brain tumor (T) tissue, i.e., glioblastoma multiforme (GM).

FIGS. 2(A–D) present the nucleotide and amino acid sequences of human Nr-CAM as well as the results of nucleotide sequence analysis as described in Section 6 (Figure 2C) and a schematic illustration of the hNr-CAM gene showing the area used herein for antisense targeting (FIG. 2D). FIG. 2A presents the nucleotide sequence of human Nr-CAM (SEQ ID NO: 1). Features of the nucleotide sequence include the following: Nucleotides 130–3615 encode the extracellular domain; nucleotides 202–4026 encode product=hBRAVO-Nr-CAM; nucleotides 316–483 encode the Immunoglobulin I domain; nucleotides 613–768 encode the Immunoglobulin II domain; nucleotides 988–1134 encode the Immunoglobulin III domain; nucleotides 1258–1410 encode the Immunoglobulin IV domain; nucleotides 1540–1719 encode the Immunoglobulin VI domain; nucleotides 2113–2265 encode the first Fibronectin (Fn) repeat; nucleotides 2413–2565, the second Fn repeat; nucleotides 2710–2886, the third Fn repeat; nucleotides 3028–3186 the fourth Fn repeat; nucleotides 3370–3510, the fifth Fn repeat; nucleotides 2616–3684, the transmembrane region; nucleotides 3685–4036, the intracellular domain; and nucleotides 4030–4134 constitute a 3' untranslated region. FIG. 2B presents the amino acid sequence of human Nr-CAM (SEQ ID NO: 2). The hydrophobic signal sequence is underlined. FIGS. 2A and 2B are adapted from Lane et al., 1996, Genomics 35:456–465.

FIG. 2C illustrates nucleotide sequence identity analysis between previously cloned hNr-CAM (Accession Number U55258; SEQ ID NO: 3), rat Nr-CAM (Accession Number U81037; SEQ ID NO: 4) and the sequence of clone D4-1 (SEQ ID NO: 5) obtained by cloning the hNr-CAM isolated by DD-PCR into pCRII vector (Invitrogen). Sequence identity analysis was performed using the DNasis program from Hitachi Software (South San Francisco, Calif.). Stars (*) indicate presence of identical nucleotides among the sequences.

FIG. 2D presents a schematic of the hNr-CAM gene, including, in particular, the area used herein for antisense targeting. The arrow indicates this area. See text, Section 7 for details.

FIGS. 3(A–F) illustrate differential expression of Nr-CAM in glioblastoma multiforme tissue (GM) when compared to normal brain tissue (NT). The technique of in situ hybridization was used. FIGS. 3(A, B and C) are from one GM tumor while FIGS. 3(D, E and F) are from a second GM tumor. FIGS. 3(A and D) show tumor regions and one hybridized with hNr-CAM anti-sense probes. FIGS. 3(B and E) show serial sections of A and D, and are hybridized with hNr-CAM sense probes. FIGS. 3(C and F) show normal brain regions of serial sections of the same brain as sections A and D, respectively, and are hybridized with hNr-CAM anti-sense probe. Cells expressing hNr-CAM are indicated by arrows.

Figure 4B:
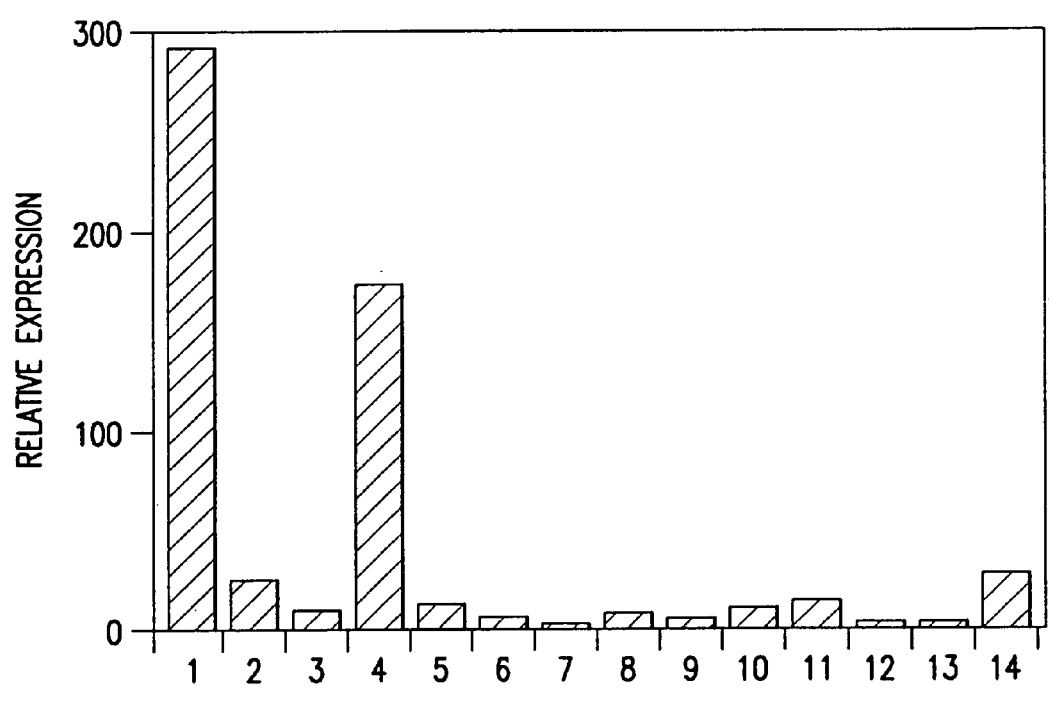

FIGS. 4(A–B) illustrate differential expression of hNr-CAM in normal and tumor tissues. FIG. 4A is a gel obtained using RT-PCR of total RNA of a variety of tissues. The upper panel of FIG. 4A shows expression of hNr-CAM and the lower panel shows expression of a central, housekeeping gene D1-2. FIG. 4B is a bar graph showing relative expression of hNr-CAM after correction for gel load based on D1-2 expression. In both FIGS. 4A and 4B, the specific tissue in each of lanes 1–14 is as follows: Lane 1, glioblastoma IV; 2, recurrent meningioma; 3, meningioma; 4, normal brain (GS); 5, neuroblastoma; 6, recurrent glioma; 7, glioblastoma multiforme; 8, melanoma; 9, normal breast; 10, tumor breast; 11, benign prostate; 12, prostate tumor; 13, normal brain; and 14, glioma III. Recurrent gliomas represent a tissue from the same patient previously diagnosed with GM.

Figure 5B:
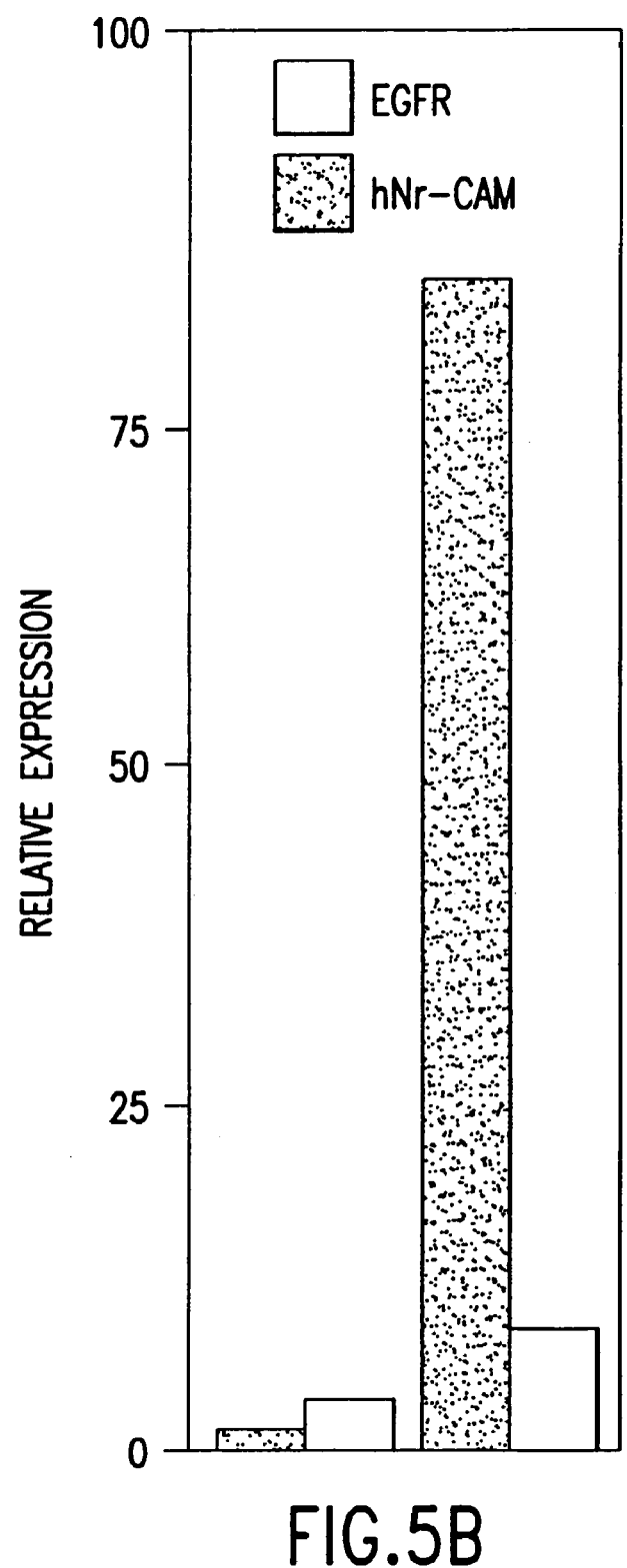

FIGS. 5(A and B) illustrate differential expression of HNR-CAM in normal brain tissue and astrocytoma tumor tissue. FIG. 5A is a gel obtained using RT-PCR of total RNA of normal or astrocytoma tissue. The upper panel of FIG. 5A shows expression of hNr-CAM; the middle panel, EGFR (epidermal growth factor receptor, a known brain tumor maker) and the lower panel, D1-2. FIG. 5B is a bar graph showing the relative expression of hNr-CAM and EGFR after normalizing with D1-2 gel loading. In both FIGS. 5A and 5B, Lane a is normal brain tissue and Lane b is astrocytoma tumor tissue.

Figure 6A:
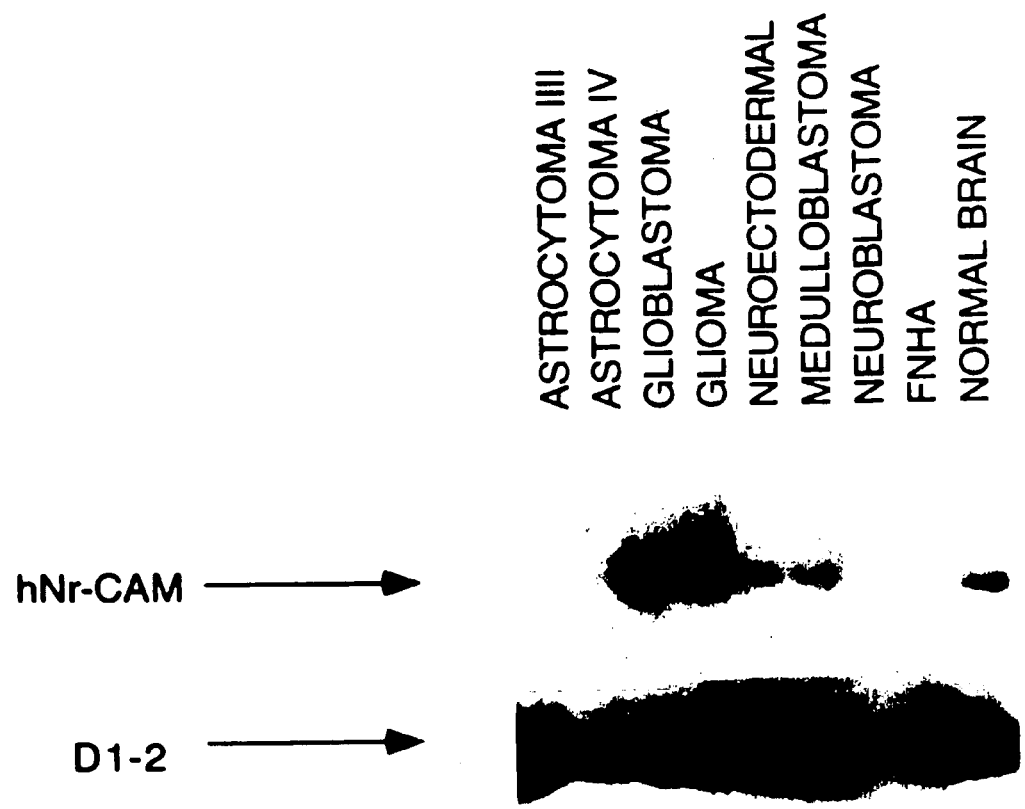
Figure 6B:
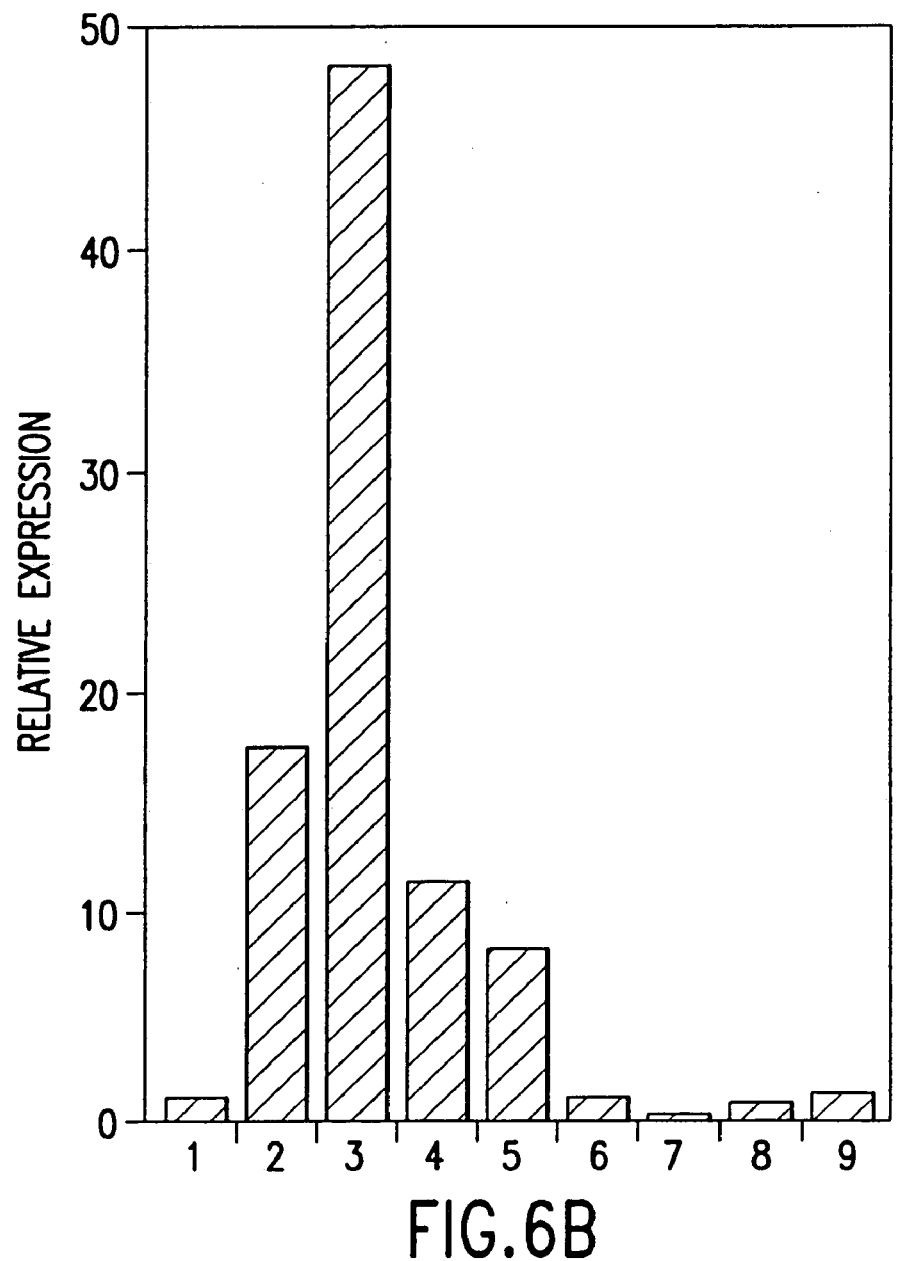

FIGS. 6(A and B) illustrate expression of hNr-CAM in normal brain and brain tumor cell lines. FIG. 6A is an autoradiogram of a Southern blot of hNr-CAM expression (upper panel); and of D1-2 expression (lower panel) in various brain cell lines. FIG. 6B is a bar graph showing relative expression of hNr-CAM in respective cell lines after correction for gel loading based on D1-2 expression. In both FIGS. 6A and 6B, the specific cell line in each of Lanes 1–9 is as follows: Lane 1, astrocytoma III; 2, astrocytoma IV; 3, glioblastoma; 4, glioma; 5, neuroectodermal; 6, medulloblastoma; 7 neuroblastoma; 8, FNHA; and 9, normal brain.

Figure 7A:
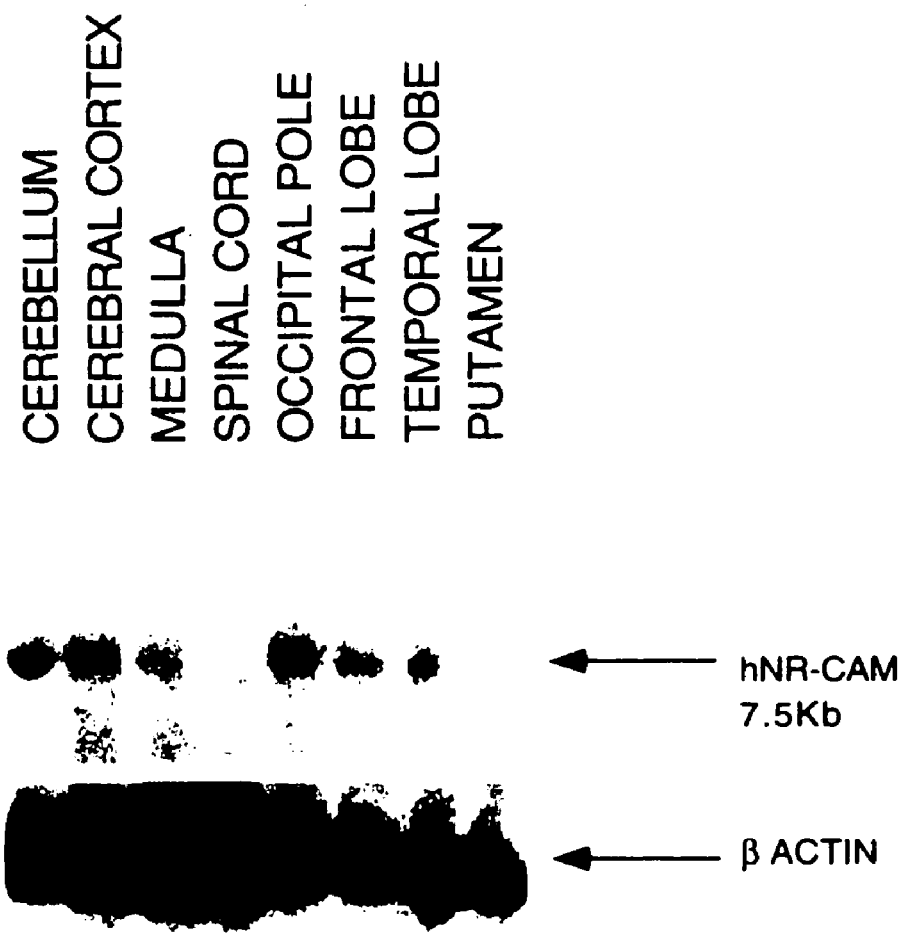
Figure 7B:
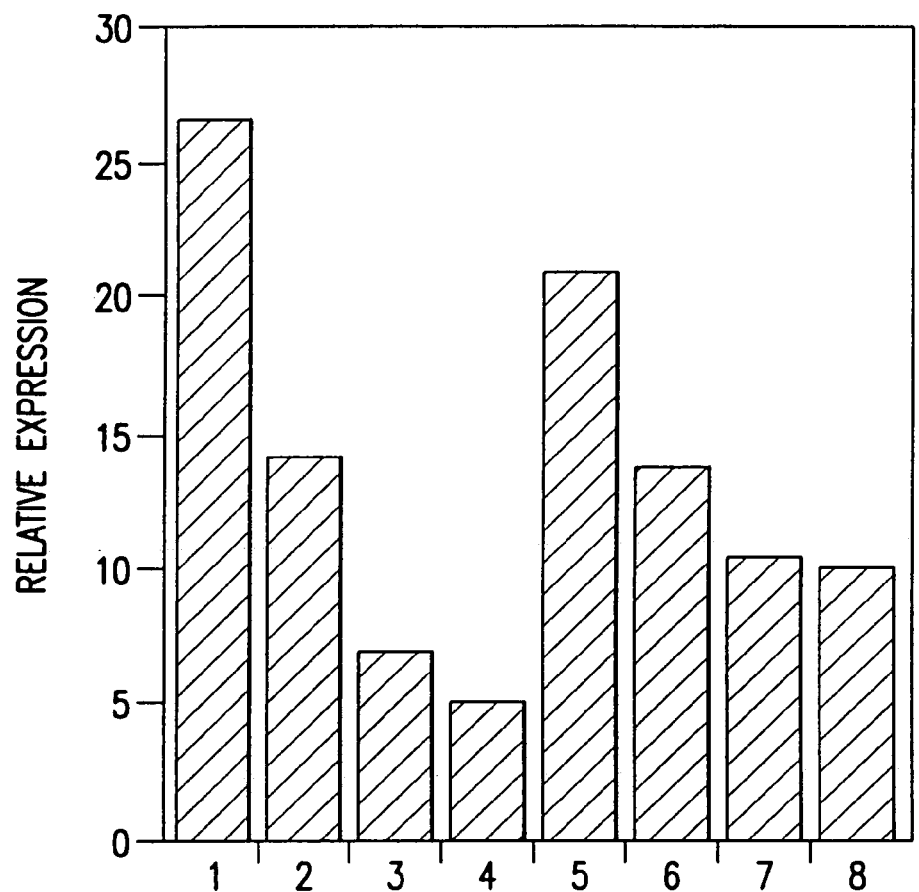

FIGS. 7(A and B) illustrate expression of hNr-CAM in different regions of the brain. FIG. 7A is an autoradiogram of a Northern blot of hNr-CAM expression (upper panel)

and of β-actin expression (lower panel) in a variety of regions (Lanes 1–8) of normal adult brain. β-actin expression serves as an internal control for gel loading for different regions of the brain. FIG. 7B is a bar graph showing the relative expression of hNr-CAM in different brain regions after correction for gel loading based on β-actin expression. In both FIGS. 7A and 7B, the specific region of brain in each of Lanes 1–8 is as follows: Lane 1, cerebellum; 2, cerebral cortex; 3, medulla; 4, spinal cord; 5, occipital pole; 6, frontal lobe; 7, temporal lobe; and 8, putamen.

Figure 8A:
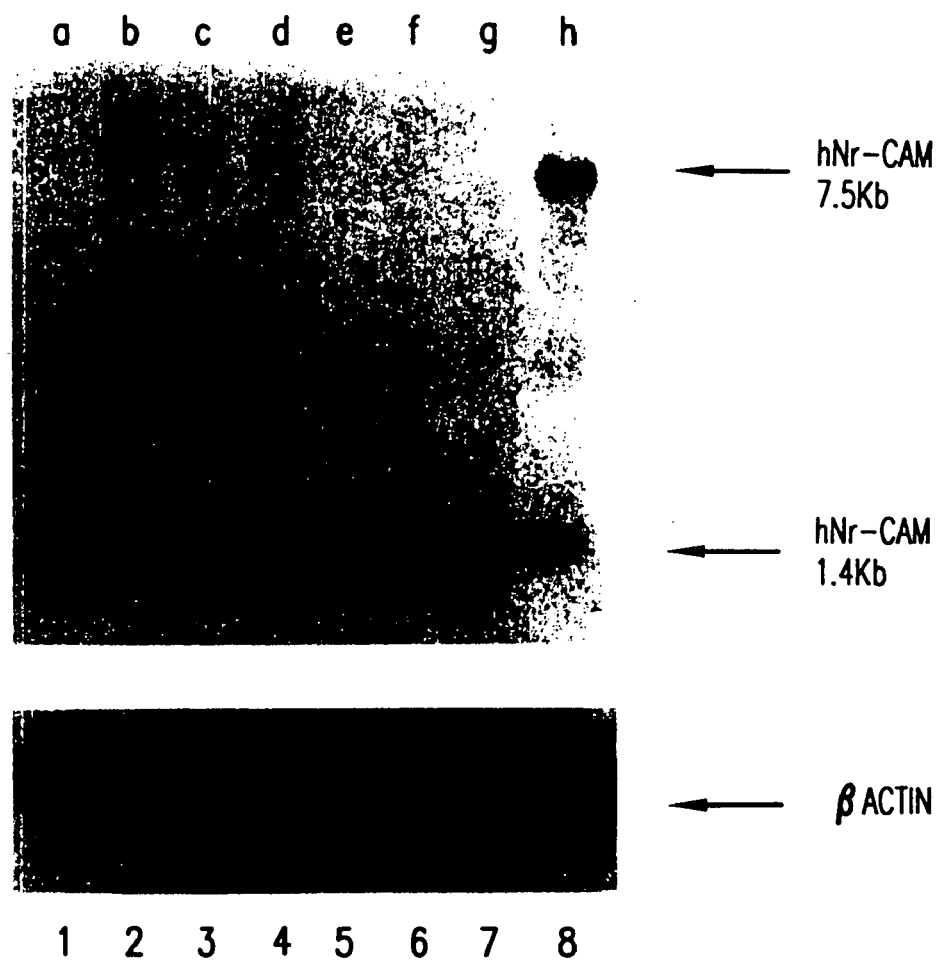
Figure 8B:
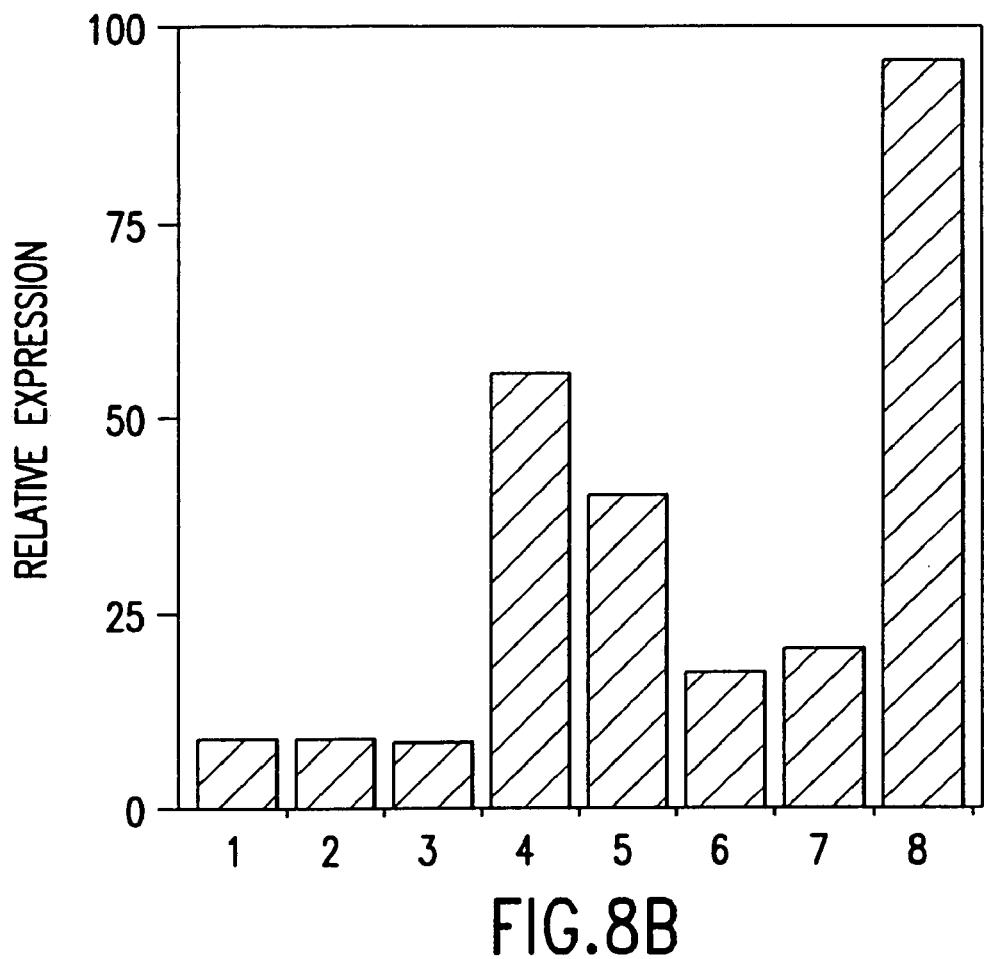

FIGS. 8(A and B) illustrate expression of hNr-CAM in human cancer cell lines (Lanes a–h). FIG. 8A is an autoradiogram of a Northern blot of hNr-CAM expression (upper panel) and of β-actin expression (lower panel). FIG. 8B is a bar graph of the relative expression of hNr-CAM after correction for gel loading based on β-actin expression. In both FIGS. 8A and 8B, the specific human cancer cell line in each of Lanes a–h is as follows: Lane a, promyelocytic leukemia (HL-60); b, HeLa cells (S3); c, chronic myelogenous leukemia (K-562); d, lymphoblastic leukemia (MOLT-4); e, Burkitt's lymphoma (Raji); f, colorectal adenocarcinoma (SA 480); g, lung carcinoma (A549); and h, melanoma (G361).

FIG. 9 illustrates genomic Southern blot analysis of hNr-CAM in several brain tumor cell lines and in the NIH 3T3 cell line. Upper panel shows an ethidium bromide-stained gel of genomic DNA digested with EcoRI restriction enzyme. Lower panel shows an autoradiogram of the Southern blot. The arrow indicates hNr-CAM. In both panels, the brain tumor cell lines in each of Lanes 1–4 is as follows: Lane 1, NIH 3T3 cell line; 2, astrocytoma III; 3, glioma and 4, glioblastoma cell line.

Figure 10A:
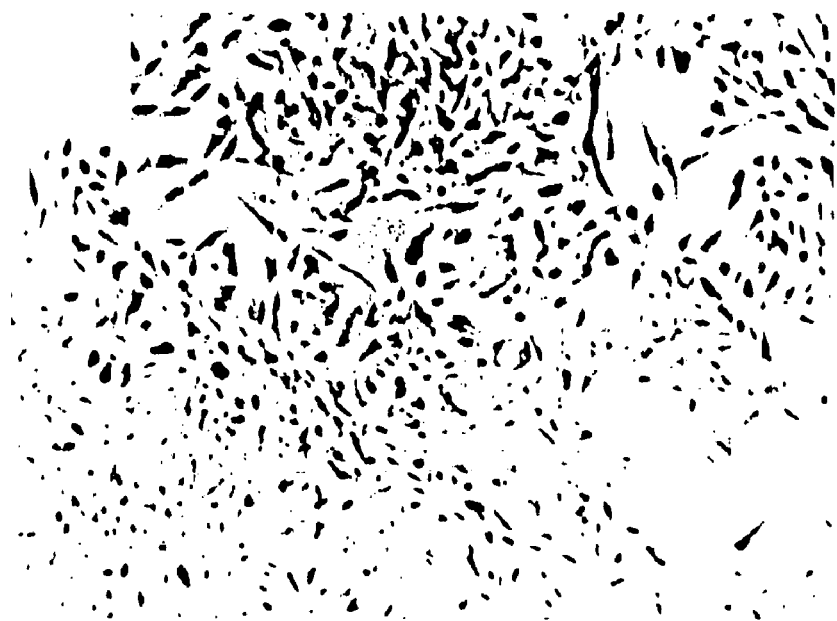
Figure 10B:

FIGS. 10(A and B) illustrate the effects of antisense hNr-CAM expression on the morphology of glioblastoma (GB) cells. FIG. 10A shows GB cells transfected with p-CMV-neovector only. FIG. 10B shows GB cells transfected with p-CMV-neovector containing antisense hNr-CAM.

Figure 11:
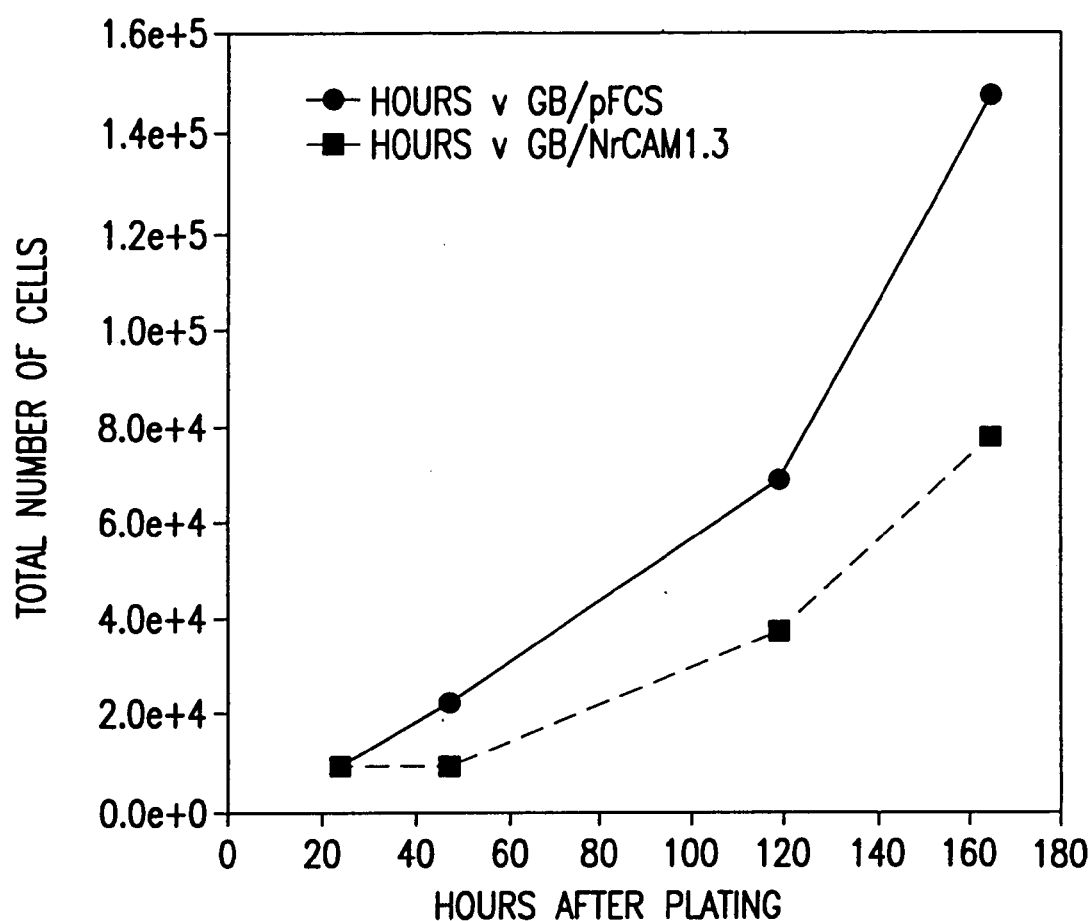

FIG. 11 is a graph illustrating the effect of anti-sense hNr-CAM expression on the proliferation of glioblastoma cells.

Figure 12:
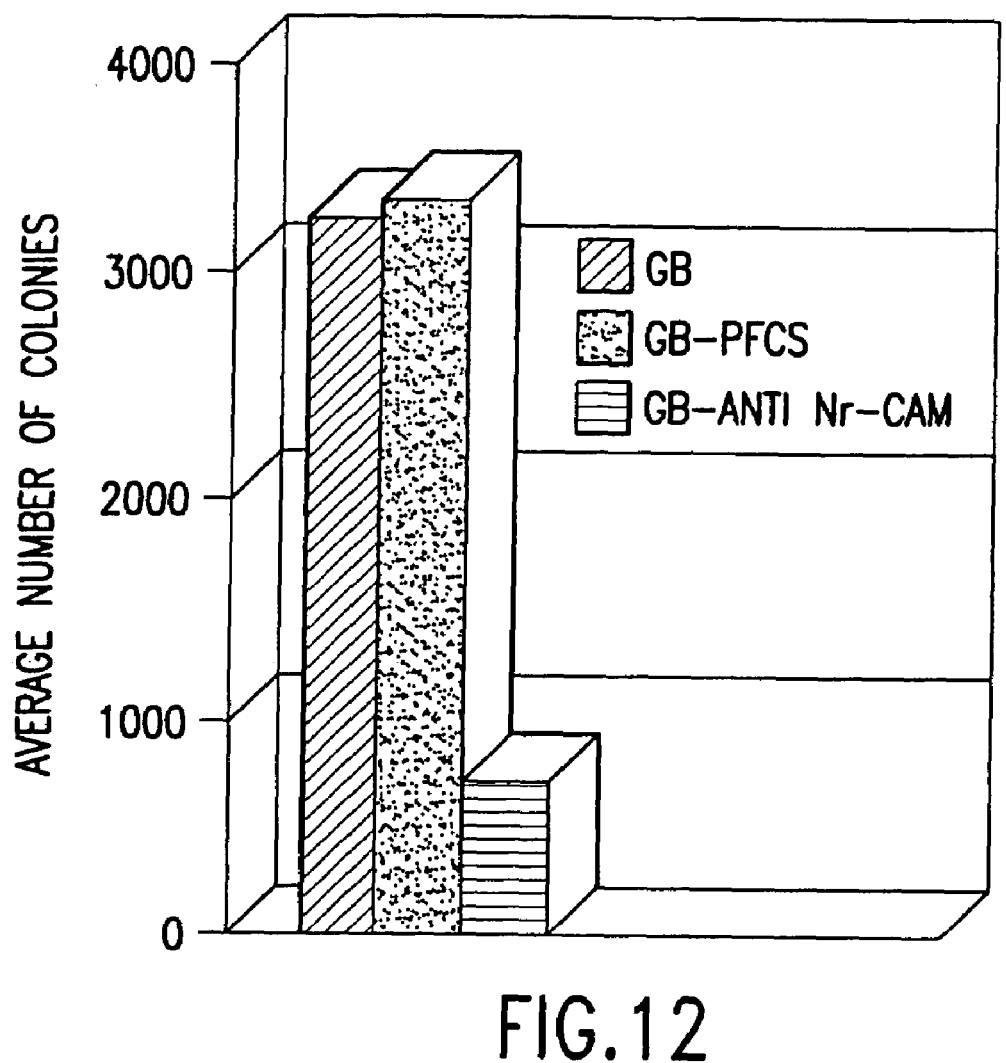

FIG. 12 is a bar graph illustrating the effect of anti-sense hNr-CAM on soft agar colony formation of glioblastoma cells. GB represents Glioblastoma cells; GB-PFCS, represents glioblastoma cells with vector alone; GB-Anti-Nr-CAM, represents GB cells expressing Nr-CAM 1/3.

Figure 13:
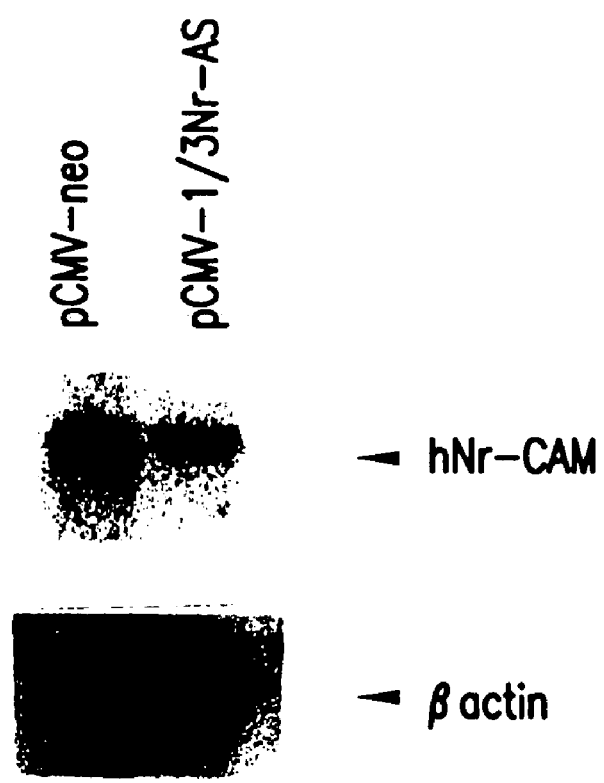

FIG. 13 illustrates the effect of overexpression of antisense hNr-CAM (pCMV-1/3 Nr-AS) on native hNr-CAM mRNA level. See text Section 7.1.6. for details.

Figure 14A:
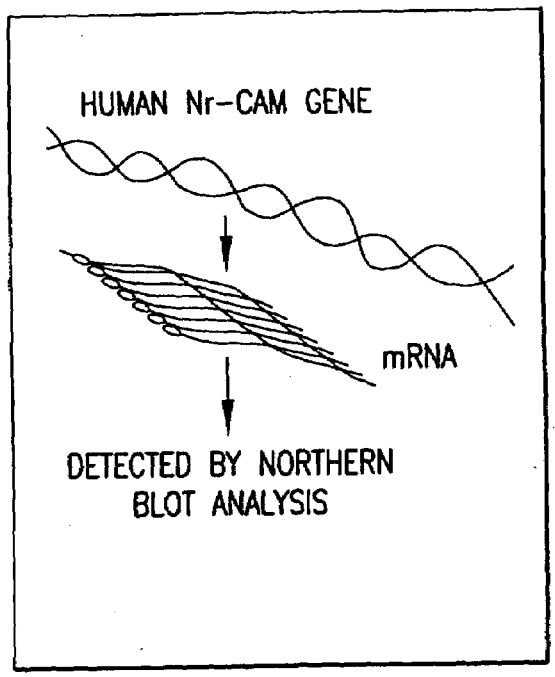
Figure 14B:
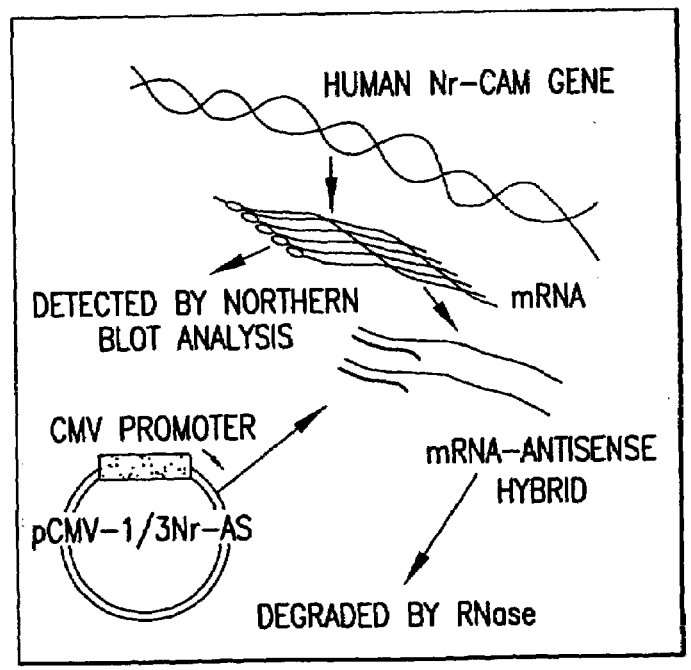

FIGS. 14(A and B) schematically illustrate the effect of antisense hNr-CAM expression in glioblastoma cells. FIG. 14A shows untransfected cells and FIG. 14B shows pCMV-1/3Nr-AS transfected cells.

FIGS. 15(A–D) illustrate effect of antisense hNr-CAM expression on morphology of glioblastoma (GB) cells. FIGS. 15(A and B) show 5GB cells transfected with pCMV-neovector only, i.e., control cells (at different magnifications). FIGS. 15(C and D) show 5 GB cells transfected with pCMV-1/3Nr-AS (at different magnifications). Spindle shaped cells are indicated by arrows. See text Section 7.2.1. for details.

Figure 15A:
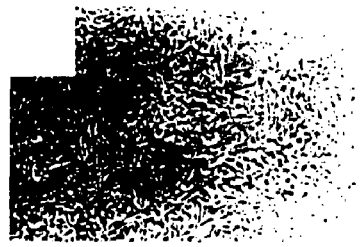
Figure 15B:
Figure 15C:
Figure 15D:

FIGS. 16(A–D) show the effect of serum treatment on the morphology of the pCMV-1/3Nr-AS transfected 5GB cells. 5GB (pCMVneo or pCMV-Nr-1/3AS transfected) cells were plated at an approximate density of $3 \times 10^4$. Both cell types were treated with different concentrations of FBS. FIGS. 15A, B, C, and D, respectively, show 5GB cells (pCMV-1/3Nr-CAM transfected) treated with 0.1, 1.0, 2.0 and 5% FBS serum.

Figure 17:
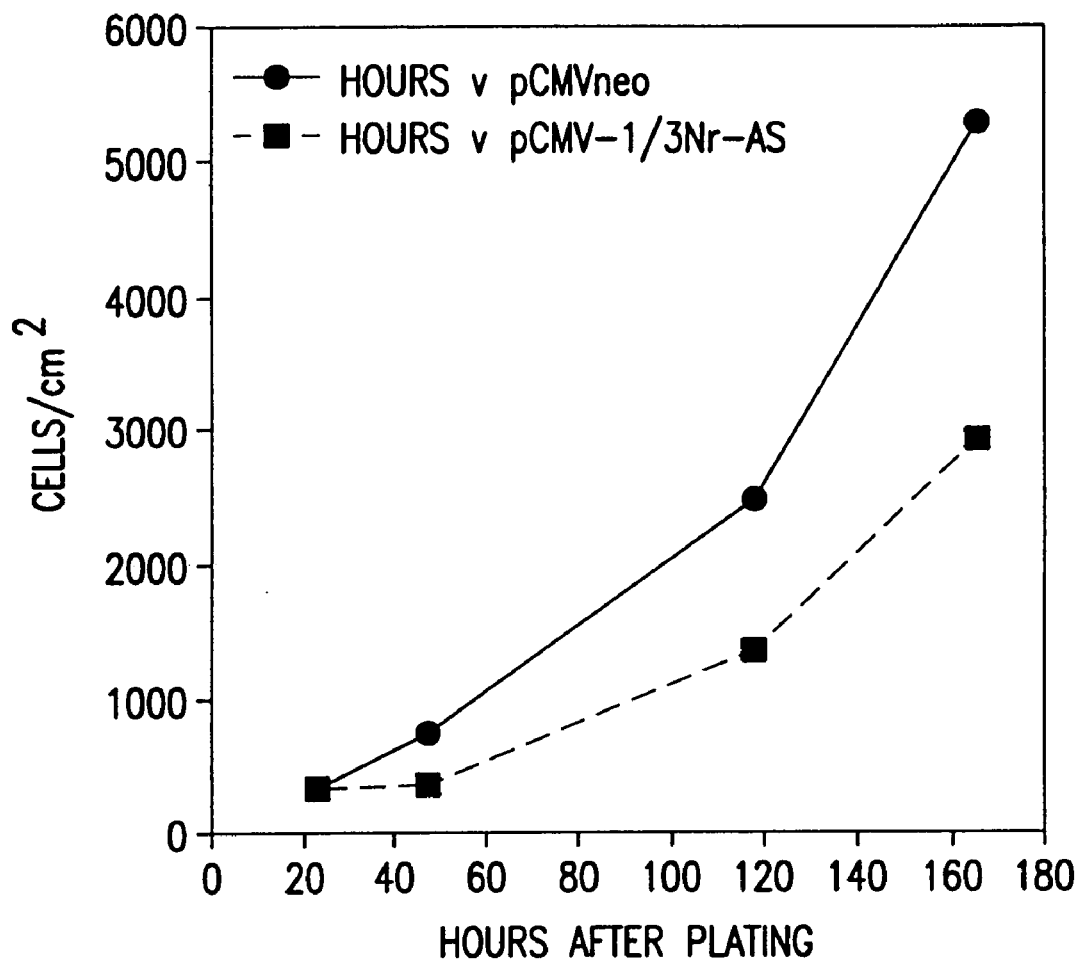

FIG. 17 shows the effect of antisense hNr-CAM pCMV-1/3Nr-AS) expression on the proliferation of 5GB human glioblastoma cell line.

Figure 18:
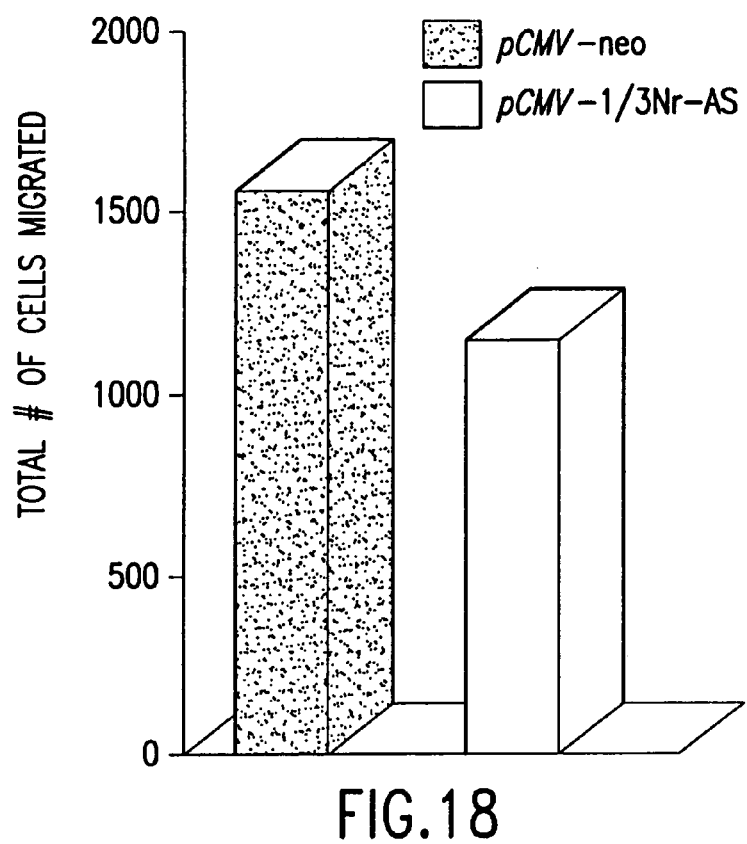

FIG. 18 shows the effect of anti-sense hNr-CAM overexpression on the migration ability of 5GB cells. Briefly, $1 \times 10^6$ pCMV-neo and pCMV-1/3Nr-AS transfected cells twere plated in triplicates in transwell inserts (8 μm) from Coastar (Cambridge, Mass.). Inserts were placed in 6 well tissue culture dishes containing the appropriate growth medium with serum. Cells that migrated through the inserts and settled on the tissue culture dish were fixed with 4% paraformaldehyde. Cell were then stained with hematoxylin and counted under a dissection microscope. Cells that migrated through the transwell inserts are compared for pCMV-neo and pCMV-1/3Nr-AS transfected cells.

Figure 19:
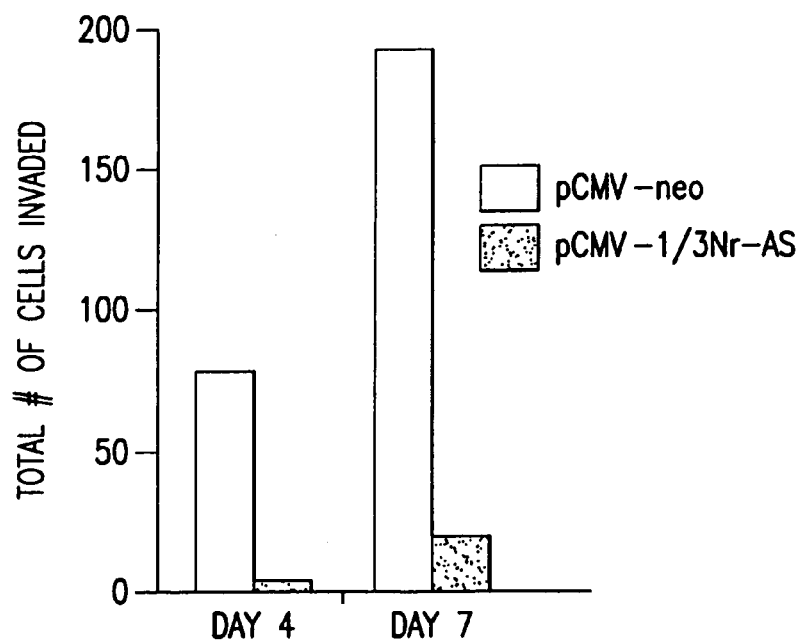

FIG. 19 shows the effect of anti-sense hNr-CAM overexpression on the invasion ability of 5GB cells. Briefly, $1 \times 10^4$ pCMV-neo and pCMV-1/3Nr-AS transfected cells were plated on transwell inserts (8 μm) coated with 825 ng extracellular matrix (ECM) gel from Coastar (Cambridge, Mass.). Inserts were placed in 6 well tissue culture dishes containing the appropriate growth media with serum. Cells that migrated through the inserts and settled on the tissue culture dish were fixed with 4% paraformaldehyde. Cell are then stained with hematoxylin and counted under a dissection microscope. Cells that migrated through the transwell inserts are compared for pCMV-neo and pCMV-1/3Nr-AS transfected cells.

Figure 20C:
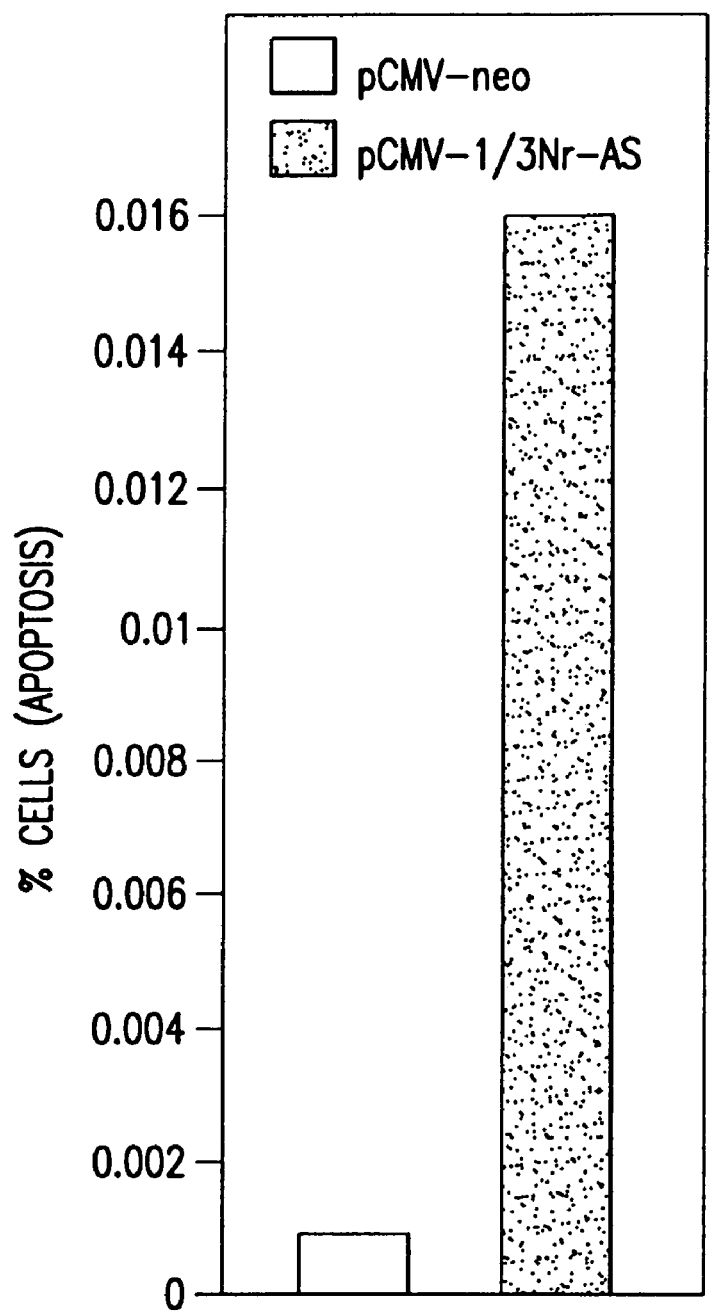

FIGS. 20(A–C) show the effect of UV radiation on antisense hNr-CAM transfected 5GB cells. FIGS. 20(A and B) show pCMV-neo and pCMV-1/3Nr-AS transfected cells analyzed for apoptosis. Arrows indicate cells undergoing apoptosis. FIG. 20C shows % of cells undergoing apoptosis after treatment with 100 units of UV radiation.

Figure 21:

FIG. 21 shows the effect of the antisense hNr-CAM over-expression on the tumor forming ability of 5GB cells in vivo. Lower three mice were injected with pCMV-neo transfected 5GB cells. Top three mice were injected with pCMV-1/3Nr-CAM transfected 5GB cells. The tumors and the site of injection are indicated by arrows.

Figure 22A:
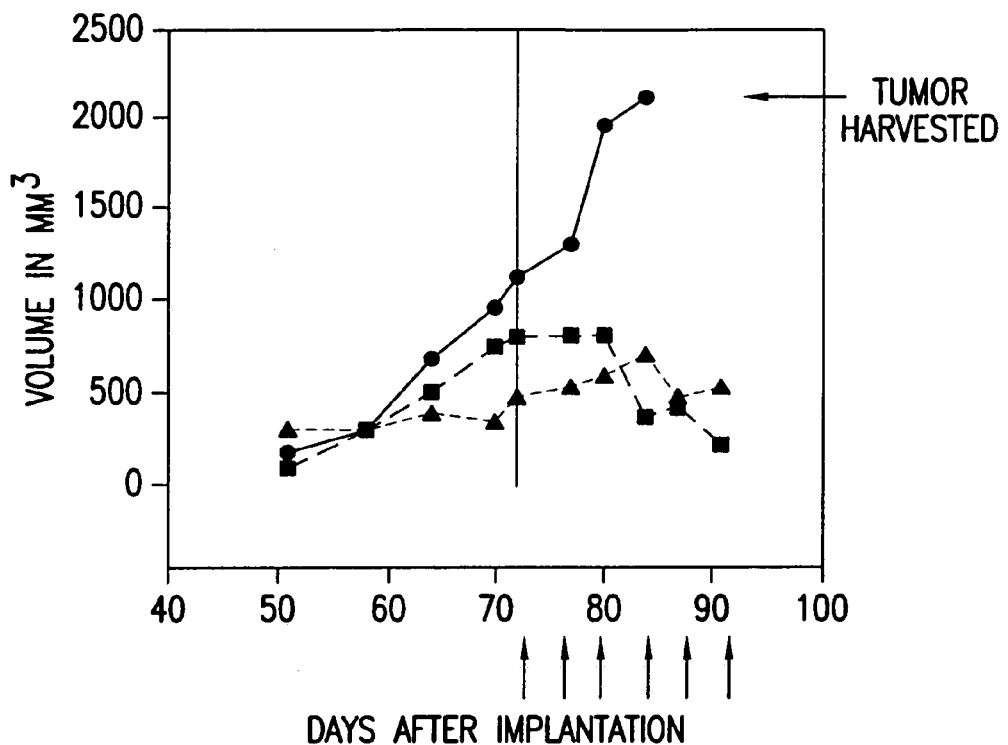
Figure 22B:
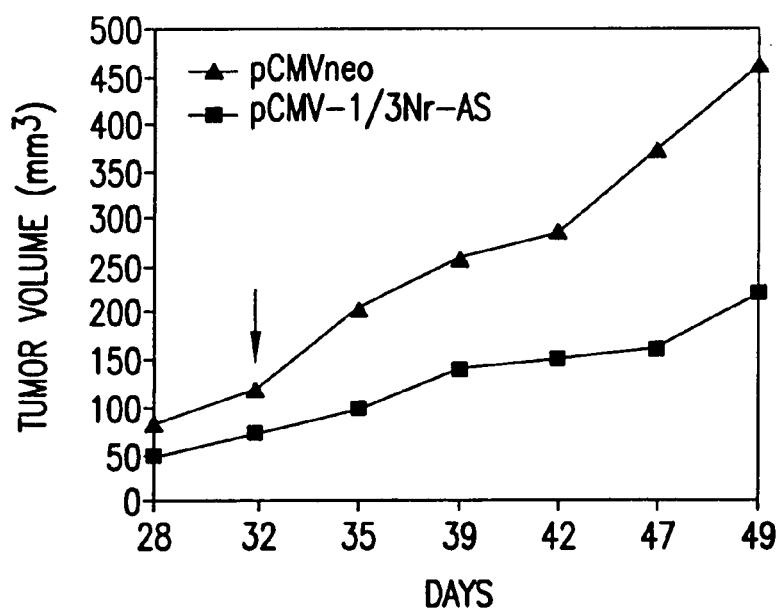

FIGS. 22(A and B) show the effects of intra-tumoral inoculation of plasmid expressing antisense hNr-CAM. FIG. 22A illustrates results obtained using three athymic nude mice injected 72 days post-implantation with 5 GB cells with 50 μg either pCMVneo (control animal (●)) or pCMVneo 1/3 Nr-AS (two animals (■ and Δ). Arrows indicate days of intratumoral injection. See Section 7.2.9. for details. FIG. 22B shows results with four athymic nude mice implanted 3×3 mm pieces of glioblastoma tumor. This tumor was generated previously by injecting $1 \times 10^7$ 5GB glioblastoma cells subcutaneously. 28 days post implantation, 50 μg of either pCMVneo or pCMV1/3Nr-AS plasmids were mixed with DMRIE (liposomes) reagent (Gibco/BRL) and injected twice a week for four weeks around the tumor site. Tumor size was measured twice a week with a caliper and tumor volume was determined. Arrow indicates the first day of intra-tumoral injection. See Section 7.2.9. for details.

Figure 23A:
Figure 23B:
Figure 23C:
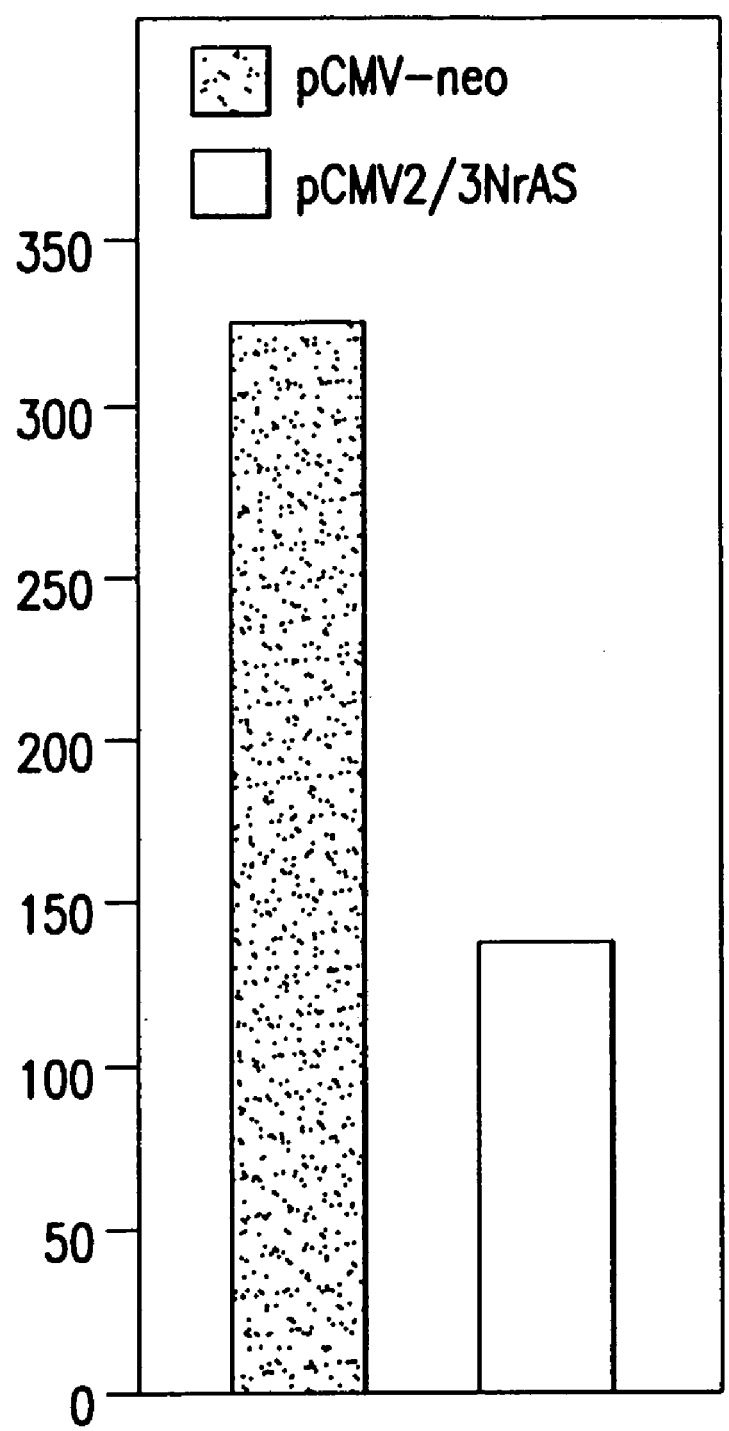

FIGS. 23(A–C) show the effect of antisense hNr-CAM on GB1690 glioblastoma cells. The full length clone for hNr-CAM was provided by William J. Dreyer (California Institute of Technology). A PCR product of approximately 1360 bases (Nucleotide positions 1410–2746) was generated from the full length hNr-CAM clone using specific primers (5'TAGATACAACTAGTCAATGCCTCTAATGAATATGG ATA3' (SEQ. ID. No.: 6); and 5' AGATAGATCCGCG-GAATAGTAAA TCCGATA GCCTTGTA3' (SEQ. ID. No.: 7). The PCR product was then cloned into SpeI and SacII sites of pCMV-neo vector and was termed as pCMV-2/3Nr-AS. The pCMV-neo or pCMV-2/3Nr-AS were then transfected into GB1690 glioblastoma cell line and selected in G418. FIGS. 23(A and B) show cell morphology of cells transfected with pCMV-neo and pCMV-2/3Nr-AS, respectively. Arrows indicate spindle shape cells. FIG. 23C shows a comparison of number of soft agar colonies formed by pCMV-neo and pCMV-2/3Nr-AS transfected GB1690 cells respectively.

FIG. 24 shows the sequence identity analysis between human (SEQ ID NO: 31) and rat (SEQ ID NO: 32) Nr-CAM nucleotide sequence.

Figure 25B:
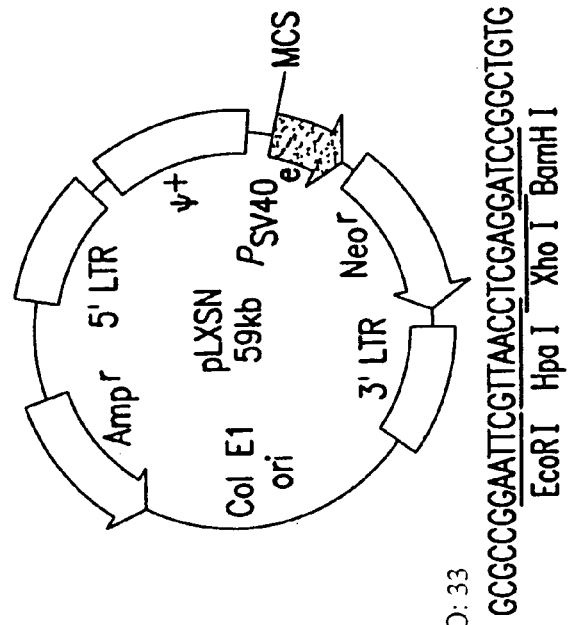
Figure 25A:
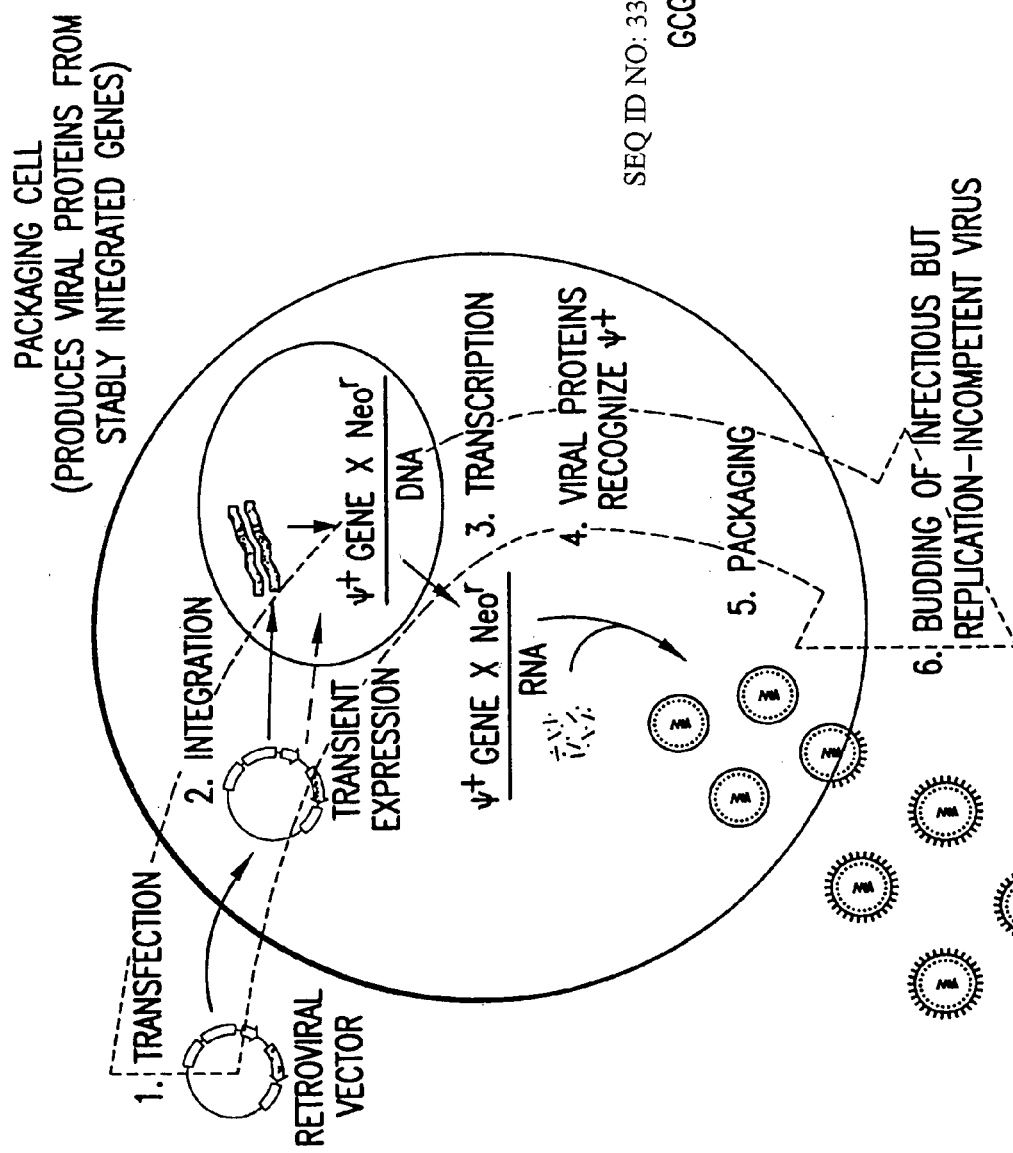

FIGS. 25(A and B) schematically show the packaging of infectious, replication-incompetent retroviral particles (FIG. 25A) and a retroviral vector (FIG. 25B). The retroviral vector, containing the gene of interest (antisense hNr-CAM), a selection gene (Neor), and psi+, the packaging signal necessary for retrovirus particle formation, are stably integrated or transiently expressed. The packaging cell line provides the other genes necessary for particle formation which have been deleted from the vector: gag (structural proteins), pol (reverse transcriptase, integrase), and env (coat glycoproteins). Virus released from this cell line contains the products of these genes (and is infectious), but lacks the genes themselves, thus preventing retroviral production from subsequently infected cell lines. FIG. 25B shows pLXSN retroviral vector that can be used for cloning antisense hNr-CAM gene.

Figure 26A:
Figure 26B:

FIGS. 26(A and B) show the identification of differentially expressed genes in 5GB glioblastoma cells transfected with pCMVneo (FIG. 26B) or pCMV1/3Nr-AS (FIG. 26A) vectors. Differential hybridization was performed as described in Section 8. White arrow in FIG. 26A indicates novel cDNA (accession# H77485) and selectin gene is indicated by black arrow (See FIG. 26B).

5. DETAILED DESCRIPTION OF THE INVENTION

The present invention relates to the identification of a novel role of Nr-CAM in cell transformation and aberrant cellular proliferation. In particular, the present invention relates to the discovery of altered expression of Nr-CAM in a number of primary tumors and cell lines derived from tumors, in addition to, the altered expression of ligands for Nr-CAM. Further, the present invention relates, in part, to the Applicants' surprising discovery that the inhibition of Nr-CAM gene expression or the inhibition of Nr-CAM activity in transformed cells reverses the transformed phenotype.

The present invention encompasses compounds and methods for the detection of aberrant Nr-CAM gene expression or activity as a diagnostic or prognostic tool to indicate a transformed, pre-cancerous or cancerous cell phenotype. The present invention further encompasses compounds and methods for the detection of aberrant gene expression or activity as a diagnostic or prognostic tool to indicate a transformed, pre-cancerous or cancerous cell phenotype. The present invention also encompasses compounds and methods for the modulation of Nr-CAM gene expression or activity as a method of treating or preventing a transformed, pre-cancerous or cancerous cell phenotype. In this regard, the present invention provides nucleotide sequences of Nr-CAM genes, and amino acid sequences of their encoded proteins. The invention further provides fragments and other derivatives, and analogs, of Nr-CAM proteins. Nucleic acids encoding such fragments or derivatives are also within the scope of the invention. The invention provides Nr-CAM nucleic acids and their encoded proteins of humans and related genes (homologs) in other species. In specific embodiments, the Nr-CAM nucleic acids and proteins are from vertebrates, or more particularly, mammals. In a preferred embodiment of the invention, the Nr-CAM nucleic acids and proteins are of human origin. Production of the foregoing nucleic acids, proteins and derivatives, e.g., by recombinant methods, is provided.

Nr-CAM is a gene identified by the method of the invention, that is expressed at high levels in glioblastoma multiforme tissue as well as certain others forms of tumors and cancers.

The invention also provides Nr-CAM derivatives and analogs of the invention which are functionally active, i.e., they are capable of displaying one or more functional activities described herein associated with a full-length (wild-type) Nr-CAM protein. Such functional activities include, but are not limited to, antigenicity, i.e., ability to bind (or compete with Nr-CAM for binding) to an anti-Nr-CAM antibody, immunogenicity, i.e., ability to generate antibody which binds to Nr-CAM, and ability to bind (or compete with Nr-CAM for binding) to a ligand for Nr-CAM. The invention further provides fragments (and derivatives and analogs thereof) of Nr-CAM which comprise one or more domains of the Nr-CAM protein. Antibodies to Nr-CAM, its derivatives and analogs, are additionally provided.

The present invention also provides therapeutic and diagnostic methods and compositions based on Nr-CAM proteins and nucleic acids and anti-Nr-CAM antibodies. The invention provides for treatment of disorders of overproliferation (e.g., cancer and hyperproliferative disorders) by administering compounds that decrease Nr-CAM activity (e.g., antibodies, Nr-CAM antisense nucleic acids).

The invention also provides methods of treatment of disorders involving deficient cell proliferation or in which cell proliferation (growth) is otherwise desirable (e.g., growth deficiencies, degenerative disorders, lesions, physical trauma) by administering compounds that promote Nr-CAM function.

The present invention further provides screening assays to identify novel agents which target Nr-CAM gene or nucleic acid expression or Nr-CAM protein activity, including interaction with ligands, and, thus are potential therapeutic agents for the treatment or prevention of cell transformation, or pre-cancerous or cancerous phenotypes, i.e., tumorigenesis. The screening assays of the present invention may function to identify novel exogenous or endogenous agents that inhibit Nr-CAM expression or inhibit the interaction between Nr-CAM and its ligand. A variety of protocols and techniques may be used to identify drugs that inhibit Nr-CAM expression and/or Nr-CAM activity, and as a result inhibit Nr-CAM participation in aberrant cellular proliferative activity. Such identified agents have utility in the treatment of hosts demonstrating a cellular transformed phenotype or aberrant cellular proliferative behavior, and advantageously would be effective to treat and/or prevent tumorigenesis.

The present invention further encompasses pharmaceutical compositions containing the novel agents identified by the screening assays described herein. The invention provides therapeutic modalities and pharmaceutical compositions for the treatment of tumorigenesis and the prevention of transformed phenotypes. The therapeutic modalities of the present invention further encompass combination therapies in which an agent which inhibits Nr-CAM expression and/or activity, and at least one other therapeutic agent, e.g., a chemotherapeutic agent, are administered either concurrently, e.g., as an admixture, separately but simultaneously or concurrently, or sequentially.

The novel therapeutic combinations of the present invention provide a means of treatment which may not only reduce the effective dose of either drug required for anti-transformation or antitumorigenesis, thereby reducing toxicity, but may improve the absolute therapeutic effect as a result of attacking aberrant cellular proliferation through a variety of mechanisms.

The invention is illustrated by way of examples infra which disclose, inter alia, the isolation and characterization of Nr-CAM, and patterns of expression of Nr-CAM in certain tumors (see Section 6).

For clarity of disclosure, and not by way of limitation, the detailed description of the invention is divided into the subsections which follow.

5.1. Identification of Role of Nr-CAM in Transformation

The present invention relates to a novel role of Nr-CAM in the promotion of cell transformation and tumorigenesis. In particular, the present invention relates to the Applicants' findings that (a) Nr-CAM is highly over-expressed in glioblastoma multiforme tumor tissue and is over-expressed in a number of other primary tumors; and (b) over-expression of Nr-CAM in the anti-sense orientation results in decreased cellular proliferation and colony formation of glioblastoma cells in soft agar.

The present invention further relates to the Applicants' findings that Nr-CAM is over-expressed in several brain tumor derived cell lines and primary brain tumor tissues, including astrocytoma grade IV, glioma, glioblastoma and neuroectodermal human tumor cell lines compared to NBT. Low or no expression of hNr-CAM was observed in cell lines derived from astrocytoma III, medulloblastoma, neuroblastoma and NBT. Further, Nr-CAM was found to be expressed at high levels in melanoma G361, lymphoblastic leukemia cell lines, and Burkitt's lymphoma cell lines. A low level of hNr-CAM expression was observed in colorectal adenocarcinoma, lung carcinoma, pro-myelocytic leukemia HeLa cell S3, and chronic myelogenous leukemia.

The present invention relates to the role of Nr-CAM in promotion of cell transformation and tumorigenesis, and provides methods including the use of Nr-CAM nucleic acids and nucleic acids which hybridize or complement Nr-CAM nucleic acids, as diagnostic and prognostic tools for the detection of transformed, pre-cancerous and cancerous phenotypes. The present invention provides methods for use of Nr-CAM nucleic acids and those which complement and/or hybridize to nucleic acid sequences which encode Nr-CAM as therapeutics to treat, inhibit or prevent transformed, pre-cancerous and cancerous phenotypes. In particular, the invention provides compositions comprising nucleic acid sequences which inhibit Nr-CAM expression as therapeutics to treat or prevent transformed, pre-cancerous, and cancerous phenotypes.

5.2. The Production of Nr-CAM Nucleic Acids, Polypeptides and Antibodies as Diagnostics, Therapeutics and Components for Screening Assays The present invention encompasses the use of agents for the detection of aberrant Nr-CAM gene expression as diagnostic or prognostic tools to detect a transformed phenotype, pre-cancerous or cancerous condition. Diagnostic or prognostic tools which may be used in accordance with the resent invention include, but are not limited to, (a) nucleic acids which hybridize or are complementary to the Nr-CAM nucleotide sequence; (b) polypeptides, peptide fragments or synthetic molecules which bind to the Nr-CAM ligand binding domain; and (c) antibodies which bind to Nr-CAM.

The present invention relates to the use of agents which inhibit Nr-CAM expression and/or protein activity as therapeutics for the treatment and/or prevention of a transformed or pre-cancerous phenotype, or cancer or tumorigenesis. Therapeutic agents which may be used in accordance with the present invention include, but are not limited to, (a) nucleic acids which inhibit Nr-CAM gene expression, e.g., antisense molecules, ribozymes or triple helix molecules complementary to Nr-CAM; (b) polypeptides, peptides, antibodies, small organic molecules or synthetic molecules which inhibit Nr-CAM activity or prevent Nr-CAM from binding its ligand; and (c) peptides, polypeptides, antibodies, small organic molecules or synthetic molecules which act as antagonists of Nr-CAM activity.

The present invention provides screening assays for the identification of agents which inhibit Nr-CAM gene expression and/or activity. In one embodiment of the invention, an important component of the screening assays of the present invention are nucleotide coding sequences encoding Nr-CAM proteins, polypeptides and peptides. The present invention further encompasses (a) DNA vectors that contain any of the foregoing Nr-CAM encoding sequences and/or their complements; (b) DNA expression vectors that contain any of the foregoing Nr-CAM coding sequences operatively associated with a regulatory element that directs the expression of the coding sequences in the host cell; and (c) genetically engineered host cells that contain any of the foregoing Nr-CAM coding sequences operatively associated with a regulatory element that directs the expression of the coding sequences in the host cell.

5.2.1. The Nr-CAM Nucleic Acids

The invention relates to the nucleotide sequences of Nr-CAM nucleic acids. In an embodiment, the Nr-CAM nucleic acids comprise the nucleotide sequence shown in FIG. 2A, i.e., SEQ. ID. No.: 1 or specific regions thereof. In specific embodiments, Nr-CAM nucleic acids comprise the cDNA sequences of SEQ. ID. NO.: 5, or the coding regions thereof, or nucleotide sequences acids encoding a Nr-CAM protein (e.g., a protein having the sequence shown in FIG. 2B, i.e., SEQ. ID. NO.: 2) or a fragment thereof. Nucleic acids of the present invention can be single or double stranded. The invention also relates to nucleic acids hybridizable to or complementary to the foregoing sequences. In specific aspects, nucleic acids are provided which comprise a sequence complementary to at least 10, 25, 50, 100, 200, or 250 contiguous nucleotides of a Nr-CAM gene. In a specific embodiment, a nucleic acid which is hybridizable to a Nr-CAM nucleic acid (e.g., having sequence SEQ. ID. NO.: 1), or to a nucleic acid encoding a Nr-CAM derivative, under conditions of low stringency is provided.

By way of example and not limitation, procedures using such conditions of low stringency are as follows (see also Shilo and Weinberg, 1981, Proc. Natl. Acad. Sci. USA 78:6789–6792): Filters containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5–20×10$^6$ cpm $^{32}$P-labeled probe is used. Filters are incubated in hybridization mixture for 18–20 h at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography. If necessary, filters are washed for a third time at 65–68° C. and re-exposed to film. Other conditions of low stringency which may be used are well known in the art (e.g., as employed for cross-species hybridizations).

In another specific embodiment, a nucleic acid which is hybridizable to a Nr-CAM nucleic acid under conditions of high stringency is provided. By way of example and not limitation, procedures using such conditions of high stringency are as follows: Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C. in prehybridization mixture containing 100 µg/ml denatured salmon sperm DNA and 5–20×10$^6$ cpm of $^{32}$P-labeled probe. Washing of filters is done at 37° C. for 1 h in a solution containing 2×SSC, 0.01% PVP, 0.01% Ficoll, and 0.01% BSA. This is followed by a wash in 0.1×SSC at 50° C. for 45 min before autoradiography. Other conditions of high stringency which may be used are well known in the art.

In another specific embodiment, a nucleic acid which is hybridizable to a Nr-CAM nucleic acid under conditions of moderate stringency is provided.

Various other stringency conditions which promote nucleic acid hybridization can be used. For example, hybridization in 6×SSC at about 45° C., followed by washing in 2×SSC at 50° C. may be used. Alternatively, the salt concentration in the wash step can range from low stringency of about 5×SSC at 50° C., to moderate stringency of about 2×SSC at 50° C., to high stringency of about 0.2×SSC at 50° C. In addition, the temperature of the wash step can be increased from low stringency conditions at room temperature, to moderately stringent conditions at about 42° C., to high stringency conditions at about 65° C. Other conditions include, but are not limited to, hybridizing at 68° C. in 0.5M NaHPO$_4$ (pH7.2)/1 mM EDTA/7% SDS, or hybridization in 50% formamide/0.25M NaHPO$_4$ (pH 7.2)/0.25 M NaCl/1 mM EDTA/7% SDS; followed by washing in 40 mM NaHPO$_4$ (pH 7.2)/1 mM EDTA/5% SDS at 42° C. or in 40 mM NaHPO$_4$ (pH7.2) 1 mM EDTA/1% SDS at 50° C. Both temperature and salt may be varied, or alternatively, one or the other variable may remain constant while the other is changed.

Low, moderate and high stringency conditions are well known to those of skill in the art, and will vary predictably depending on the base composition of the particular nucleic acid sequence and on the specific organism from which the nucleic acid sequence is derived. For guidance regarding such conditions see, for example, Sambrook et al., 1989, Molecular Cloning, A Laboratory Manual, Second Edition, Cold Spring Harbor Press, N.Y., pp. 9.47–9.57; and Ausubel et al., 1989, Current Protocols in Molecular Biology, Green Publishing Associates and Wiley Interscience, N.Y.

The invention also encompasses nucleic acids having at least 60%, 70%, 75%, 80%, 90%, 95% or greater sequence identity when compared to a portion of identical-sized hNr-CAM sequence shown in FIG. 2A or when compared to said sequence when the alignment or comparison is conducted by a computer homology programmer search aligorithm known in the art.

By way of example and not limitation, useful computer homology programs include the following: Basic Local Alignment Search Tool (BLAST) (www.ncbi.nlm.nih.gov) (Altschul et al., 1990, J. of Molec. Biol., 215:403–410, "The BLAST Algorithm"; FASTA (also TFASTA) (see, Pearson et al., 1988, Proc. Nat'l Acad. Sci. USA 85:2444–2448) and CLUSTALW (see, Higgins et al., 1996, Methods Enzymol 266:383–402).

Altschul et al., 1997, Nuc. Acids Res. 25:3389–3402) describe BLAST, a heuristic search algorithm tailored to searching for sequence similarity which ascribes significance using the statistical methods of Karlin and Altschul 1990, Proc. Nat'l Acad. Sci. USA, 87:2264–68; 1993, Proc. Nat'l Acad. Sci. USA 90:5873–77. Five specific BLAST programs perform the following tasks:

1) The BLASTP program compares an amino acid query sequence against a protein sequence database.

2) The BLASTN program compares a nucleotide query sequence against a nucleotide sequence database.

3) The BLASTX program compares the six-frame conceptual translation products of a nucleotide query sequence (both strands) against a protein sequence database.

4) The TBLASTN program compares a protein query sequence against a nucleotide sequence database translated in all six reading frames (both strands).

5) The TBLASTX program compares the six-frame translations of a nucleotide query sequence against the six-frame translations of a nucleotide sequence database.

As will be understood by those skilled in the art, the TBLASTN program is particularly useful to identify nucleic acids with a desired percent identity and the BLASTP program is particularly useful to identify amino acid sequences with a desired percent identity.

Smith-Waterman (database: European Bioinformatics Institute wwwz.ebi.ac.uk/bic_sw/) (Smith-Waterman, 1981, J. of Molec. Biol., 147:195–197) is a mathematically rigorous algorithm for sequence alignments.

FASTA (see Pearson et al., 1988, Proc. Nat'l Acad. Sci. USA, 85:2444–2448) is a heuristic approximation to the Smith-Waterman algorithm. For a general discussion of the procedure and benefits of the BLAST, Smith-Waterman and FASTA algorithms see Nicholas et al., 1998, "A Tutorial on Searching Sequence Databases and Sequence Scoring Methods" (www.psc.edu) and references cited therein.

Nucleic acids encoding derivatives and analogs of Nr-CAM proteins (see Sections 5.2.2), and Nr-CAM antisense nucleic acids are additionally provided. As is readily apparent, as used herein, a "nucleic acid encoding a fragment or portion of a Nr-CAM protein" shall be construed as referring to a nucleic acid encoding only the recited fragment or portion of the Nr-CAM protein and not the other contiguous portions of the Nr-CAM protein as a continuous sequence.

Fragments of Nr-CAM nucleic acids comprising regions conserved between other Nr-CAM nucleic acids, of the same or different species, are also provided. Nucleic acids encoding one or more Nr-CAM domains are provided.

Specific embodiments for the cloning of a Nr-CAM gene, presented as a particular example but not by way of limitation, follow:

For expression cloning (a technique commonly known in the art), an expression library is constructed by methods known in the art. For example, mRNA (e.g., human) is isolated, cDNA is made and ligated into an expression vector (e.g., a bacteriophage derivative) such that it is capable of being expressed by the host cell into which it is then introduced. Various screening assays can then be used to select for the expressed Nr-CAM product. In one embodiment, anti-Nr-CAM antibodies can be used for selection.

In another embodiment, polymerase chain reaction (PCR) is used to amplify the desired sequence in a genomic or cDNA library, prior to selection. Oligonucleotide primers representing known Nr-CAM sequences can be used as primers in PCR. In a preferred aspect, the oligonucleotide primers represent at least part of the Nr-CAM sequence presented in FIG. 2A. The synthetic oligonucleotides may be utilized as primers to amplify by PCR sequences from a source (RNA or DNA), preferably a cDNA library, of potential interest. PCR can be carried out, e.g., by use of a Perkin-Elmer Cetus thermal cycler and Taq polymerase (Gene Amp™). The DNA being amplified can include mRNA, cDNA, or genomic DNA from any eukaryotic species. One can choose to synthesize several different degenerate primers, for use in the PCR reactions. It is also possible to vary the stringency of hybridization conditions used in priming the PCR reactions, to allow for greater or lesser degrees of nucleotide sequence similarity between the known Nr-CAM nucleotide sequence and the nucleic acid homolog being isolated. For cross species hybridization, low stringency conditions are preferred. For same species hybridization, moderately stringent conditions are preferred. After successful amplification of a segment of a Nr-CAM homolog, that segment may be molecularly cloned and sequenced, and utilized as a probe to isolate a complete cDNA or genomic clone. This, in turn, will permit the determination of the gene's complete nucleotide sequence, the analysis of its expression, and the production of its protein product for functional analysis, as described infra. In this fashion, additional genes encoding Nr-CAM proteins and Nr-CAM analogs may be identified.

The above-methods are not meant to limit the following general description of methods by which clones of Nr-CAM may be obtained.

Any eukaryotic cell potentially can serve as the nucleic acid source for the molecular cloning of the Nr-CAM gene. The nucleic acid sequences encoding Nr-CAM can be isolated from vertebrate sources, including mammalian sources, such as porcine, bovine, feline, and equine, canine, human, as well as additional primate sources, avian, reptilian, amphibian, piscine, etc. sources, non-vertebrate sources such as insects, from plants, etc. The DNA may be obtained by standard procedures known in the art from cloned DNA (e.g., a DNA "library"), by chemical synthesis, by cDNA cloning, or by the cloning of genomic DNA, or fragments thereof, purified from the desired cell. (See, for example, Sambrook et al., 1989, Molecular Cloning, A Laboratory Manual, 2d Ed., Cold Spring Harbor Laboratory Press, Cold Spring Harbor, N.Y.; Glover, D. M. (ed.), 1985, DNA Cloning: A Practical Approach, MRL Press, Ltd., Oxford, U.K. Vol. I, II.) Clones derived from genomic DNA may contain regulatory and intron DNA regions in addition to coding regions; clones derived from cDNA will contain only exon sequences. Whatever the source, the gene should be molecularly cloned into a suitable vector for propagation of the gene.

In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the desired gene may be accomplished in a number of ways. For example, if an amount of a portion of a Nr-CAM (of any species) gene or its specific RNA, or a fragment thereof (see Section 5.6), is available and can be purified and labeled, the generated DNA fragments may be screened by nucleic acid hybridization to the labeled probe (Benton and Davis, 1977, Science 196:180; Grunstein and Hogness, 1975, Proc. Natl. Acad. Sci. U.S.A. 72:3961). Those DNA fragments with substantial homology to the probe will hybridize. It is also possible to identify the appropriate fragment by restriction enzyme digestion(s) and comparison of fragment sizes with those expected according to a known restriction map if such is available. Further selection can be carried out on the basis of the properties of the gene. Alternatively, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isoelectric focusing behavior, proteolytic digestion maps, promotion of cell proliferation activity, substrate binding activity, or antigenic properties of Nr-CAM. If an antibody to Nr-CAM is available, the Nr-CAM protein may be identified by binding of labeled antibody to the putatively Nr-CAM synthesizing clones, in an ELISA (enzyme-linked immunosorbent assay)-type procedure.

The Nr-CAM gene can also be identified by mRNA selection by nucleic acid hybridization followed by in vitro translation. In this procedure, fragments are used to isolate complementary mRNAs by hybridization. Such DNA fragments may represent available, purified Nr-CAM DNA of another species (e.g., human, mouse, etc.). Immunoprecipitation analysis or functional assays (e.g., aggregation ability in vitro; binding to receptor; see infra) of the in vitro translation products of the isolated products of the isolated mRNAs identifies the mRNA and, therefore, the complementary DNA fragments that contain the desired sequences. In addition, specific mRNAs may be selected by adsorption of polysomes isolated from cells to immobilized antibodies specifically directed against Nr-CAM protein. A radiolabelled Nr-CAM cDNA can be synthesized using the selected mRNA (from the adsorbed polysomes) as a template. The radiolabelled mRNA or cDNA may then be used as a probe to identify the Nr-CAM DNA fragments from among other genomic DNA fragments.

Alternatives to isolating the Nr-CAM genomic DNA include, but are not limited to, chemically synthesizing the gene sequence itself from a known sequence or making cDNA to the mRNA which encodes the Nr-CAM protein. For example, RNA for cDNA cloning of the Nr-CAM gene can be isolated from cells which express Nr-CAM. Other methods are possible and within the scope of the invention.

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Such vectors include, but are not limited to, bacteriophages such as lambda derivatives, or plasmids such as pBR322 or pUC plasmid derivatives or the Bluescript vector (Stratagene). The insertion into a cloning vectorcan, for example, can be accomplished by ligating the DNA fragment into a cloning vector, which has complementarycohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termii; these ligated linkers may comprise specific chemically synthesized oligonucleotides encoding restriction endonuclease recognition sequences. In an alternative method, the cleaved vector and Nr-CAM gene may be modified by homopolymeric tailing. Recombinant molecules can be introduced into host cells via transformation, transfection, infection, electroporation, etc., so that many copies of the gene sequence are generated.

In an alternative method, the desired gene may be identified and isolated after insertion into a suitable cloning vector in a "shot gun" approach. Enrichment for the desired gene, for example, by size fractionization, can be done before insertion into the cloning vector.

In specific embodiments, transformation of host cells with recombinant DNA molecules that incorporate the isolated Nr-CAM gene, cDNA, or synthesized DNA sequence enables generation of multiple copies of the gene. Thus, the gene may be obtained in large quantities by growing transformants, isolating the recombinant DNA molecules from the transformants and, when necessary, retrieving the inserted gene from the isolated recombinant DNA.

The Nr-CAM sequences provided by the present invention include those nucleotide sequences encoding substantially the same amino acid sequences as found in native Nr-CAM proteins, and those encoded amino acid sequences with functionally equivalent amino acids, as well as those encoding other Nr-CAM derivatives or analogs, as described in Section 5.2.5 infra for Nr-CAM derivatives and analogs.

The Nr-CAM sequences provided by the present invention include those that encode Nr-CAM mutants that are constitutively expressed.

5.2.2. Expression of Nr-CAM Nucleic Acids

The nucleotide sequence coding for a Nr-CAM protein or a functionally active analog or fragment or other derivative thereof, can be inserted into an appropriate expression vector, i.e., a vector which contains the necessary elements for the transcription and translation of the inserted protein-coding sequence. The necessary transcriptional and translational signals can also be supplied by the native Nr-CAM gene and/or its flanking regions. A variety of host-vector systems may be utilized to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used. In specific embodiments, the human Nr-CAM gene is expressed, or a sequence encoding a functionally active portion of human Nr-CAM. In yet another embodiment, a fragment of Nr-CAM comprising a domain of the Nr-CAM protein is expressed.

Any of the methods previously described for the insertion of DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinants (genetic recombination). Expression of nucleic acid sequence encoding a Nr-CAM protein or peptide fragment may be regulated by a second nucleic acid sequence so that the Nr-CAM protein or peptide is expressed in a host transformed with the recombinant DNA molecule. For example, expression of a Nr-CAM protein may be controlled by any promoter/enhancer element known in the art. Promoters which may be used to control Nr-CAM expression include, but are not limited to, the SV40 early promoter region (Bernoist and Chambon, 1981, Nature 290:304–310), the promoter contained in the 3' long terminal repeat of Rous sarcoma virus (Yamamoto, et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42); prokaryotic expression vectors such as the β-lactamase promoter (Villa-Kamaroff, et al., 1978, Proc. Natl. Acad. Sci. U.S.A. 75:3727–3731), or the tac promoter (DeBoer, et al., 1983, Proc. Natl. Acad. Sci. U.S.A. 80:21–25); see also "Useful proteins from recombinant bacteria" in Scientific American, 1980, 242:74–94; plant expression vectors comprising the nopaline synthetase promoter region (Herrera-Estrella et al., 1983, Nature 303:209–213) or the cauliflower mosaic virus 35S RNA promoter (Gardner, et al., 1981, Nucl. Acids Res. 9:2871), and the promoter of the photosynthetic enzyme ribulose biphosphate carboxylase (Herrera-Estrella et al., 1984, Nature 310:115–120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58; alpha 1-antitrypsin gene control region which is active in the liver (Kelsey et al., 1987, Genes and Devel. 1:161–171), beta-globin gene control region which is active in myeloid cells (Mogram et al., 1985, Nature 315:338–340; Kollias et al., 1986, Cell 46:89–94; myelin basic protein gene control region which is active in oligodendrocyte cells in the brain (Readhead et al., 1987, Cell 48:703–712); myosin light chain-2 gene control region which is active in skeletal muscle (Sani, 1985, Nature 314:283–286), and gonadotropic releasing hormone gene control region which is active in the hypothalamus (Mason et al., 1986, Science 234:1372–1378).

In a specific embodiment, a vector is used that comprises a promoter operably linked to a Nr-CAM-encoding nucleic acid, one or more origins of replication, and, optionally, one or more selectable markers (e.g., an antibiotic resistance gene).

In a specific embodiment, an expression construct is made by subcloning a Nr-CAM coding sequence into the EcoRI restriction site of each of the three PGEX vectors (Glutathione S-Transferase expression vectors; Smith and Johnson, 1988, Gene 7:31–40). This allows for the expression of the Nr-CAM protein product from the subclone in the correct reading frame.

In another specific embodiment, the promoter that is operably linked to the hNr-CAM gene is not the native hNr-CAM gene promoter (i.e., it is a heterologous promoter).

Expression vectors containing Nr-CAM gene inserts can be identified by three general approaches: (a) nucleic acid hybridization, (b) presence or absence of "marker" gene functions, and (c) expression of inserted sequences. In the first approach, the presence of a Nr-CAM gene inserted in an expression vector can be detected by nucleic acid hybridization using probes comprising sequences that are homologous to an inserted Nr-CAM gene. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of a Nr-CAM gene in the vector. For example, if the Nr-CAM gene is inserted within the marker gene sequence of the vector, recombinants containing the Nr-CAM insert can be identified by the absence of the marker gene function. In the third approach, recombinant expression vectors can be identified by assaying the Nr-CAM product expressed by the recombinant. Such assays can be based, for example, on the physical or functional properties of the Nr-CAM protein in in vitro assay systems, e.g., binding with anti-Nr-CAM antibody, promotion of cell proliferation.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered Nr-CAM protein may be controlled. Furthermore, different host cells have characteristic and specific mechanisms for the translational and post-translational processing and modification (e.g., glycosylation, phosphorylation of proteins. Appropriate cell lines or host systems can be chosen to ensure the desired modification and processing of the foreign protein expressed. For example, expression in a bacterial system can be used to produce an unglycosylated core protein product. Expression in yeast will produce a glycosylated product. Expression in mammalian cells can be used to ensure "native" glycosylation of a heterologous protein. Furthermore, different vector/host expression systems may effect processing reactions to different extents.

In other specific embodiments, the Nr-CAM protein, fragment, analog, or derivative may be expressed as a fusion, or chimeric protein product (comprising the protein, fragment, analog, or derivative joined via a peptide bond to a heterologous protein sequence (of a different protein)). Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer.

Both cDNA and genomic sequences can be cloned and expressed.

5.2.3. Identification and Purification of the Nr-CAM Products

In particular aspects, the invention provides amino acid sequences of Nr-CAM, preferably human Nr-CAM, and fragments and derivatives thereof which comprise an antigenic determinant (i.e., can be recognized by an antibody) or which are otherwise functionally active, as well as nucleic acid sequences encoding the foregoing. "Functionally active" Nr-CAM material as used herein refers to that material displaying one or more functional activities associated with a full-length (wild-type) Nr-CAM protein, e.g., promotion of cell proliferation, binding to a Nr-CAM substrate or Nr-CAM binding partner, antigenicity (binding to an anti-Nr-CAM antibody), immunogenicity, etc.

In other specific embodiments, the invention provides fragments of a Nr-CAM protein consisting of at least 6 amino acids, 10 amino acids, 50 amino acids, or of at least 75 amino acids of SEQ. ID. No.: 2. In other embodiments, the invention provides proteins comprising, having, or consisting essentially of a sequence of amino acids 100% identical with SEQ. ID. NO.: 2, SEQ. ID. NO.: 2 or a protein encoded by SEQ. ID. NO.: 1, or any combination of the foregoing. Fragments or proteins comprising such sequences are particularly advantageously used for immunotherapy as described below. Fragments, or proteins comprising fragments, lacking some or all of the foregoing regions of a Nr-CAM protein are also provided. Nucleic acids encoding the foregoing are provided. In specific embodiments, the foregoing proteins or fragments are not more than 25, 50 or 100 contiguous amino acids.

Once a recombinant which expresses the Nr-CAM gene sequence is identified, the gene product can be analyzed. This is achieved by assays based on the physical or functional properties of the product, including radioactive labelling of the product followed by analysis by gel electrophoresis, immunoassay, etc.

Once the Nr-CAM protein is identified, it may be isolated and/or purified by standard methods including chromatography (e.g., ion exchange, affinity, and sizing column chromatography), centrifugation, differential solubility, or by any other standard technique for the purification of proteins. The functional properties may be evaluated using any suitable assay (see Section 5.3).

Alternatively, once a Nr-CAM protein produced by a recombinant is identified, the amino acid sequence of the protein can be deduced from the nucleotide sequence of the chimeric gene contained in the recombinant. As a result, the protein can be synthesized by standard chemical methods known in the art (e.g., see Hunkapiller, M., et al., 1984, Nature 310:105–111).

In another alternate embodiment, native Nr-CAM proteins can be purified from natural sources, by standard methods such as those described above (e.g., immunoaffinity purification).

In a specific embodiment of the present invention, such Nr-CAM proteins, whether produced by recombinant DNA techniques or by chemical synthetic methods or by purification of native proteins, include but are not limited to those containing, as a primary amino acid sequence, all or part of the amino acid sequence substantially, as well as fragments and other derivatives, and analogs as shown in FIG. 2B (SEQ. ID. NO.: 2) thereof, including proteins homologous thereto.

5.2.4. Antibodies and Immune Cells to Nr-CAM

5.2.4.1. Generation of Antibodies to Nr-CAM Proteins and Derivatives Thereof According to the invention, Nr-CAM protein, its fragments or other derivatives, or analogs thereof, may be used as an immunogen to generate antibodies which immunospecifically bind such an immunogen. Such antibodies include but are not limited to polyclonal, monoclonal, chimeric, single chain, Fab fragments, and an Fab expression library. In a specific embodiment, antibodies to a human Nr-CAM protein are produced. In another embodiment, antibodies to a domain of a Nr-CAM protein are produced. In a specific embodiment, fragments of a Nr-CAM protein identified as hydrophilic are used as immunogens for antibody production.

In another specific embodiment, the antibody to a human Nr-CAM protein is a bispecific antibody (see generally, e.g. Fanger and Drakeman, 1995, *Drug News and Perspectives* 8: 133–137). Such a bispecific antibody is genetically engineered to recognize both (1) a human Nr-CAM epitope and (2) one of a variety of "trigger" molecules, e.g. Fc receptors on myeloid cells, and CD3 and CD2 on T cells, that have been identified as being able to cause a cytotoxic T-cell to destroy a particular target. Such bispecific antibodies can be prepared either by chemical conjugation, hybridoma, or recombinant molecular biology techniques known to the skilled artisan.

Various procedures known in the art may be used for the production of polyclonal antibodies to a Nr-CAM protein or derivative or analog. In a particular embodiment, rabbit polyclonal antibodies to an epitope of a Nr-CAM protein, or a subsequence thereof, can be obtained. For the production of antibody, various host animals can be immunized by injection with the native Nr-CAM protein, or a synthetic version, or derivative (e.g., fragment) thereof, including but not limited to rabbits, mice, rats, etc. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum.

For preparation of monoclonal antibodies directed toward a Nr-CAM protein sequence or analog thereof, any technique which provides for the production of antibody molecules by continuous cell lines in culture may be used. For example, the hybridoma technique originally developed by Kohler and Milstein (1975, Nature 256:495–497), as well as the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77–96). In an additional embodiment of the invention, monoclonal antibodies can be produced in germ-free animals utilizing technology described in PCT/US90/02545. According to the invention, human antibodies may be used and can be obtained by using human hybridomas (Cote et al., 1983, Proc. Natl. Acad. Sci. U.S.A. 80:2026–2030) or by transforming human B cells with EBV virus in vitro (Cole et al., 1985, in *Monoclonal Antibodies and Cancer Therapy*, Alan R. Liss, pp. 77–96). In fact, according to the invention, techniques developed for the production of "chimeric antibodies" (Morrison et al., 1984, PROC. NATL. ACAD. SCI. U.S.A. 81:6851–6855; Neuberger et al., 1984, Nature 312: 604–608; Takeda et al., 1985, Nature 314:452–454) by splicing the genes from a mouse antibody molecule specific for Nr-CAM together with genes from a human antibody molecule of appropriate biological activity can be used; such antibodies are within the scope of this invention.

According to the invention, techniques described for the production of single chain antibodies (U.S. Pat. No. 4,946, 778) can be adapted to produce Nr-CAM-specific single chain antibodies. An additional embodiment of the invention utilizes the techniques described for the construction of Fab expression libraries (Huse et al., 1989, Science 246:1275–1281) to allow rapid and easy identification of monoclonal Fab fragments with the desired specificity for Nr-CAM proteins, derivatives, or analogs.

Antibody fragments which contain the idiotype of the molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, the Fab fragments which can be generated by treating the antibody molecule with papain and a reducing agent, and Fv fragments.

In the production of antibodies, screening for the desired antibody can be accomplished by techniques known in the art, e.g. ELISA (enzyme-linked immunosorbent assay). For example, to select antibodies which recognize a specific domain of a Nr-CAM protein, one may assay generated hybridomas for a product which binds to a Nr-CAM fragment containing such domain. For selection of an antibody that specifically binds a first Nr-CAM homolog but which does not specifically bind a different Nr-CAM homolog, one can select on the basis of positive binding to the first Nr-CAM homolog and a lack of binding to the second Nr-CAM homolog.

Antibodies specific to a domain of a Nr-CAM protein are also provided.

The foregoing antibodies can be used in methods known in the art relating to the localization and activity of the Nr-CAM protein sequences of the invention, e.g., for imaging these proteins, measuring levels thereof in appropriate physiological samples, in diagnostic methods, etc.

In another embodiment of the invention (see infra), anti-Nr-CAM antibodies and fragments thereof containing the binding domain are Therapeutics.

Antibodies and antigen-binding antibody fragments may also be conjugated to a heterologous protein or peptide by chemical conjugation or recombinant DNA technology. The resultant chimeric protein possesses the antigen-binding specificity of the antibody and the function of the heterologous protein. For example, a polynucleotide encoding the antigen binding region of an antibody specific for the extracellular domain of Nr-CAM can be genetically fused to a coding sequence for the zeta chain of the T cell receptor. After expressing this construct in T cells, the T cells are expanded ex vivo and infused into a brain cancer patient. T cells expressing this chimeric protein are specifically directed to tumors that express Nr-CAM as a result of the antibody binding specificity and cause tumor cell killing. Alternatively, an antibody is fused to a protein which induces migration of leukocytes or has an affinity to attract other compounds to a tumor cite. A specific protein of this type is streptavidin. The binding of a streptavidin conjugated antibody to a tumor cell can be followed by the addition of a biotinylated drug, toxin or radioisotope to cause tumor specific killing.

Kits for use with such in vitro tumor localization and therapy methods containing the monoclonal antibodies (or fragments thereof) conjugated to any of the above types of substances can be prepared. The components of the kits can be packaged either in aqueous medium or in lyophilized form. When the monoclonal antibodies (or fragments thereof) are used in the kits in the form of conjugates in which a label or a therapeutic moiety is attached, such as a radioactive metal ion or a therapeutic drug moiety, the components of such conjugates can be supplied either in fully conjugated form, in the form of intermediates or as separate moieties to be conjugated by the user of the kit.

5.2.5. Nr-CAM Proteins, Derivatives and Analogs

The invention further encompasses compositions comprising Nr-CAM proteins, and derivatives (including but not limited to fragments) and analogs of Nr-CAM proteins, in particular, those derivatives which act as antagonists of Nr-CAM activity. Nucleic acids encoding Nr-CAM protein derivatives and protein analogs are also provided. In one embodiment, the Nr-CAM proteins are encoded by the Nr-CAM nucleic acids described in Section 5.2.1. supra. In particular aspects, the proteins, derivatives, or analogs are of Nr-CAM proteins of animals, e.g., fly, frog, mouse, rat, pig, cow, dog, monkey, human, or of plants.

The production and use of derivatives and analogs related to Nr-CAM are within the scope of the present invention. In a specific embodiment, the derivative or analog is functionally active, i.e., capable of exhibiting one or more functional activities associated with a full-length, wild-type Nr-CAM protein. As one example, such derivatives or analogs which have the desired immunogenicity or antigenicity can be used, for example, in immunoassays, for immunization, for inhibition of Nr-CAM activity, etc. Derivatives or analogs that retain, or alternatively lack or inhibit, a desired Nr-CAM property of interest (e.g., binding to Nr-CAM binding partner, promotion of cell proliferation), can be used as inducers, or inhibitors, respectively, of such property and its physiological correlates. A specific embodiment relates to a Nr-CAM fragment that can be bound by an anti-Nr-CAM antibody. Derivatives or analogs of Nr-CAM can be tested for the desired activity by procedures known in the art, including but not limited to the assays described in Sections 5.3 and 5.5.

In particular, Nr-CAM derivatives can be made by altering Nr-CAM sequences by substitutions, additions or deletions that provide for functionally equivalent molecules. Due to the degeneracy of nucleotide coding sequences, other DNA sequences which encode substantially the same amino acid sequence as a Nr-CAM gene may be used in the practice of the present invention. These include but are not limited to nucleotide sequences comprising all or portions of Nr-CAM genes which are altered by the substitution of different codons that encode a functionally equivalent amino acid residue within the sequence, thus producing a silent change. Likewise, the Nr-CAM derivatives of the invention include, but are not limited to, those containing, as a primary amino acid sequence, all or part of the amino acid sequence of a Nr-CAM protein including altered sequences in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

In a specific embodiment of the invention, proteins consisting of or comprising a fragment of a Nr-CAM protein consisting of at least 10 (continuous) amino acids of the Nr-CAM protein is provided. In other embodiments, the fragment consists of at least 20 or 50 amino acids of the Nr-CAM protein. In specific embodiments, such fragments are not larger than 35, 100 or 200 amino acids. Derivatives or analogs of Nr-CAM include but are not limited to those molecules comprising regions that are substantially homologous to Nr-CAM or fragments thereof (e.g., in various embodiments, at least 60% or 70% or 80% or 90% or 95% identity over an amino acid sequence of identical size or when compared to an aligned sequence in which the alignment is done by a computer homology program known in the art) or whose encoding nucleic acid is capable of hybridizing to a coding Nr-CAM sequence, under stringent, moderately stringent, or nonstringent conditions. See, supra Section 5.2.1. for useful computer programs for sequence comparisons.

The Nr-CAM derivatives and analogs of the invention can be produced by various methods known in the art. The manipulations which result in their production can occur at the gene or protein level. For example, the cloned Nr-CAM gene sequence can be modified by any of numerous strategies known in the art (Sambrook et al., 1989, Molecular Cloning, A Laboratory Manual, 2d Ed., Cold Spring Harbor Laboratory Press, Cold Spring Harbor, N.Y.). The sequence can be cleaved at appropriate sites with restriction endonuclease(s), followed by further enzymatic modification if desired, isolated, and ligated in vitro. In the production of the gene encoding a derivative or analog of Nr-CAM, care should be taken to ensure that the modified gene remains within the same translational reading frame as Nr-CAM, uninterrupted by translational stop signals, in the gene region where the desired Nr-CAM activity is encoded.

Additionally, the Nr-CAM-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, chemical mutagenesis, in vitro site-directed mutagenesis (Hutchinson, C., et al., 1978, J. Biol. Chem 253:6551), use of TAB® linkers (Pharmacia), etc.

Manipulations of the Nr-CAM sequence may also be made at the protein level. Included within the scope of the invention are Nr-CAM protein fragments or other derivatives or analogs which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc.

In addition, analogs and derivatives of Nr-CAM can be chemically synthesized. For example, a peptide corresponding to a portion of a Nr-CAM protein which comprises the desired domain, or which mediates the desired activity in vitro, can be synthesized by use of a peptide synthesizer. Furthermore, if desired, nonclassical amino acids or chemical amino acid analogs can be introduced as a substitution or addition into the Nr-CAM sequence. Non-classical amino acids include but are not limited to the D-isomers of the common amino acids, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general. Furthermore, the amino acid can be D (dextrorotary) or L (levorotary).

In a specific embodiment, the Nr-CAM derivative is a chimeric, or fusion, protein comprising a Nr-CAM protein or fragment thereof (preferably consisting of at least a domain or motif of the Nr-CAM protein, or at least 10 amino acids of the Nr-CAM protein) joined at its amino- or carboxy-terminus via a peptide bond to an amino acid sequence of a different protein. In one embodiment, such a chimeric protein is produced by recombinant expression of a nucleic acid encoding the protein (comprising a Nr-CAM-coding sequence joined in-frame to a coding sequence for a different protein). Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer. Chimeric genes comprising portions of Nr-CAM fused to any heterologous protein-encoding sequences may be constructed. A specific embodiment relates to a chimeric protein comprising a fragment of Nr-CAM of at least six amino acids.

In another specific embodiment, the Nr-CAM derivative is a molecule comprising a region of homology with a Nr-CAM protein. By way of example, in various embodiments, a first protein region can be considered "homologous" to a second protein region when the amino acid sequence of the first region is at least 30%, 40%, 50%, 60%, 70%, 75%, 80%, 90%, or 95% identical, when compared to any sequence in the second region of an equal number of amino acids as the number contained in the first region or when compared to an aligned sequence of the second region that has been aligned by a computer homology program known in the art. For example, a molecule can comprise one or more regions homologous to a Nr-CAM domain or a portion thereof.

Other specific embodiments of derivatives and analogs are described in the subsections below and examples sections infra.

5.3. Assays of Nr-CAM Proteins, Derivatives and Analogs

The functional activity of Nr-CAM proteins, derivatives and analogs can be assayed by various methods.

For example, in one embodiment, where one is assaying for the ability to bind or compete with wild-type Nr-CAM for binding to anti-Nr-CAM antibody, various immunoassays known in the art can be used, including but not limited to competitive and non-competitive assay systems using techniques such as radioimmunoassays, ELISA (enzyme linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labelled. Many means are known in the art for detecting binding in an immunoassay and are within the scope of the present invention.

In another embodiment, where a Nr-CAM-binding protein is identified, the binding can be assayed, e.g., by means well-known in the art. In another embodiment, physiological correlates of Nr-CAM binding to its substrates (signal transduction) can be assayed.

In addition, assays that can be used to detect or measure the ability to inhibit, or alternatively promote, cell proliferation are described herein.

Other methods will be known to the skilled artisan and are within the scope of the invention.

5.4. Diagnosis and Screening

Nr-CAM proteins, analogs, derivatives, and subsequences thereof, Nr-CAM nucleic acids (and sequences complementary thereto), anti-Nr-CAM antibodies, have uses in diagnostics. Such molecules can be used in assays, such as immunoassays, to detect, prognoses, diagnose, or monitor various conditions, diseases, and disorders affecting Nr- CAM expression, or monitor the treatment thereof. In particular, such an immunoassay is carried out by a method comprising contacting a sample derived from a patient with an anti-Nr-CAM antibody under conditions such that immunospecific binding can occur, and detecting or measuring the amount of any immunospecific binding by the antibody. In a specific aspect, such binding of antibody, in tissue sections, can be used to detect aberrant Nr-CAM localization or aberrant (e.g., high, low or absent) levels of Nr-CAM. In a specific embodiment, antibody to Nr-CAM can be used to assay in a patient tissue or serum sample for the presence of Nr-CAM where an aberrant level of Nr-CAM is an indication of a diseased condition. By "aberrant levels," is meant increased or decreased levels relative to that present, or a standard level representing that present, in an analogous sample from a portion of the body or from a subject not having the disorder. In a specific embodiment, antibody to Nr-CAM can be used to assay and screen tissues or bodily fluids including but not limited to spinal fluid and brain tissue for elevated levels of Nr-CAM expression indicative of a tumor.

The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few.

Nr-CAM genes and related nucleic acid sequences and subsequences, including complementary sequences, can also be used in hybridization assays. Nr-CAM nucleic acid sequences, or subsequences thereof comprising about at least 8 nucleotides, can be used as hybridization probes. Hybridization assays can be used to detect, prognose, diagnose, or monitor conditions, disorders, or disease states associated with aberrant changes in Nr-CAM expression and/or activity as described supra. In particular, such a hybridization assay is carried out by a method comprising contacting a sample containing nucleic acid with a nucleic acid probe capable of hybridizing to Nr-CAM DNA or RNA, under conditions such that hybridization can occur, and detecting or measuring any resulting hybridization.

In specific embodiments, diseases and disorders involving overproliferation of cells can be diagnosed, or their suspected presence can be screened for, or a predisposition to develop such disorders can be detected, by detecting increased levels of Nr-CAM protein, Nr-CAM RNA, or Nr-CAM functional activity or by detecting mutations in Nr-CAM RNA, DNA or protein (e.g., translocations in Nr-CAM nucleic acids, truncations in the Nr-CAM gene or protein, changes in nucleotide or amino acid sequence relative to wild-type Nr-CAM) that cause increased expression or activity of Nr-CAM. Such diseases and disorders include but are not limited to those tumors or tissue types mentioned in Section 6 in which Nr-CAM is overexpressed. By way of example, levels of Nr-CAM protein can be detected by immunoassay, levels of Nr-CAM RNA can be detected by hybridization assays (e.g., Northern blots, dot blots), translocations and point mutations in Nr-CAM nucleic acids can be detected by Southern blotting, RFLP analysis, PCR using primers that preferably generate a fragment spanning at least most of the Nr-CAM gene, sequencing of the Nr-CAM genomic DNA or cDNA obtained from the patient, etc.

In a preferred embodiment, levels of Nr-CAM mRNA or protein in a patient sample are detected or measured, in which increased levels indicate that the subject has, or has a predisposition to developing, a malignancy or hyperproliferative disorder; in which the increased levels are relative to the levels present in an analogous sample from a portion of the body or from a subject not having the malignancy or hyperproliferative disorder, as the case may be.

In another specific embodiment, diseases and disorders involving a deficiency in cell proliferation or in which cell proliferation is desirable for treatment, are diagnosed, or their suspected presence can be screened for, or a predisposition to develop such disorders can be detected, by detecting decreased levels of Nr-CAM protein, Nr-CAM RNA, or Nr-CAM functional activity, or by detecting mutations in Nr-CAM RNA, DNA or protein (e.g., translocations in Nr-CAM nucleic acids, truncations in the gene or protein, changes in nucleotide or amino acid sequence relative to wild-type Nr-CAM) that cause decreased expression or activity of Nr-CAM. Such diseases and disorders include but are not limited to those tumors and tissue types mentioned in Section 6 and its subsections in which Nr-CAM is overexpressed. By way of example, levels of Nr-CAM protein, levels of Nr-CAM RNA, Nr-CAM binding activity, and the presence of translocations or point mutations can be determined as described above.

In a specific embodiment, levels of Nr-CAM mRNA or protein in a patient sample are detected or measured, in which decreased levels indicate that the subject has, or has a predisposition to developing, a malignancy or hyperproliferative disorder; in which the decreased levels are relative to the levels present in an analogous sample from a portion of the body or from a subject not having the malignancy or hyperproliferative disorder, as the case may be.

Kits for diagnostic use are also provided, that comprise, in one or more containers, an anti-Nr-CAM antibody, and, optionally, a labeled binding partner to the antibody. Alternatively, the anti-Nr-CAM antibody can be labeled (with a detectable marker, e.g., a chemiluminescent, enzymatic, fluorescent, or radioactive moiety). A kit is also provided that comprises, in one or more containers, a nucleic acid probe capable of hybridizing to Nr-CAM RNA. In a specific embodiment, a kit can comprise in one or more containers a pair of primers (e.g., each in the size range of 6–30 nucleotides) that are capable of priming amplification [e.g., by polymerase chain reaction (see e.g., Innis et al., 1990, PCR Protocols, Academic Press, Inc., San Diego, Calif.), ligase chain reaction (see EP 320,308) use of Qβ replicase, cyclic probe reaction, or other methods known in the art] under appropriate reaction conditions of at least a portion of a Nr-CAM nucleic acid. A kit can optionally further comprise, in a container, a predetermined amount of a purified Nr-CAM protein or nucleic acid, e.g., for use as a standard or control.

5.5. Therapeutic Uses

The invention provides for treatment, inhibition or prevention of various diseases and disorders by administration of a therapeutic compound (termed herein "Therapeutic"). Such "Therapeutics" include but are not limited to: Nr-CAM proteins and analogs and derivatives (including fragments) thereof (e.g., as described hereinabove); antibodies thereto (as described hereinabove); nucleic acids encoding the Nr-CAM proteins, analogs, or derivatives (e.g., as described hereinabove); Nr-CAM antisense nucleic acids, and Nr-CAM agonists and antagonists. Disorders involving tumorigenesis or cell overproliferation are treated or prevented by administration of a Therapeutic that antagonizes Nr-CAM function. Disorders in which cell proliferation is deficient or is desired are treated or prevented by administration of a Therapeutic that promotes Nr-CAM function. See details in the subsections below.

Generally, it is preferred to administer a product of a species origin or species reactivity (in the case of antibodies) that is the same as that of the recipient. Thus, in a preferred embodiment, a human Nr-CAM protein, derivative, or analog, or nucleic acid, or an antibody to a human Nr-CAM protein, is therapeutically or prophylactically administered to a human patient.

Additional descriptions and sources of Therapeutics that can be used according to the invention are found in Sections 5.1 through 5.7 herein.

5.5.1. Treatment, Inhibition and Prevention of Disorders Involving Overproliferation of Cells Diseases and disorders involving cell overproliferation are treated, inhibited or prevented by administration of a Therapeutic that antagonizes (i.e., inhibits) Nr-CAM function. Examples of such a Therapeutic include but are not limited to Nr-CAM antibodies, Nr-CAM antisense nucleic acids, derivatives, or analogs that are functionally active, particularly that are active in inhibiting cell proliferation (e.g., as demonstrated in in vitro assays or in animal models or in *Drosophila*. Other Therapeutics that can be used, e.g., Nr-CAM antagonists, can be identified using in vitro assays or animal models, examples of which are described infra.

In specific embodiments, Therapeutics that inhibit Nr-CAM function are administered therapeutically (including prophylactically): (1) in diseases or disorders involving an increased (relative to normal or desired) level of Nr-CAM protein or function, for example, in patients where Nr-CAM protein is overexpressed, genetically defective, or biologically hyperactive; or (2) in diseases or disorders wherein in vitro (or in vivo) assays (see infra) indicate the utility of Nr-CAM antagonist administration. The increased level in Nr-CAM protein or function can be readily detected, e.g., by obtaining a patient tissue sample (e.g., from biopsy tissue) and assaying it in vitro for RNA or protein levels, structure and/or activity of the expressed Nr-CAM RNA or protein. Many methods standard in the art can be thus employed, including but not limited to immunoassays to detect and/or visualize Nr-CAM protein (e.g., Western blot, immunoprecipitation followed by sodium dodecyl sulfate polyacrylamide gel electrophoresis, immunocytochemistry, etc.) and/or hybridization assays to detect Nr-CAM expression by detecting and/or visualizing Nr-CAM mRNA (e.g., Northern assays, dot blots, in situ hybridization, etc.), etc.

Diseases and disorders involving cell overproliferation that can be treated, inhibited or prevented include but are not limited to malignancies, premalignant conditions (e.g., hyperplasia, metaplasia, dysplasia), benign tumors, hyperproliferative disorders, benign dysproliferative disorders, etc. Examples of these are detailed below.

5.5.1.1. Malignancies

Malignancies and related disorders that can be treated or prevented by administration of a Therapeutic that inhibits Nr-CAM function include but are not limited to those listed in Table 1 (for a review of such disorders, see Fishman et al., 1985, Medicine, 2d Ed., J.B. Lippincott Co., Philadelphia).

TABLE 1

MALIGNANCIES AND RELATED DISORDERS

Leukemia
  acute leukemia
    acute lymphocytic leukemia
    acute lymphoblastic leukemia
    acute myelocytic leukemia
      myeloblastic
      myelogenous
      promyelocytic
      myelomonocytic
      monocytic
      erythroleukemia
  chronic leukemia
    chronic myelocytic (granulocytic) leukemia
    chronic myelogenous leukemia
    chronic lymphocytic leukemia
Polycythemia vera
Lymphoma
  Hodgkin's disease
  non-Hodgkin's disease
Multiple myeloma
Waldenström's macroglobulinemia
Heavy chain disease
Solid tumors
  sarcomas and carcinomas
    adenocarcinoma
    fibrosarcoma
    myxosarcoma
    liposarcoma
    chondrosarcoma
    osteogenic sarcoma
    chordoma
    angiosarcoma
    endotheliosarcoma
    lymphangiosarcoma
    lymphangioendotheliosarcoma
    synovioma
    mesothelioma
    Ewing's tumor
    leiomyosarcoma
    rhabdomyosarcoma
    colon carcinoma
    colorectal adenocarcinoma
    colon tumor metastatic to brain
    lung carcinoma
    pancreatic cancer
    breast cancer
    ovarian cancer
    prostate cancer
    squamous cell carcinoma
    basal cell carcinoma
    adenocarcinoma
    sweat gland carcinoma
    sebaceous gland carcinoma
    papillary carcinoma
    papillary adenocarcinomas
    cystadenocarcinoma
    medullary carcinoma
    bronchogenic carcinoma
    renal cell carcinoma
    hepatoma
    bile duct carcinoma
    choriocarcinoma
    seminoma
    embryonal carcinoma
    Wilms' tumor
    cervical cancer
    uterine cancer
    testicular tumor
    lung carcinoma
    small cell lung carcinoma
    bladder carcinoma
    epithelial carcinoma
    glioblastoma
    glioma
    astrocytoma
    medulloblastoma
    craniopharyngioma TABLE 1-continued

MALIGNANCIES AND RELATED DISORDERS ependymoma
pinealoma
hemangioblastoma
acoustic neuroma
oligodendroglioma
meningioma
melanoma
neuroblastoma
retinoblastoma In specific embodiments, malignancy or dysproliferative changes (such as metaplasias and dysplasias), or hyperproliferative disorders, are treated, inhibited or prevented in the brain. In other specific embodiments, carcinoma, melanoma, or leukemia is treated, inhibited or prevented.

5.5.1.2. Premalignant Conditions

The Therapeutics of the invention that antagonize Nr-CAM activity can also be administered to treat or inhibit premalignant conditions and to inhibit or prevent progression to a neoplastic or malignant state, including but not limited to those disorders listed in Table 1. Such prophylactic or therapeutic use is indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 1976, Basic Pathology, 2d Ed., W.B. Saunders Co., Philadelphia, pp. 68–79). Hyperplasia is a form of controlled cell proliferation involving an increase in cell number in a tissue or organ, without significant alteration in structure or function. As but one example, endometrial hyperplasia often precedes endometrial cancer. Metaplasia is a form of controlled cell growth in which one type of adult or fully differentiated cell substitutes for another type of adult cell. Metaplasia can occur in epithelial or connective tissue cells. Atypical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder.

Alternatively or in addition to the presence of abnormal cell growth characterized as hyperplasia, metaplasia, or dysplasia, the presence of one or more characteristics of a transformed phenotype, or of a malignant phenotype, displayed in vivo or displayed in vitro by a cell sample from a patient, can indicate the desirability of prophylactic/therapeutic administration of a Therapeutic that inhibits Nr-CAM function. As mentioned supra, such characteristics of a transformed phenotype include morphology changes, looser substratum attachment, loss of contact inhibition, loss of anchorage dependence, protease release, increased sugar transport, decreased serum requirement, expression of fetal antigens, disappearance of the 250,000 dalton cell surface protein, etc. (see also id., at pp. 84–90 for characteristics associated with a transformed or malignant phenotype).

In a specific embodiment, leukoplakia, a benign-appearing hyperplastic or dysplastic lesion of the epithelium, or Bowen's disease, a carcinoma in situ, are pre-neoplastic lesions indicative of the desirability of prophylactic intervention.

In another embodiment, fibrocystic disease (cystic hyperplasia, mammary dysplasia, particularly adenosis (benign epithelial hyperplasia)) is indicative of the desirability of prophylactic intervention.

In other embodiments, a patient which exhibits one or more of the following predisposing factors for malignancy is treated by administration of an effective amount of a Therapeutic: a chromosomal translocation associated with a malignancy (e.g., the Philadelphia chromosome for chronic myelogenous leukemia, t(14;18) for follicular lymphoma, etc.), familial polyposis or Gardner's syndrome (possible forerunners of colon cancer), benign monoclonal gammopathy (a possible forerunner of multiple myeloma), and a first degree kinship with persons having a cancer or precancerous disease showing a Mendelian (genetic) inheritance pattern (e.g., familial polyposis of the colon, Gardner's syndrome, hereditary exostosis, polyendocrine adenomatosis, medullary thyroid carcinoma with amyloid production and pheochromocytoma, Peutz-Jeghers syndrome, neurofibromatosis of Von Recklinghausen, retinoblastoma, carotid body tumor, cutaneous melanocarcinoma, intraocular melanocarcinoma, xeroderma pigmentosum, ataxia telangiectasia, Chediak-Higashi syndrome, albinism, Fanconi's aplastic anemia, and Bloom's syndrome; see Robbins and Angell, 1976, Basic Pathology, 2d Ed., W.B. Saunders Co., Philadelphia, pp. 112–113) etc.)

In another specific embodiment, a Therapeutic of the invention is administered to a human patient to prevent progression to brain, breast, colon, prostate, lung, or skin. In other specific embodiments, carcinoma, melanoma, or leukemia is treated or prevented.

5.5.1.3. Gene Therapy

In a specific embodiment, anti-sense nucleic acids complementary to a sequence encoding a Nr-CAM protein or functional derivative thereof, are administered to inhibit Nr-CAM function, by way of gene therapy. Gene therapy refers to therapy performed by the administration of a nucleic acid to a subject. In this embodiment of the invention, the antisense nucleic acid mediates a therapeutic effect by inhibiting Nr-CAM transcription and translation.

Any of the methods for gene therapy available in the art can be used according to the present invention. Exemplary methods are described below.

For general reviews of the methods of gene therapy, see Goldspiel et al., 1993, Clinical Pharmacy 12:488–505; Wu and Wu, 1991, Biotherapy 3:87–95; Tolstoshev, 1993, Ann. Rev. Pharmacol. Toxicol. 32:573–596; Mulligan, 1993, Science 260:926–932; and Morgan and Anderson, 1993, Ann. Rev. Biochem. 62:191–217; May, 1993, TIBTECH 11(5): 155–215). Methods commonly known in the art of recombinant DNA technology which can be used are described in Ausubel et al., (eds.), 1993, Current Protocols in Molecular Biology, John Wiley & Sons, NY; and Kriegler, 1990, Gene Transfer and Expression, A Laboratory Manual, Stockton Press, NY.

In one embodiment, the Therapeutic comprises an Nr-CAM sense or antisense nucleic acid that is part of an expression vector that expresses a Nr-CAM protein or fragment or chimeric protein thereof in a suitable host. In particular, such a nucleic acid has a promoter operably linked to the Nr-CAM coding region, said promoter being inducible or constitutive, and, optionally, tissue-specific. In another particular embodiment, a nucleic acid molecule is used in which the Nr-CAM coding sequences and any other desired sequences are flanked by regions that promote homologous recombination at a desired site in the genome, thus providing for intrachromosomal expression of the Nr-CAM nucleic acid (Koller and Smithies, 1989, Proc. Natl. Acad. Sci. USA 86:8932–8935; Zijlstra et al., 1989, Nature 342:435–438).

Delivery of the nucleic acid into a patient may be either direct, in which case the patient is directly exposed to the nucleic acid or nucleic acid-carrying vector, or indirect, in which case, cells are first transformed with the nucleic acid in vitro, then transplanted into the patient. These two approaches are known, respectively, as in vivo or ex vivo gene therapy.

In a specific embodiment, the nucleic acid is directly administered in vivo, where it is expressed to produce the encoded product. This can be accomplished by any of numerous methods known in the art, e.g., by constructing it as part of an appropriate nucleic acid expression vector and administering it so that it becomes intracellular, e.g., by infection using a defective or attenuated retroviral or other viral vector (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering it in linkage to a peptide which is known to enter the nucleus, by administering it in linkage to a ligand subject to receptor-mediated endocytosis (see e.g., Wu and Wu, 1987, *J. Biol. Chem.* 262:4429–4432) (which can be used to target cell types specifically expressing the receptors), etc. In another embodiment, a nucleic acid-ligand complex can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated Apr. 16, 1992 (Wu et al.); WO 92/22635 dated Dec. 23, 1992 (Wilson et al.); WO92/20316 dated Nov. 26, 1992 (Findeis et al.); WO93/14188 dated Jul. 22, 1993 (Clarke et al.), WO 93/20221 dated Oct. 14, 1993 (Young)). Alternatively, the nucleic acid can be introduced intracellularly and incorporated within host cell DNA for expression, by homologous recombination (Koller and Smithies, 1989, Proc. Natl. Acad. Sci. USA 86:8932–8935; Zijlstra et al., 1989, Nature 342:435–438).

In a specific embodiment, a viral vector that contains the Nr-CAM nucleic acid is used. For example, a retroviral vector can be used (see Miller et al., 1993, Meth. Enzymol. 217:581–599; Kondo, et al., 1998, *Cancer Res*, 68:962–967; Boviatsis, et al., 1994, *Human Gene Therapy*, 5:183–191. These retroviral vectors have been modified to delete retroviral sequences that are not necessary for packaging of the viral genome and integration into host cell DNA. The Nr-CAM nucleic acid to be used in gene therapy is cloned into the vector, which facilitates delivery of the gene into a patient. More detail about retroviral vectors can be found in Boesen et al., 1994, Biotherapy 6:291–302, which describes the use of a retroviral vector to deliver the mdr1 gene to hematopoietic stem cells in order to make the stem cells more resistant to chemotherapy. Other references illustrating the use of retroviral vectors in gene therapy are: Clowes et al., 1994, J. Clin. Invest. 93:644–651; Kiem et al., 1994, Blood 83:1467–1473; Salmons and Gunzberg, 1993, Human Gene Therapy 4:129–141; and Grossman and Wilson, 1993, Curr. Opin. in Genetics and Devel. 3:110–114.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, 1993, Current Opinion in Genetics and Development 3:499–503 present a review of adenovirus-based gene therapy. Bout et al., 1994, Human Gene Therapy 5:3–10 demonstrated the use of adenovirus vectors to transfer genes to the respiratory epithelia of rhesus monkeys. Other instances of the use of adenoviruses in gene therapy can be found in Rosenfeld et al., 1991, Science 252:431–434; Rosenfeld et al., 1992, Cell 68:143–155; and Mastrangeli et al., 1993, J. Clin. Invest. 91:225–234.

Adeno-associated virus (AAV) has also been proposed for use in gene therapy (Walsh et al., 1993, Proc. Soc. Exp. Biol. Med. 204:289–300.

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see e.g., Loeffler and Behr, 1993, Meth. Enzymol. 217:599–618; Cohen et al., 1993, Meth. Enzymol. 217:618–644; Cline, 1985, Pharmac. Ther. 29:69–92) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. In a preferred embodiment, epithelial cells are injected, e.g., subcutaneously. In another embodiment, recombinant skin cells may be applied as a skin graft onto the patient. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, a Nr-CAM nucleic acid is introduced into the cells such that it is expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention. Such stem cells include but are not limited to hematopoietic stem cells (HSC), stem cells of epithelial tissues such as the skin and the lining of the gut, embryonic heart muscle cells, liver stem cells (PCT Publication WO 94/08598, dated Apr. 28, 1994), and neural stem cells (Stemple and Anderson, 1992, Cell 71:973–985).

Epithelial stem cells (ESCs) or keratinocytes can be obtained from tissues such as the skin and the lining of the gut by known procedures (Rheinwald, 1980, Meth. Cell Bio. 21A:229). In stratified epithelial tissue such as the skin, renewal occurs by mitosis of stem cells within the germinal layer, the layer closest to the basal lamina. Stem cells within the lining of the gut provide for a rapid renewal rate of this tissue. ESCs or keratinocytes obtained from the skin or lining of the gut of a patient or donor can be grown in tissue culture (Rheinwald, 1980, Meth. Cell Bio. 21A:229; Pittelkow and Scott, 1986, Mayo Clinic Proc. 61:771). If the ESCs are provided by a donor, a method for suppression of host versus graft reactivity (e.g., irradiation, drug or antibody administration to promote moderate immunosuppression) can also be used.

With respect to hematopoietic stem cells (HSC), any technique which provides for the isolation, propagation, and maintenance in vitro of HSC can be used in this embodiment of the invention. Techniques by which this may be accomplished include (a) the isolation and establishment of HSC cultures from bone marrow cells isolated from the future host, or a donor, or (b) the use of previously established long-term HSC cultures, which may be allogeneic or xenogeneic. Non-autologous HSC are used preferably in conjunction with a method of suppressing transplantation immune reactions of the future host/patient. In a particular embodiment of the present invention, human bone marrow cells can be obtained from the posterior iliac crest by needle aspiration (see, e.g., Kodo et al., 1984, J. Clin. Invest. 73:1377–1384). In a preferred embodiment of the present invention, the HSCs can be made highly enriched or in substantially pure form. This enrichment can be accomplished before, during, or after long-term culturing, and can be done by any techniques known in the art. Long-term cultures of bone marrow cells can be established and maintained by using, for example, modified Dexter cell culture techniques (Dexter et al., 1977, J. Cell Physiol. 91:335) or Witlock-Witte culture techniques (Witlock and Witte, 1982, Proc. Natl. Acad. Sci. USA 79:3608–3612).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

Additional methods that can be adapted for use to deliver a nucleic acid encoding a Nr-CAM protein or functional derivative thereof are described herein below.

5.5.2. Treatment, Inhibition and Prevention of Hyperproloferative and Dysproliferative Disorders Diseases and disorders involving an increase in cell proliferation (growth) or in which cell proliferation is otherwise undesirable, are treated, inhibited or prevented by administration of a Therapeutic that antagonizes (inhibits) Nr-CAM function. Therapeutics that can be used include but are not limited to anti-Nr-CAM antibodies (and fragments and derivatives thereof containing the binding region thereof), Nr-CAM antisense nucleic acids, and Nr-CAM nucleic acids that are dysfunctional (e.g., due to a heterologous (non-Nr-CAM sequence) insertion within the Nr-CAM coding sequence) that are used to "knockout" endogenous Nr-CAM function by homologous recombination (see, e.g., Capecchi, 1989, Science 244:1288–1292). In a specific embodiment of the invention, a nucleic acid containing a portion of a Nr-CAM gene in which Nr-CAM sequences flank (are both 5' and 3' to) a different gene sequence, is used, as a Nr-CAM antagonist, to promote Nr-CAM inactivation by homologous recombination (see also Koller and Smithies, 1989, Proc. Natl. Acad. Sci. USA 86:8932–8935; Zijlstra et al., 1989, Nature 342:435–438). Other Therapeutics that inhibit Nr-CAM function can be identified by use of known convenient in vitro assays, e.g., based on their ability to inhibit binding of Nr-CAM to another protein or inhibit any known Nr-CAM function, as preferably assayed in vitro or in cell culture, although genetic assays in *Drosophila* or another species may also be employed. Preferably, suitable in vitro or in vivo assays, are utilized to determine the effect of a specific Therapeutic and whether its administration is indicated for treatment of the affected tissue.

In specific embodiments, Therapeutics that inhibit Nr-CAM function are administered therapeutically (including prophylactically): (1) in diseases or disorders involving an increased (relative to normal or desired) level of Nr-CAM protein or function, for example, in patients where Nr-CAM protein is overactive or overexpressed; or (2) in diseases or disorders wherein in vitro (or in vivo) assays (see infra) indicate the utility of Nr-CAM antagonist administration. The increased levels in Nr-CAM protein or function can be readily detected, e.g., by quantifying protein and/or RNA, by obtaining a patient tissue sample (e.g., from biopsy tissue) and assaying it in vitro for RNA or protein levels, structure and/or activity of the expressed Nr-CAM RNA or protein. Many methods standard in the art can be thus employed, including but not limited to immunoassays to detect and/or visualize Nr-CAM protein (e.g., Western blot, immunoprecipitation followed by sodium dodecyl sulfate polyacrylamide gel electrophoresis, immunocytochemistry, etc.) and/or hybridization assays to detect Nr-CAM expression by detecting and/or visualizing respectively Nr-CAM mRNA (e.g., Northern assays, dot blots, in situ hybridization, etc.), etc.

In other embodiments, chemical mutagenesis, or homologous recombination with an insertionally inactivated Nr-CAM gene (see Capecchi, 1989, Science 244:1288–1292 and Section 5.14 infra) can be carried out to reduce or destroy endogenous Nr-CAM function, in order to decrease cell proliferation. Suitable methods, modes of administration, and compositions that can be used to inhibit Nr-CAM function are described herein.

In an embodiment of the invention, a Therapeutic that inhibits Nr-CAM activity is used to treat, inhibit or prevent hyperproliferative or benign dysproliferative disorders. Specific embodiments are directed to treatment, inhibition or prevention of cirrhosis of the liver (a condition in which scarring has overtaken normal liver regeneration processes), treatment or inhibition of keloid (hypertrophic scar) formation (disfiguring of the skin in which the scarring process interferes with normal renewal), psoriasis (a common skin condition characterized by excessive proliferation of the skin and delay in proper cell fate determination), benign tumors, fibrocystic conditions, and tissue hypertrophy (e.g., prostatic hyperplasia).

5.5.2.1. Antisense Regulation of Nr-CAM Expression

In a specific embodiment, Nr-CAM function is inhibited by use of Nr-CAM antisense nucleic acids. The present invention provides the therapeutic or prophylactic use of nucleic acids of at least six nucleotides that are antisense to a gene or cDNA encoding Nr-CAM or a portion thereof. A Nr-CAM "antisense" nucleic acid as used herein refers to a nucleic acid capable of hybridizing to a portion of a Nr-CAM RNA (preferably mRNA) by virtue of some sequence complementarity. The antisense nucleic acid may be complementary to a coding and/or noncoding region of a Nr-CAM mRNA. Such antisense nucleic acids have utility as Therapeutics that inhibits Nr-CAM function, and can be used in the treatment or prevention of disorders as described supra in Section 5.5.2 and its subsections.

The antisense nucleic acids of the invention can be oligonucleotides that are double-stranded or single-stranded, RNA or DNA or a modification or derivative thereof, which can be directly administered to a cell, or which can be produced intracellularly by transcription of exogenous, introduced sequences.

In a specific embodiment, the Nr-CAM antisense nucleic acids provided by the present invention can be used to inhibit or prevent tumors or other forms of aberrant cell proliferation.

The invention further provides pharmaceutical compositions comprising an effective amount of the Nr-CAM antisense nucleic acids of the invention in a pharmaceutically acceptable carrier, as described infra.

In another embodiment, the invention is directed to methods for inhibiting the expression of a Nr-CAM nucleic acid sequence in a prokaryotic or eukaryotic cell comprising providing the cell with an effective amount of a composition comprising an Nr-CAM antisense nucleic acid of the invention.

Nr-CAM antisense nucleic acids and their uses are described in detail below.

5.5.2.1.1. Nr-CAM Antisense Nucleic Acids

The Nr-CAM antisense nucleic acids are of at least six nucleotides and are preferably oligonucleotides (ranging from 6 to about 50 oligonucleotides). In specific aspects, the oligonucleotide is at least 10 nucleotides, at least 15 nucleotides, at least 100 nucleotides, or at least 200 nucleotides. The oligonucleotides can be DNA or RNA or chimeric mixtures or derivatives or modified versions thereof, single-stranded or double-stranded. In a specific embodiment, the antisense nucleic acids of the invention are double-stranded RNA (see, Fire et al., 1998, Nature 391:806–811). The oligonucleotide can be modified at the base moiety, sugar moiety, or phosphate backbone. The oligonucleotide may include other appending groups such as peptides, or agents facilitating transport across the cell membrane (see, e.g., Letsinger et al., 1989, Proc. Natl. Acad. Sci. U.S.A. 86:6553–6556; Lemaitre et al., 1987, Proc. Natl. Acad. Sci. 84:648–652; PCT Publication No. WO 88/09810, published Dec. 15, 1988) or blood-brain barrier (see, e.g., PCT Publication No. WO 89/10134, published Apr. 25, 1988), hybridization-triggered cleavage agents (see, e.g., Krol et al., 1988, BioTechniques 6:958–976) or intercalating agents (see, e.g., Zon, 1988, Pharm. Res. 5:539–549).

In a preferred aspect of the invention, a Nr-CAM antisense oligonucleotide is provided, preferably of single-stranded DNA. The oligonucleotide may be modified at any position on its structure with substituents generally known in the art.

The Nr-CAM antisense oligonucleotide may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

In another embodiment, the oligonucleotide comprises at least one modified sugar moiety selected from the group including but not limited to arabinose, 2-fluoroarabinose, xylulose, and hexose.

In yet another embodiment, the oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641).

The oligonucleotide may be conjugated to another molecule, e.g., a peptide, hybridization triggered cross-linking agent, transport agent, hybridization-triggered cleavage agent, etc.

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448–7451), etc.

In a specific embodiment, the Nr-CAM antisense oligonucleotide comprises catalytic RNA, or a ribozyme (see, e.g., PCT International Publication WO 90/11364, published Oct. 4, 1990; Sarver et al., 1990, Science 247:1222–1225). In another embodiment, the oligonucleotide is a 2'-0-methylribonucleotide (Inoue et al., 1987, Nucl. Acids Res. 15:6131–6148), or a chimeric RNA–DNA analog (Inoue et al., 1987, FEBS Lett. 215:327–330).

In an alternative embodiment, the Nr-CAM antisense nucleic acid of the invention is produced intracellularly by transcription from an exogenous sequence. For example, a vector can be introduced in vivo such that it is taken up by a cell, within which cell the vector or a portion thereof is transcribed, producing an antisense nucleic acid (RNA) of the invention. Such a vector would contain a sequence encoding the Nr-CAM antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the Nr-CAM antisense RNA can be by any promoter known in the art to act in mammalian, preferably human, cells. Such promoters can be inducible or constitutive. Such promoters include but are not limited to: the SV40 early promoter region (Bernoist and Chambon, 1981, Nature 290:304–310), the promoter contained in the 3' long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42), etc.

The antisense nucleic acids of the invention comprise a sequence complementary to at least a portion of an RNA transcript of a Nr-CAM nucleic acid or Nr-CAM gene, preferably a human Nr-CAM gene. However, absolute complementarily, although preferred, is not required. A sequence "complementary to at least a portion of an RNA," as referred to herein, means a sequence having sufficient complementarity to be able to hybridize with the RNA, forming a stable duplex; in the case of double-stranded Nr-CAM antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with a Nr-CAM RNA it may contain and still form a stable duplex (or triplex, as the case may be). One skilled in the art can ascertain a tolerable degree of mismatch by use of standard procedures to determine the melting point of the hybridized complex.

5.5.2.1.2. Therapeutic Use of Nr-CAM Antisense Nucleic Acids

The Nr-CAM antisense nucleic acids can be used to treat, inhibit (or prevent) disorders of a cell type that expresses, or preferably overexpresses, Nr-CAM. In a specific embodiment, such a disorder is a hyperproliferative disorder, e.g. tumorigenesis. In a preferred embodiment, a single-stranded DNA antisense Nr-CAM oligonucleotide is used.

Cell types which express or overexpress Nr-CAM RNA can be identified by various methods known in the art. Such methods include but are not limited to hybridization with a Nr-CAM-specific nucleic acid (e.g. by Northern hybridization, dot blot hybridization, in situ hybridization), observing the ability of RNA from the cell type to be translated in vitro into Nr-CAM, immunoassay, etc. In a preferred aspect, primary tissue from a patient can be assayed for Nr-CAM expression prior to treatment, e.g., by immunocytochemistry or in situ hybridization.

Pharmaceutical compositions of the invention (see Section 5.10), comprising an effective amount of a Nr-CAM antisense nucleic acid in a pharmaceutically acceptable carrier, can be administered to a patient having a disease or disorder which is of a type that expresses or overexpresses Nr-CAM RNA or protein.

The amount of Nr-CAM antisense nucleic acid which will be effective in the treatment of a particular disorder or condition will depend on the nature of the disorder or condition, and can be determined by standard clinical techniques. Where possible, it is desirable to determine the antisense cytotoxicity of the tumor type to be treated in vitro, and then in useful animal model systems prior to testing and use in humans.

In a specific embodiment, pharmaceutical compositions comprising Nr-CAM antisense nucleic acids are administered via liposomes, microparticles, or microcapsules. In various embodiments of the invention, it may be useful to use such compositions to achieve sustained release of the Nr-CAM antisense nucleic acids. In a specific embodiment, it may be desirable to utilize liposomes targeted via antibodies to specific identifiable tumor antigens (Leonetti et al., 1990, Proc. Natl. Acad. Sci. U.S.A. 87:2448–2451; Renneisen et al., 1990, J. Biol. Chem. 265:16337–16342).

Additional methods that can be adapted for use to deliver a Nr-CAM antisense nucleic acid are described herein.

5.6. Demonstration of Therapeutic or Prophylactic Utility

The Therapeutics of the invention are preferably tested in vitro, and then in vivo for the desired therapeutic or prophylactic activity, prior to use in humans.

For example, in vitro assays which can be used to determine whether administration of a specific Therapeutic is indicated, include in vitro cell culture assays in which a patient tissue sample is grown in culture, and exposed to or otherwise administered a Therapeutic, and the effect of such Therapeutic upon the tissue sample is observed. In one embodiment, where the patient has a malignancy, a sample of cells from such malignancy is plated out or grown in culture, and the cells are then exposed to a Therapeutic. A Therapeutic which inhibits survival or growth of the malignant cells is selected for therapeutic use in vivo. Many assays standard in the art can be used to assess such survival and/or growth; for example, cell proliferation can be assayed by measuring $^3$H-thymidine incorporation, by direct cell count, by detecting changes in transcriptional activity of known genes such as proto-oncogenes (e.g., fos, myc) or cell cycle markers; cell viability can be assessed by trypan blue staining, differentiation can be assessed visually based on changes in morphology, etc.

In another embodiment, a Therapeutic is indicated for use which exhibits the desired effect, inhibition or promotion of cell growth, upon a patient cell sample from tissue having or suspected of having a hyper- or hypoproliferative disorder, respectively. Such hyper- or hypoproliferative disorders include but are not limited to those described herein.

In another specific embodiment, a Therapeutic is indicated for use in treating or inhibiting cell injury or a degenerative disorder which exhibits in vitro promotion of growth/proliferation of cells of the affected patient type.

In various specific embodiments, in vitro assays can be carried out with representative cells of cell types involved in a patient's disorder, to determine if a Therapeutic has a desired effect upon such cell types.

In another embodiment, cells of a patient tissue sample suspected of being pre-neoplastic are similarly plated out or grown in vitro, and exposed to a Therapeutic. The Therapeutic which results in a cell phenotype that is more normal (i.e., less representative of a pre-neoplastic state, neoplastic state, malignant state, or transformed phenotype) is selected for therapeutic use. Many assays standard in the art can be used to assess whether a pre-neoplastic state, neoplastic state, or a transformed or malignant phenotype, is present. For example, characteristics associated with a transformed phenotype (a set of in vitro characteristics associated with a tumorigenic ability in vivo) include a more rounded cell morphology, looser substratum attachment, loss of contact inhibition, loss of anchorage dependence, release of proteases such as plasminogen activator, increased sugar transport, decreased serum requirement, expression of fetal antigens, disappearance of the 250,000 dalton surface protein, etc. (see Luria et al., 1978, General Virology, 3d Ed., John Wiley & Sons, New York pp. 436–446).

In other specific embodiments, the in vitro assays described supra can be carried out using a cell line, rather than a cell sample derived from the specific patient to be treated, in which the cell line is derived from or displays characteristic(s) associated with the malignant, neoplastic or pre-neoplastic disorder desired to be treated or prevented, or is derived from the cell type upon which an effect is desired, according to the present invention.

Compounds for use in therapy can be tested in suitable animal model systems prior to testing in humans, including but not limited to rats, mice, chicken, cows, monkeys, rabbits, etc. For in vivo testing, prior to administration to humans, any animal model system known in the art may be used.

5.7. Therapeutic/Prophylactic Administration and Compositions

The invention provides methods of treatment (and prophylaxis) by administration to a subject of an effective amount of a Therapeutic of the invention. In a preferred aspect, the Therapeutic is isolated, purified or substantially purified. The subject is preferably an animal, including but not limited to animals such as cows, pigs, horses, chickens, cats, dogs, etc., and is preferably a mammal, and most preferably human. In a specific embodiment, a non-human mammal is the subject.

Formulations and methods of administration that can be employed when the Therapeutic comprises a nucleic acid are described above; additional appropriate formulations and routes of administration can be selected from among those described hereinbelow.

Various delivery systems are known and can be used to administer a Therapeutic of the invention, e.g., encapsulation in liposomes, microparticles, microcapsules, recombinant cells capable of expressing the Therapeutic, receptor-mediated endocytosis (see, e.g., Wu and Wu, 1987, J. Biol. Chem. 262:4429–4432), construction of a Therapeutic nucleic acid as part of a retroviral or other vector, etc. Methods of introduction include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In addition, it may be desirable to introduce a Therapeutic of the invention into the central nervous system by any suitable route, including, but not limited to intraventricular and intrathecal injection. Intraventricular injection may be facilitated by an intraventricular catheter, for example, attached to a reservoir, such as an Ommaya reservoir. Agents which enhance the delivery of chemotherapeutics to brain tumors, such as agonists which activate specific receptors on endothelial cells which regulate permeability, including, e.g., bradykinin agonists (see, e.g., Elliott, et al., 1996, Cancer Research 56:3998–4005) tumor angiogenesis factors (Cserr and Knopf, 1992, Immunol Today 12:507–512) etc. can be used in formulations and methods of administration when the Therapeutic is intended for delivery to a tumor of the central nervous system.

In a specific embodiment, injection into spinal fluid, and/or procedures utilizing an Ommaya reservoir, can be used to introduce a therapeutic of the invention such as an anti-Nr-CAM antibody, e.g. a bispecific anti-Nr-CAM antibody, directly into the central nervous system for immunotherapy of a tumor.

In yet another specific embodiment, an anti-Nr-CAM antibody, e.g. a bispecific anti-Nr-CAM antibody, is employed as a Therapeutic in an immunotherapeutic treatment of a non-brain tumor and is infused into a recipient intravenously.

Immune cells, e.g. dendritic cells or cytotoxic T-cells, can cross the blood-brain barrier and have access to brain tissue, especially in the presence of tumor angiogenesis factors (Cserr and Knopf, 1992, Immunol. Today, 12:507–512). In a preferred embodiment, activated dendritic cells (HLA-matched to the recipient) (see generally, Tjoa et al., 1996, Prostate 28:65–69) that have been exposed to a Nr-CAM protein, analog or derivative thereof are infused into a recipient under conditions that permit their crossing the blood-brain barrier, e.g. in the presence of tumor angiogenesis factors. In another preferred embodiment, activated cytotoxic T-cells (HLA-matched to the recipient) (see generally, Tjoa et al., 1996, Prostate 28:65–69) that have been exposed ex vivo (i.e. in vitro) to a Nr-CAM protein, analog, or derivative thereof are infused into a recipient under conditions that permit their crossing the blood-brain barrier.

In yet another specific embodiment, a Therapeutic of the invention; e.g., activated dendritic cells that have been exposed to a Nr-CAM protein, analog or derivative thereof, or activated cytotoxic T-cells that have been exposed ex vivo dendritic cells that have been exposed to a Nr-CAM protein, analog, or derivative thereof, is administered for the treatment of a non-brain tumor.

Pulmonary administration of a Therapeutic can also be employed, e.g., by use of an inhaler or nebulizer, and formulation with an aerosolizing agent.

In a specific embodiment, it may be desirable to administer the Therapeutic of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of a malignant tumor or neoplastic or pre-neoplastic tissue.

In another embodiment, the Therapeutic can be delivered in a vesicle, in particular a liposome (see Langer, 1990 Science 249:1527–1533; Treat et al., in Liposomes in the Therapy of Infectious Disease and Cancer, Lopez-Berestein and Fidler (eds.), Liss, New York, pp. 353–365 (1989); Lopez-Berestein, ibid., pp. 317–327; see generally ibid.)

In yet another embodiment, the Therapeutic can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fl. (1974); Controlled Drug Bioavailability, Drug Product Design and Performance, Smolen and Ball (eds.), Wiley, New York (1984); Ranger and Peppas, 1983, J. Macromol. Sci. Rev. Macromol. Chem. 23:61; see also Levy et al., 1985 Science 228:190; During et al., 1989 Ann. Neurol. 25:351; Howard et al., 1989 J. Neurosurg. 71:105). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115–138 (1984)).

Other controlled release systems are discussed in the review by Langer (Science 249:1527–1533 (1990)).

In a specific embodiment where the Therapeutic is a nucleic acid encoding a protein Therapeutic, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., 1991, Proc. Natl. Acad. Sci. USA 88:1864–1868), etc. Alternatively, a nucleic acid Therapeutic can be introduced intracellularly and incorporated within host cell DNA for expression, by homologous recombination.

The present invention also provides pharmaceutical compositions. Such compositions comprise a therapeutically effective amount of a Therapeutic, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the Therapeutic, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The Therapeutics of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the Therapeutic of the invention which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. However, suitable dosage ranges for intravenous administration are generally about 20–500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

Suppositories generally contain active ingredient in the range of 0.5% to 10% by weight; oral formulations preferably contain 10% to 95% active ingredient.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

5.7.1. Treatment and Prevention of Hypoproliferative Disorders

Diseases and disorders involving decreased cell proliferation or in which cell proliferation is desired for treatment or prevention, and that can be treated or prevented by promoting Nr-CAM function, include but are not limited to degenerative disorders, growth deficiencies, hypoproliferative disorders, physical trauma, lesions, and wounds; for example, to promote wound healing, or to promote regeneration in degenerated, lesioned or injured tissues, etc. In a specific embodiment, nervous system disorders are treated. In another specific embodiment, a disorder that is not of the nervous system is treated.

Lesions which may be treated according to the present invention include but are not limited to the following lesions:

(i) traumatic lesions, including lesions caused by physical injury or associated with surgery;

(ii) ischemic lesions, in which a lack of oxygen results in cell injury or death, e.g., myocardial or cerebral infarction or ischemia, or spinal cord infarction or ischemia;

(iii) malignant lesions, in which cells are destroyed or injured by malignant tissue;

(iv) infectious lesions, in which tissue is destroyed or injured as a result of infection, for example, by an abscess or associated with infection by human immunodeficiency virus, herpes zoster, or herpes simplex virus or with Lyme disease, tuberculosis, syphilis;

(v) degenerative lesions, in which tissue is destroyed or injured as a result of a degenerative process, including but not limited to nervous system degeneration associated with Parkinson's disease, Alzheimer's disease, Huntington's chorea, or amyotrophic lateral sclerosis;

(vi) lesions associated with nutritional diseases or disorders, in which tissue is destroyed or injured by a nutritional disorder or disorder of metabolism including but not limited to, vitamin B12 deficiency, folic acid deficiency, Wernicke disease, tobacco-alcohol amblyopia, Marchiafava-Bignami disease (primary degeneration of the corpus callosum), and alcoholic cerebellar degeneration;

(vii) lesions associated with systemic diseases including but not limited to diabetes or systemic lupus erythematosus;

(viii) lesions caused by toxic substances including alcohol, lead, or other toxins; and (ix) demyelinated lesions of the nervous system, in which a portion of the nervous system is destroyed or injured by a demyelinating disease including but not limited to multiple sclerosis, human immunodeficiency virus-associated myelopathy, transverse myelopathy or various etiologies, progressive multifocal leukoencephalopathy, and central pontine myelinolysis.

Nervous system lesions which may be treated in a patient (including human and non-human mammalian patients) according to the invention include but are not limited to the lesions of either the central (including spinal cord, brain) or peripheral nervous systems.

Therapeutics which are useful according to this embodiment of the invention for treatment of a disorder may be selected by testing for biological activity in promoting the survival or differentiation of cells (see also Section 5.9). For example, in a specific embodiment relating to therapy of the nervous system, a Therapeutic which elicits one of the following effects may be useful according to the invention:

(i) increased sprouting of neurons in culture or in vivo;

(ii) increased production of a neuron-associated molecule in culture or in vivo, e.g., choline acetyltransferase or acetylcholinesterase with respect to motor neurons; or (iii) decreased symptoms of neuron dysfunction in vivo.

Such effects may be measured by any method known in the art. In preferred, non-limiting embodiments, increased sprouting of neurons may be detected by methods set forth in Pestronk et al. (1980, Exp. Neurol. 70:65–82) or Brown et al. (1981, Ann. Rev. Neurosci. 4:17–42); and increased production of neuron-associated molecules may be measured by bioassay, enzymatic assay, antibody binding, Northern blot assay, etc., depending on the molecule to be measured.

5.8. Additional Use of Increased Nr-CAM Function to Promote Increased Growth Promotion of Nr-CAM function (e.g., by administering a compound that promotes Nr-CAM function as described above), has utility that is not limited to therapeutic or prophylactic applications. For example, Nr-CAM function can be promoted in order to increase growth of animals (e.g., cows, horses, pigs, goats, deer, chickens) and plants (particularly edible plants, e.g., tomatoes, melons, lettuce, carrots, potatoes, and other vegetables), particularly those that are food or material sources. In an embodiment in which a Nr-CAM nucleic acid is under the control of a tissue-specific promoter, the invention can be used in plants or animals to increase growth where desired (e.g., in the fruit or muscle). For example, a Nr-CAM nucleic acid under the control of a temperature-sensitive promoter can be administered to a plant or animal, and the desired portion of the (or the entire) plant or animal can be subjected to heat in order to induce Nr-CAM nucleic acid production, resulting in increased Nr-CAM expression, and resulting cell proliferation. Methods to make plants recombinant are commonly known in the art and can be used. Regarding methods of plant transformation (e.g., for transformation with a Nr-CAM antisense nucleic acid), see e.g., Valvekens et al., 1988, Proc. Natl. Acad. Sci. USA 85:5536–5540. Regarding methods of targeted gene inactivation in plants (e.g., to inactivate Nr-CAM), see e.g., Miao and Lam, 1995, The Plant J. 7:359–365.

Promotion of Nr-CAM function can also have uses in vitro, e.g., to expand cells in vitro, including but not limited to stem cells, progenitor cells, muscle cells, fibroblasts, liver cells, etc., e.g., to grow cells/tissue in vitro prior to administration to a patient (preferably a patient from which the cells were derived), etc.

5.9. Screening for Nr-CAM Agonists and Antigonists

Nr-CAM nucleic acids, proteins, and derivatives also have uses in screening assays to detect molecules that specifically bind to Nr-CAM nucleic acids, proteins, or derivatives and thus have potential use as agonists or antagonists of Nr-CAM, in particular, molecules that thus affect cell proliferation. In a preferred embodiment, such assays are performed to screen for molecules with potential utility as anti-cancer drugs or lead compounds for drug development. The invention thus provides assays to detect molecules that specifically bind to Nr-CAM nucleic acids, proteins, or derivatives. For example, recombinant cells expressing Nr-CAM nucleic acids can be used to recombinantly produce Nr-CAM proteins in these assays, to screen for molecules that bind to a Nr-CAM protein. Molecules (e.g., putative binding partners of Nr-CAM) are contacted with the Nr-CAM protein (or fragment thereof) under conditions conducive to binding, and then molecules that specifically bind to the Nr-CAM protein are identified. Similar methods can be used to screen for molecules that bind to Nr-CAM derivatives or nucleic acids. Methods that can be used to carry out the foregoing are commonly known in the art.

By way of example, diversity libraries, such as random or combinatorial peptide or nonpeptide libraries can be screened for molecules that specifically bind to Nr-CAM. Many libraries are known in the art that can be used, e.g., chemically synthesized libraries, recombinant (e.g., phage display libraries), and in vitro translation-based libraries.

Examples of chemically synthesized libraries are described in Fodor et al., 1991, Science 251:767–773; Houghten et al., 1991, Nature 354:84–86; Lam et al., 1991, Nature 354:82–84; Medynski, 1994, Bio/Technology 12:709–710; Gallop et al., 1994, J. Medicinal Chemistry 37(9):1233–1251; Ohlmeyer et al., 1993, Proc. Natl. Acad. Sci. USA 90:10922–10926; Erb et al., 1994, Proc. Natl. Acad. Sci. USA 91:11422–11426; Houghten et al., 1992, Biotechniques 13:412; Jayawickreme et al., 1994, Proc. Natl. Acad. Sci. USA 91:1614–1618; Salmon et al., 1993, Proc. Natl. Acad. Sci. USA 90:11708–11712; PCT Publication No. WO 93/20242; and Brenner and Lerner, 1992, Proc. Natl. Acad. Sci. USA 89:5381–5383.

Examples of phage display libraries are described in Scott and Smith, 1990, Science 249:386–390; Devlin et al., 1990, Science, 249:404–406; Christian, R. B., et al., 1992, J. Mol. Biol. 227:711–718); Lenstra, 1992, J. Immunol. Meth. 152:149–157; Kay et al., 1993, Gene 128:59–65; and PCT Publication No. WO 94/18318 dated Aug. 18, 1994.

In vitro translation-based libraries include but are not limited to those described in PCT Publication No. WO 91/05058 dated Apr. 18, 1991; and Mattheakis et al., 1994, Proc. Natl. Acad. Sci. USA 91:9022–9026.

By way of examples of nonpeptide libraries, a benzodiazepine library (see e.g., Bunin et al., 1994, Proc. Natl. Acad. Sci. USA 91:4708–4712) can be adapted for use. Peptoid libraries (Simon et al., 1992, Proc. Natl. Acad. Sci. USA 89:9367–9371) can also be used. Another example of a library that can be used, in which the amide functionalities in peptides have been permethylated to generate a chemically transformed combinatorial library, is described by Ostresh et al. (1994, Proc. Natl. Acad. Sci. USA 91:11138–11142).

Screening the libraries can be accomplished by any of a variety of commonly known methods. See, e.g., the following references, which disclose screening of peptide libraries: Parmley and Smith, 1989, Adv. Exp. Med. Biol. 251:215–218; Scott and Smith, 1990, Science 249:386–390; Fowlkes et al., 1992; BioTechniques 13:422–427; Oldenburg et al., 1992, Proc. Natl. Acad. Sci. USA 89:5393–5397; Yu et al., 1994, Cell 76:933–945; Staudt et al., 1988, Science 241:577–580; Bock et al., 1992, Nature 355:564–566; Tuerk et al., 1992, Proc. Natl. Acad. Sci. USA 89:6988–6992; Ellington et al., 1992, Nature 355:850–852; U.S. Pat. Nos. 5,096,815, 5,223,409, and 5,198,346, all to Ladner et al.; Rebar and Pabo, 1993, Science 263:671–673; and PCT Publication No. WO 94/18318.

In a specific embodiment, screening can be conducted out by contacting the library members with a Nr-CAM protein (or nucleic acid or derivative) immobilized on a solid phase and harvesting those library members that bind to the protein (or nucleic acid or derivative). Examples of such screening methods, termed "panning" techniques are described by way of example in Parmley and Smith, 1988, Gene 73:305–318; Fowlkes et al., 1992, BioTechniques 13:422–427; PCT Publication No. WO 94/18318; and in references cited hereinabove.

In another embodiment, the two-hybrid system for selecting interacting proteins in yeast (Fields and Song, 1989, Nature 340:245–246; Chien et al., 1991, Proc. Natl. Acad. Sci. USA 88:9578–9582) can be used to identify molecules that specifically bind to a Nr-CAM protein or derivative.

5.10. Animal Models

The invention also provides animal models. In one embodiment, animal models for diseases and disorders involving cell hypoproliferation (e.g., as described in Section 5.8.1) are provided. Such an animal can be initially produced by promoting homologous recombination between a Nr-CAM gene in its chromosome and an exogenous Nr-CAM gene that has been rendered biologically inactive (preferably by insertion of a heterologous sequence, e.g., an antibiotic resistance gene). In a preferred aspect, this homologous recombination is carried out by transforming embryo-derived stem (ES) cells with a vector containing the insertionally inactivated Nr-CAM gene, such that homologous recombination occurs, followed by injecting the ES cells into a blastocyst, and implanting the blastocyst into a foster mother, followed by the birth of the chimeric animal ("knockout animal") in which a Nr-CAM gene has been inactivated (see Capecchi, 1989, Science 244:1288–1292). The chimeric animal can be bred to produce additional knockout animals. Such animals can be mice, hamsters, sheep, pigs, cattle, etc., and are preferably non-human mammals. In a specific embodiment, a knockout mouse is produced.

Such knockout animals are expected to develop or be predisposed to developing diseases or disorders involving cell hypoproliferation. Such animals can be used to screen for or test molecules for the ability to promote proliferation and thus treat or prevent such diseases and disorders.

In a different embodiment of the invention, transgenic animals that have incorporated and express a functional Nr-CAM gene have use as animal models of diseases and disorders involving cell hyperproliferation or malignancy. Such animals are expected to develop or be predisposed to developing diseases or disorders involving cell hyperproliferation (e.g., malignancy) and thus can have use as animal models of such diseases and disorders, e.g., to screen for or test molecules (e.g., potential anti-cancer therapeutics) for the ability to inhibit overproliferation (e.g., tumor formation) and thus treat or prevent such diseases or disorders.

The following examples are provided for the purposes of illustration only and are intended to limit the scope of the invention in any manner.

6. EXAMPLE

Isolation of the Nr-CAM Gene from and Characterization of its Expression in Human Glioblastoma Multiforme Tumor Tissue In this study, the role of Nr-CAM in brain tumorigenesis was characterized.

6.1. Materials and Methods

6.1.1. Human Tissues and Cell Lines

Tissue samples of brain and non-brain tumors were procured from the tissue bank maintained by Pacific Northwest Cancer Foundation, Northwest Hospital, and from resources at the Mayo Clinic (Rochester, Minn.). Brain tumor cell lines astrocytoma grade IV (CCF-STTG1), astrocytoma grade III (SW 1738), neuroblastoma (IMR-32), medulloblastoma (D283 Med), glioma (Hs 683), neuroectodermal (PFSK-1), GM(DBTRG-05MG) were purchased from the ATCC (Rockville, Md.). Fetal normal human astrocytes (FNHAs) were purchased from Clonetics (San Diego, Calif.). All cell lines were cultured under the conditions recommended by the ATCC or Clonetics.

6.1.2. Differential Display Polymerase Chain Reaction (DD-PCR)

In order to isolate and clone genes differentially expressed in normal brain tissue (NBT) and glioblastoma multiforme tissue (GMT), the technique of Different Display-PCR (DD-PCR) was utilized. (Examples of protocols of DD-PCR may be found in Sehgal et al., 1997, J. Surg. Oncol. 64:102–108; Sehgal et al., 1997, J. Surg. Oncol. 65:249–257; Sehgal et al., 1997, Int. J. Cancer 71:565–572 (Sehgal, 1997b); Sehgal et al., 1996, Exp. Lung. Res. 22:419–434).

NBT and GMT were obtained from the same region of the brain. Total RNA was isolated and first strand cDNA synthesis was carried out using the first strand cDNA synthesis kit from Clontech (Palo Alto, Calif.) using BT3-2 primer (5'T [T] 18NG3'). Approximately 125 ng of first strand eDNA synthesis product were used for carrying out PCR. DD-PCR was carried out using ($\lambda P^{32}$) end-labeled BT3-2 primer and BT10 (5'-NGCTGCTCTCATACT-3' (SEQ. ID. NO. 8)) primer using eDNA from NBT or GMT tissue in duplicate under the conditions described previously (Sehgal et al., 1997a). PCR products were run on a 6% sequencing gel. Bands that showed differential expressions were cut out, and DNA was eluted and cloned into a PCRII vector (Invitrogen, San Diego, Calif.) Positive clones were screened by PCR and sequenced using the Sequenase version 2.0 sequencing kit from Amersham/USB (Cleveland, OHIO).

6.1.3. Gene Specific RT-PCR

To confirm differential expression of clones isolated by DD-PCR, gene-specific RT-PCR technique was carried out as described previously (Sehgal et al., 1997b). hNr-CAM specific primers (5'-AACATATGGGTAGAGAGTATATTT-3' (SEQ. ID No. 9); and 5'-CTTTGCATTCCAGTTCATAT-TAA-3' (SEQ. ID. NO. 10) were used for PCR. This PCR results in a 250 bp product at the 3' end of the hNr-CAM gene. For EGFR, gene-specific primers (5'-TGTGGTGA-CAGATCACGGCT-3' (SEQ. ID. No. 11) and 5'-CAGCT-CAAACCTGTGATTTCC-3') (SEQ. ID. No. 12) were used for PCR and an internal primer (5'-AATAGGTATTGGT-GAATTTAAAGACTCACTCTCCATAAATGC TAC-GAATATTAAACACTT-3') (SEQ. ID. No. 13) for Southern blot analysis. As a control for PCR, D1-2 (mitochondrial Cytochrome C oxidase subunit 1 gene, Accession Number D38112), a housekeeping gene, which is expressed in both NBT and GMT, was used. PCR was carried out using D1-2-specific primers (5'-CGGAGCAATATGAAAT-GATCT-3' (SEQ. ID. NO.: 14) and 5'-GCAAATACAGCTC-CTATTG-3') (SEQ. ID. NO.: 15), resulting in a 200 bp product. PCR for all 3 genes was carried out using Taq DNA polymerase under the conditions recommended by Qiagen (Chatsworth, Calif.). PCR product was then run on a 2% agarose gel and transferred onto a Hybond N+ nylon membrane using standard Southern blotting conditions, as described previously (Sehgal et al., 1997a). Hybridization was done at 42° C. using hNr-CAM, EGFR and D1-2-specific probes. EGFR, hNr-CAM and D1-2-specific probes were prepared by multiprime labeling (Amersham, Arlington Heights, Ill.) of hNr-CAM-specific primers (5'-GCTG-TATGTTAGTATTATGAGAATAGTTACAG-CAAAAACATAA CTCAGT-3') (SEQ. ID. No.: 16) or D1-2-specific primer (5'-TAGGCCTGACTGGCATTG-TATTAGCAAACTCATCACTAGA-3') (SEQ. ID. No.: 17). These primers are internal to the primers used for PCR, and they do not carry any of the primer sequences used in the PCR. Primer sequences were checked for homologous sequences using the DNA BLAST program of NCBI (National center for Biotechnology Information, Bethesda, Md.) prior to usage. Quantitation of the signal on Southern blot was carried out using the ImageQuaNT program of Molecular Dynamics (Sunnyvale, Calif.). This protocol was used to quantitate expression of EGFR, D4-1 or D1-2 in brain tumor cell lines, FNHA and selected tumor tissues. We have demonstrated previously that this gene-specific RT-PCR technique is semi-quantitative (Sehgal et al., 1997a, b).

6.1.4. Northern Blot Analysis

Multiple Normal Human tissue blots (MNHTB) were purchased from Clontech (Palo Alto, Calif.). These blots contained 2 µg of pure polyA+ mRNA. MNHTBs were prehybridized in express hybridization buffer solution (Clontech) for 3–4 hours. Hybridization was done with multiprime labeled 179 bp D4-1 probe. After autoradiographic exposure, the probe was washed from the blot and then hybridized with human β actin probe (Clontech). Quantification of expression of hNr-CAM and β actin was done using the ImageQuaNT program. Expression of Nr-CAM in different regions of normal brain and cell lines formed from tumor tissues was assessed.

6.1.5. Quantitation of Northern and Southern Blots

Quantitation of Northern and Southern blots also was performed using the ImageQuaNT volume quantitation program. Volume quantitation calculates the volume under the surface created by a 3-D plot of pixel locations and pixel values. We quantitated the volume (the integrated intensity of all pixels in the spot excluding background) of D1-2 bands in Northern or Southern blots. These pixel values are then normalized with pixel values in the bands of housekeeping genes (D1-2 or β actin) and are referred to as "relative expression" in the figures. The subjective terms "low", "medium" and "high" refer to relative expression and are based on hNr-CAM expression in normal brain as "low" and in tumor brain as "high".

6.1.6. In Situ Hybridization

The technique of In situ hybridization was done as described previously (Wilkinson, 1992 In Situ Hybridization, A practical approach. NY: Oxford University Press). Briefly, 6 μm formalin fixed, paraffin embedded human brain tumor sections were deparaffinized by 2 washes in xylene, followed by rehydration through graded concentrations of ethanol from 100% to 70%. These were then washed in PBS and treated with Proteinase K (25 mg/ml for 10 minutes), followed by fixation in 4% paraformaldehyde. After incubation in 0.25% acetic anhydride/0.1 M TEA (Tri-Ethyl Acetic acid), sections were dehydrated through graded concentrations of ethanol from 70% to 100% and prehybridized for 2 hours at 55° C. in 50% formamide, 5×SSC pH 4.5, 50 μg/ml tRNA, 50 μg/ml heparin, and 1% SDS. Sections were hybridized with 1 μg/ml DIG-(Digoxygenin) labeled antisense or sense probes for 18 hours at 55° C.

Probes, sense and anti-sense, were synthesized with the Genius 4 kit (Boehringer Mannheim, Indianapolis, Ind.) using the T3 and T7 promoters of a PCR template derived from human Bravo/Nr-CAM sequences corresponding to bases 3731–3754 and 4101–4114. See FIG. 2A in which BT180 represents the 5' primer for the probe corresponding to nucleotides 3731–3754 and BT181, the 3' primer for the probe corresponding to nucleotides 4104–4114. Following hybridization, slides were washed in 50% formamide, 2×SSC pH 4.5, 1% SDS at 50° C., treated with 5 μg/ml RNase A for 30 minutes at 37° C., and washed in 50% formamide, 2×SSC pH 4.5 at 50° C. Sections were pre-blocked in 10% normal sheep serum (Sigma, St. Louis, Mo.) and incubated with a 1:2000 dilution of alkaline phosphate conjugated anti-dioxigenin Fab fragments (Boehringer Mannheim) 18 hours at 4° C. For detection, slides were incubated with NBT/BCIP (5-Bromo-4-chloro-3-indilyl-phosphate, 4-toluidine salt) in the dark for 46 hours. After counter staining with eosin Y, slides were mounted with Permount and visualized using an Axioskop (Carl Zeiss, Thornwood, N.Y.) routine microscope.

6.1.7. Genomic Southern Blot

NIH3T3, astrocytoma III, glioma and glioblastoma cells were grown in 100 mm diameter plates until 90% confluent under the conditions recommended by the ATCC. Genomic DNA was isolated using a DNA isolation kit from Puragen (Research Triangle Park, N.C.); 10 μg of DNA were cut with 50 U of EcoRI restriction enzyme from GIBCO BRL (Gaithersburg, Md.) and run on a 1% agarose gel. DNA was transferred onto a Hybond N+ nylon membrane (Amersham) using the protocol recommended by Puragen. After incubating the membrane in pre-hybridization solution, hybridization was conducted using a 375 bp hNr-CAM probe (nucleotide position 3731–4126) (Lane et al., 1996, Genomics 35:456–465) labeled (1×10⁴ CPM/ml) using the multiprime labeling kit from Amersham. Membrane was washed in 0.1×SSC/0.1% SDS at 24° C. for 30 mins and then exposed to Kodak X-ray film.

6.2. Results

6.2.1. Isolation of Human Nr-CAM from and Differential Expression of Nr-CAM in Glioblastoma Using the modified technique of DD-PCR as described in Section 6.1.2., a cDNA fragment, designated D4-1, was identified which is over-expressed in glioblastoma multiform tissue (GMT) as compared with normal brain tissue (NBT). FIG. 1 demonstrates that D4-1 is over-expressed in GMT. The band designated C in FIG. 1 is the cDNA of the D1-2 gene, a control gene present in both GMT and NBT.

The D4-1 band was isolated from the gel and cloned into the PCRII vector from Invitrogen as described in Section 6.1.2. Sequence identity analysis indicated that this cDNA is identical to the last 38 bases at the 3' end of the previously isolated hNr-CAM gene. FIG. 2C presents the results of sequence identity analysis together with a comparison of the sequence of the isolated hNr-CAM with that of the rat Nr-CAM. The isolated D4-1 cDNA has 99.2% sequence identity (homology) to the rat Nr-CAM. Thus, the sequence identity analysis demonstrates that clone D4-2 is hNr-CAM.

In situ hybridization conducted as described in Section 6.1.6 using an anti-sense Nr-CAM confirmed differential expression of hNr-CAM in glioblastoma as compared to normal brain tissue. Results are presented in FIGS. 3(a–f).

Figure 3B:
Figure 3C:
Figure 3D:
Figure 3E:
Figure 3F:
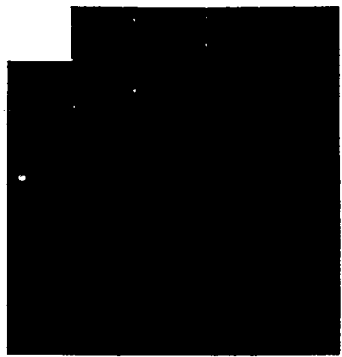

As shown in FIGS. 3a and d, strong expression of hNr-CAM is observed in a number of cells from 2 GMT samples, using the anti-sense hNr-CAM probe. Low or no signal was observed when hNr-CAM sense probe was used on serial sections (FIG. 3b,e). The NBTs did not show any signal with the hNr-CAM anti-sense probe (FIG. 3c,f). This experiment indicates that hNr-CAM is differentially over-expressed in GMT as compared to NBT.

6.2.2. Expression of Nr-CAM in Human Tumor Tissues

As shown in FIGS. 4(A and B), hNr-CAM is expressed at high levels in glioblastoma IV and glioma tissue as compared to NBT using RT-PCR. Low or no expression of hNr-CAM was observed in recurrent meningioma, meningioma, neuroblastoma, recurrent malignant glioma, melanoma, breast tumor, benign prostate tissue or NBT. In one of the GMT samples studied, no hNr-CAM expression was observed. High expression of hNr-CAM was observed in NBT undergoing extensive gliosis. This is an unusual observation, and the reason for it is not known at present. D1-2 is a housekeeping gene that has been used previously as an internal control in RT-PCR (Sehgal et al., 1997a,b).

The expression of hNr-CAM in NBT and astrocytoma tumor tissue was evaluated using RT-PCR. As shown in FIGS. 5(A and B), a high level of hNr-CAM is expressed in astrocytoma as compared to NBT. The expression pattern of EGFR, a known brain tumor marker, was investigated from this set of cDNA. As shown in the middle and bottom panels of FIGS. 5A and in 5B, expression of hNr-CAM is higher in tumor than is EGFR.

6.2.3. Expression of Nr-CAM in Brain Tumor Cell Lines

Expression of hNr-CAM in cell lines derived from several different kinds of human brain tumor was investigated. As shown in FIGS. 6(A and B), Nr-CAM is expressed at high levels in astrocytoma IV, glioma, glioblastoma and neuro-ectodermal tumor cell lines as compared to NBT. Low or no expression of hNr-CAM was observed in cell lines derived from astrocytoma III, medulloblastoma, neuroblastoma and NBT. The hNr-CAM transcript was not detected in FNHAs or NIH3T3 cells (data not shown).

6.2.4. Expression of Nr-CAM in Normal Human Brain

Seven different regions of the brain and spinal cord were studied for hNr-CAM expression. As shown in FIGS. 7(A and B), a natural transcript of hNr-CAM (7.5 kb) was observed in cerebellum, occipital lobe, cerebral cortex and frontal lobe at a higher level as compared to spinal cord, medulla, temporal lobe or putamen. Expression of hNr-CAM detected is low as compared to tumor cell lines (FIGS. 8(A and B) or the other tumor-associated gene (D2-2) previously studied. Expression of hNr-CAM is highest in kidney, and no significant difference in expression between fetal and adult tissues was observed (data not shown).

6.2.5. Expression of Nr-CAM in Human Tumor Cell Lines

As shown in FIGS. 8(A and B), hNr-CAM was expressed at high levels in melanoma G361, lymphoblastic leukemia (MOLT-4) and Burkitt's lymphoma Raji cell lines. A low level of hNr-CAM expression was observed in promyelocytic leukemia (HL-60), HeLa cell S3, chronic myelogenous leukemia (K-562), colorectal adenocarcinoma (SW480) and lung carcinoma (A549). All of the cell lines studied herein expressed hNr-CAM mRNAs that are 1.4 kb as compared to the 7.5 kb transcript expressed in normal brain (FIG. 5(A and B)). HeLa cells S3 express low levels of both transcripts. Melanoma G361 express high levels of the 7.5 kb and low levels of the 1.4 kb transcript, suggesting alternative splicing of hNr-CAM mRNA during tumorigenesis.

Using Northern blot analysis as described in Section 6.1.4, expression of Nr-CAM was investigated in 8 different human tumor cell lines.

6.2.6. Expression of Nr-CAM in Human Brain Tumors Using In Situ Hybridization In situ hybridization as described above was performed on a panel of 20 different brain tumors using anti-sense and sense hNr-CAM-specific probes. Results from this study are shown in Table 2.

TABLE 2

EXPRESSION OF HNR-CAM IN HUMAN BRAIN TUMORS: PRESENCE OR ABSENCE OF HNR-CAM IS SHOWN BY POSITIVE OR NEGATIVE SIGNS

| TISSUE | hNr-CAM |
| --- | --- |
| Glioblastoma multiforme | + |
|  | + |
|  | + |
|  | + |
|  | − |
|  | − |
|  | − |
|  | − |
| Genicystic anaplastic astrocytoma | − |
| Meningotheliomatous meningioma | + |
| Normal brain | − |
|  | − |
|  | − |
|  | − |
| Glioma III/IV | + |
| Pilocystic astrocytoma | + |
| Malignant glioma | − |
| Lipidized meningioma | + |
| Meningioma syncytial type | + |
| Meningioma | − |

TABLE 2-continued

EXPRESSION OF HNR-CAM IN HUMAN BRAIN TUMORS: PRESENCE OR ABSENCE OF HNR-CAM IS SHOWN BY POSITIVE OR NEGATIVE SIGNS

| TISSUE | hNr-CAM |
| --- | --- |
| Fibroblastic meningioma | − |
| Meningotheliomatous meningioma, grade I | + |
| Genicystic astrocytoma | − |
| Oligodendroglioma, grade II | + |

Eleven of the 20 tumors (55%) showed positive signal for hNr-CAM. Four NBT samples did not show any hNr-CAM expression. None of the early grade astrocytomas and only 50% of the highly anaplastic astrocytomas showed Nr-CAM expression. Similar hNr-CAM expression was observed in brain tumor cell lines (FIGS. 6(A and B)). hNr-CAM expression was observed in 50% of meningiomas tested and one oligodendroglioma. These results demonstrate that expression of hNr-CAM is prevalent in malignant glioma tissue.

6.2.7. Gene Amplification

Genomic Southern blot was performed as described in Section 6.1.7 on 3 brain tumor cell lines (astrocytoma III, glioma and glioblastoma) and the NIH3T3 cell line. As show in FIG. 9 no change in the genetic level of hNR-CAM was observed in the 4 cell lines tested.

These results indicate that the over-expression of hNr-CAM in brain tumors is not due to gene amplification.

A 1.4 kb transcript of hNr-CAM was observed presently in tumor cell lines as compared to a 7.5 kb transcript in normal brain (Lane et al., 1996). This may indicate that the 7.5 kb transcript for hNr-CAM generates a 1.4 kb transcript that could translate into a small version of the hNr-CAM protein, which may be tumor-specific. On the basis of data presented in this study, we conclude that hNr-CAM is over-expressed in human malignant brain tumors and that it is useful to serve as a marker for detection and for therapy.

7. EXAMPLE

Effect of Regulating Nr-CAM Expression in Glioblastoma

In order to assess the functional role of Nr-CAM in brain tumorigenesis, the effects of over-expressing Nr-CAM in the anti-sense direction were examined in a glioblastoma cell line.

7.1. Materials and Methods 7.1.1. Cloning of Antisense Nr-CAM

The full length clone for Nr-CAM was provided by William Dryer (CalTech). Three different portions of the hNr-CAM gene were cloned in the antisense direction.

To obtain antisense "Nr-CAM 1/3 clone", Nr-CAM 1/3 (corresponding to nucleotides beginning at nucleotide 119 and ending at nucleotide 1434 of FIG. 2A) was amplified using primers BT306 (5'TAGATACAACTAGTCTAATG-CAGCTTAAAATA ATGCC 3')(SEQ. ID. No.: 18) and BT307 (5'AGATAGATCCGCGGATATCCATATT CATTA-GAGGCATTG 3') (SEQ. ID. NO.: 19) (see FIG. 2A) and cloned into precut pCMVneo vector cut with SacII and SpeL restriction enzymes. PCR amplification was carried out for 1 cycle at 94° C. 3 min, 61° C. 1 min, 72° C. 4 min, then for 30 cycles at 94° C. 1 min, 61° C. 1 min, 72° C. 4 min followed by 1 cycle at 94° C. 1 min, 61° C. 1 mm 72° C. 10 min. The PCR product was cut with SpeI and SacII, and cloned in the antisense direction into the pCMVneo vector precut with SacII and SpeI enzymes. Orientation of the hNr-CAM gene was confirmed by restriction digestion of specific enzymes. This clone was termed "pCMV-1/3Nr-AS".

A 1.3 Kb fragment of the hNr-CAM gene (spanning the first 1/3 part of the gene) was cloned in the antisense direction into precut pCMVneo vector (See FIG. 2D). This vector contains a constitutively active cytomegalovirus promoter and has been used in the past to over-express genes in cells (Huang, et al., 1997, *Int J Cancer*, 72:102–109). This clone was also termed "pCMV-1/3Nr-AS". The pCMV-neo or pCMV-1/3Nr-AS were then transfected into the 5GB glioblastoma cell line (ATCC# 2020-CRL), and selected in G418.

To obtain anti-sense Nr-CAM 2/3 clone, Nr-CAM 2/3 (corresponding to nucleotides 1410–2746 of FIG. 2A) was amplified using primers BT308 (5' TAGATACAACTAGT-CAATGCCTCTAATGAATATGGATA 3') SEQ. ID. No.: 20); and BT309 (5' AGATAGATCCGCGGAATAG-TAAATCCGATAGCCTTGTA 3') (SEQ. ID. No.: 21) cut with Spe I and Sac II, and cloned into precut pCMVneo vector cut with Sac II and Spe I enzymes.

7.1.2. Transfection of Glioblastoma (GB)

GB cells were plated at an approximate density of $3 \times 10^4$. 24 hours after plating the cells were washed with serum-free media and transfected with lipofectamine reagent plus plasmid DNA diluted in 1 ml total of serum-free media. Cells were incubated at 37° C. for hours after which the reagent was replaced with media containing 10% FBS. Cells were incubated at 37° C. for 72 hours. Media was changed adding 1000 μg/ml G418 a selective media to select for resistance to neomycynin (GIBCO-BRL). Cells were incubated at 37° C. for 72 hours. Media was changed adding 1000 μg/ml G418. Cells were incubated at 37° C. for 96 hours. Media was changed adding 1000 μg/ml G418. Cells were incubated at 37° C. for 72 hours. At this point all the cells in the control plate were dead. At this point, media was changed, adding 400 μg/ml G418. Cultures were maintained at 400 μg/ml G418 indefinitely, changing media every 72–96 hours.

7.1.3. Cell Morphology

During maintenance, cells transfected as described in Section 7.1.2 above, were split at a ratio of 1:2–1:3. After 72–96 hours, photographs of the cells were taken to compare the morphology.

7.1.4. Growth Assay

On Day 0, 5GB, 5GBpCMV neo, 5GBNr-CAM 1/3, 5GBNr-CAM 2/3 cells were trypsinized, counted on a Coulter Counter and plated at a density of $1 \times 10^4$ cells/60 mm dish. 12 plates of each condition were plated. At each time point 3 plates of each condition were counted on the Coulter Counter and the counts averaged.

7.1.5. Soft Agar Assay

Soft agar assay, a common in vitro phenotype of transformation, was performed as described previously (Huang et al., 1995, Cancer Research 55:5054–5062). Briefly, 5GB cells that were transfected with vector alone and with Nr-CAM in anti-sense direction were trypsinized. Approximately, $1 \times 10^5$ cell were mixed with 0.26% agar. Cells were then plated on top of a layer of 0.65% agar in 60 mm petri dishes and incubated 37° C. for 2 weeks. Cells were fed with one ml media containing 10% FBS after 1 week. Colonies were stained and counted under the inverted light microscope.

7.1.6. Northern Blot Analysis

PolyA+ mRNA was prepared from 5GB glioblastoma cells transfected with pCMVneo or pCMV-1/3Nr-AS cells using the Quick Prep mRNA Purification Kit (Pharmacia Biotech, Piscataway N.J.). 2 μg of polyA+ RNA was run in two lanes. Approximately $1 \times 10^6$ cpm/ml of labeled hNr-CAM probe was added to the blot and hybridized for 18 hours at 68° C. After washing in 0.1% SSC, 0.1% SDS, the blot was visualized using a Phosphor Imager (Molecular Dynamics) and the signal quantified using ImageQuant software (Molecular Dynamics). After quantification, the blot was stripped by incubating at 90° C. for 4 minutes in 0.1% SDS solution. The membrane was then prehybridized for 6 hours at 68° C. and then treated with a probe for β-actin at a concentration of $5 \times 10^5$ cpm/ml for 18 hours at 68° C. After washing, the blot was analyzed using the Phosphor Imager as described above. The volumes of the images for each probe were compared and normalized for β-actin signal.

7.2. Results

7.2.1. Effect of Expression of Anti-sense Nr-CAM on Morphology

To study the role of the Nr-CAM gene in cell transformation, Nr-CAM was over-expressed in 5GB cells in the anti-sense direction. The Nr-CAM antisense construct designated "Nr-1/3AS" was used. Approximately 10 μg of pure DNA was transfected onto two 60 mm-diameter petri-dishes containing 10,000 cells using lipofectamine (Gibco/BRL). Transfected cells were selected in G418 (1000 μg/ml) for 2 weeks. After 3 weeks, cells were maintained in 400 μg/ml G418. Cell morphology was observed under the inverted light microscope and cell proliferation properties of transfected cell were analyzed by counting cell number at various intervals. Results are presented in FIGS. 10A and B. FIG. 10A shows 5GB pCMVneo cells 96 hours after media change. FIG. 10B shows 5GBNr-CAM 1/3 cells 96 hours after media change. No change in cell growth and morphology was observed in glioblastoma cells transfected with pCMV-neo vector (control) but cells transfected with Nr-CAM 1/3 in anti-sense direction (pCMV-neoCA) showed a change in cell morphology and slower cell proliferation (see FIG. 10B). Our results indicate that Nr-CAM over-expression in the antisense direction blocked Nr-CAM gene further in the 5GB glioblastoma cell line. This result strongly suggests that Nr-CAM expression is required for continuous proliferation of 5GB cells.

In another set of experiments, the expression of antisense expression of Nr-CAM on GB morphology was evaluated in 5GB cells using the pCMV-1/3 Nr-AS construct. 5GB glioblastoma cells were plated at an approximate density of $3 \times 10^4$● 24 hours after plating the cells were washed with serum-free media and transfected with lipofectamine reagent plus plasmid DNA diluted in 1 ml total of serum-free media. Cells were incubated at 37° C. for 5 hours after which the reagent was replaced with media containing 10% FBS. Cells were incubated at 37° C. for 72 hours. Media was changed to the one containing 1000 µg/ml G418. Cells were incubated at 37° C. for 7 days. At this point, media was changed to the one containing 200 µg/ml G418. Cultures were maintained at 200 µg/ml G418 indefinitely, changing media every 72–96 hours. 96 hours after plating cells, photographs were taken to compare the morphology and are presented in FIGS. 15(A–D).

After transfection of antisense hNr-CAM (pCMV-1/3Nr-AS), glioblastoma cells were selected in G418 media for two weeks (1000 µg/ml). Untransfected 5GB cells (PCMV-neo) were used as controls. Cell morphology was compared between pCMV-neo or pCMV-1/3Nr-AS transfected cells after four weeks of selection. The glioblastoma cells transfected with antisense hNr-CAM became spindle shaped and showed neurite outgrowth (compare FIGS. 15A and B with FIGS. 15C and D). 5GB cells transfected with pCMV-1/3Nr-AS were grown in culture for 3 weeks and they demonstrated lack of density dependent inhibition of cell proliferation.

One unique observation in maintaining the hNr-CAM antisense transfected cells is that when fresh media containing 10% fetal bovine serum (FBS) is added to these cells, their morphology changes temporarily to one that is similar to pCMV-neo transfected 5GB cells. Both pCMV-neo and pCMV-1/3Nr-AS transfected cells were treated with different concentrations of serum (0.1, 1, 2 and 5% FBS). As shown in FIG. 16, 2% FBS is sufficient to cause a change in pCMV-1/3Nr-AS transfected 5GB cells similar to pCMV-neo transfected cells. No change in cell morphology was observed in cells transfected with pCMV-neo. This result suggests that one or a combination of more than one growth factors in the serum transiently reverses the morphology enforced by the anti-sense hNr-CAM.

7.2.2. Effect of Expression of Anti-Sense Nr-CAM on Cell Proliferation

The effect of Nr-CAM expression in the anti-sense direction on glioblastoma proliferation was evaluated as described above in Section 7.1 using anti-sense Nr-CAM 1/3 or pCMV-1/3Nr-AS. Results are illustrated in FIG. 11 and FIG. 17.

As shown in FIG. 11, expression of anti-sense Nr-CAM inhibited proliferation of GB cells compared to GB cells containing vector only (GB/pFCS).

As shown in FIG. 17, 5GB cells transfected with pCMV-1/3Nr-AS proliferate slowly as compared to pCMV-neo transfected cells. This result clearly demonstrates that hNr-CAM is required for continuous proliferation of cells. Even though 5GB cells transfected with pCMV-1/3Nr-AS proliferate slowly, they maintained their spindle shape morphology.

7.2.3. Soft Agar Colony Formation of Nr-CAM Antisense Expressing Cells

Results presented in FIG. 12 demonstrate that expression of Nr-CAM in the anti-sense direction (GM-Anti-Nr-CAM) inhibits the number of soft agar colonies compared to results observed with non-transfected GB cells (GB) and GB cells transfected with control plasmid only (GB-PFS). As illustrated, overexpression of antisense hNr-CAM caused 81% inhibition in number of soft agar colonies formed. Colonies formed by untransfected 5GB cells and control transfected 5GB cells with pCMV-neo were larger than those expressing hNr-CAM antisense.

7.2.4. Expression of Nr-CAM in hNr-CAM-Antisense Expressing Cells

The expression of hNr-CAM in cells expressing hNr-CAM antisense was evaluated using the Northern blot analysis technique described in Section 7.1.6.

As shown in FIG. 13, over-expression of the hNr-CAM anti-sense caused approximately 60% reduction in the native hNr-CAM expression. A logical explanation of this could be that in antisense hNr-CAM transfected cells, the natural transcript is made constitutively and a percentage of it is detected by Northern blot analysis regardless of RNase mediated degradation of antisense hNr-CAM bound to natural transcript (See FIG. 14).

7.2.5. Cell Cycle Analysis of Cells Expressing hNr-CAM Antisense

To study cell cycle status of 2CMV-neo and PCMV-1/3Nr-AS transfected cells, flow cytometry was performed on 5GB cell cycle status. Approximately $6 \times 10^6$ 5GB cells transfected with pCMVneo, or pCMV-Nr1/3AS cells were harvested by trypsinization followed by fixation in 80% ethanol (vol/vol) fixative (Sigma, St. Louis Mo.) and incubated for 24 hours at −20° C. The cells were then stained with Propidium Iodide for 30 minutes at room temperature in the dark. After filtering to remove debris, the cells were read on a FACS Calibur cell sorter (Becton Dickinson). Twenty thousand gated events were counted and the results analyzed using ModFit Lt 2.0 software (Becton Dickinson). Results are presented in Table 3.

TABLE 3

| EFFECT OF HNR-CAM ANTISENSE OVER-EXPRESSION | |
|---|---|
| CELL CYCLE PHASES | % OF CELLS |
| pCMV-neo Transfected Cells | |
| G0–G1 | 72.76 |
| G2–M | 10.00 |
| S | 17.24 |
| G2–G1 | 1.83 |
| pCMV-1/3Nr-AS Transfected Cells | |
| G0–G1 | 89.98 |
| G2–M | 3.66 |
| S | 6.36 |
| G2–G1 | 1.83 |

As shown in Table 3, a 63% decrease in S phase, 20% increase in G0-G1 phase and a 63.4% decrease in G2-M was observed in pCMV-1/3Nr-AS transfected cells as compared to pCMV-neo transfected cells. This set of results clearly demonstrates that antisense hNr-CAM causes a lengthening of specific phases of 5GB glioblastoma cells, i.e., causes lengthening of the cell cycle.

7.2.6. Effect of Antisense hNR-CAM on Migration and Invasion

Glioblastoma cells are highly invasive and they penetrate into surrounding normal brain tissue during their genesis (Kleihues and Cavenee, Pathology and genetics of tumors of the nervous system. Lyon, France: International Agency for Research on Cancer, 1997). To determine if antisense hNr-CAM could alter the migration capacity of glioblastoma cells, a cell migration assay was performed on 5GB cells transfected with pCMV-neo or pCMV-1/3Nr-AS. Equal number of cells ($1\times10^6$) were plated on a 8 μm pore size polycarbonate membrane filter. Cells that migrated through the membrane after 3 days were counted after fixation and staining with hematoxylin. Results are shown in FIG. 18.

As shown in FIG. 18, anti-sense hNr-CAM over-expression caused a 30% inhibition in the migration ability of 5GB glioblastoma cells.

In addition, an invasion assay was performed (See, Ridder and Calliauw, 1992, *Neurosurgery*, 31:1043–1048) to determine if antisense hNr-CAM could inhibit the invasion properties of glioblastoma cells.

Briefly, 825 ng of ECM gel was coated on to 8 μm pore size polycarbonate membrane filter. Equal number of 5GB cells ($1\times10^4$) were plated on to the ECM gel. Cells that migrated through the ECM gel after 4 and 7 days were counted after fixation and staining with hematoxylin. Results are presented in FIG. 19.

As shown in FIG. 19, approximately 90% inhibition of cell invasion was observed in pCMV-1/3Nr-AS transfected 5GB cells as compared to pCMV-neo transfected cells.

7.2.7. Effect of Radiation of Cells Antisense hNr-CAM

Tumor cells are in general more resistant to radiation. To determine if treatment antisense hNr-CAM transfected glioblastoma cells are UV radiation sensitive, the following experiment was conducted. Approximately $1\times10^4$ glioblastoma cell (transfected either with pCMV-neo or pCMV-1/3Nr-AS) were plated in triplicates in 60 mm diameter petridishes. Cells were then exposed to 100 units of UV radiation. As observed 65% of antisense hNr-CAM transfected cells died as compared to 27% death in pCMV-neo transfected cells.

The percentage of surviving cells undergoing apoptosis was also determined. To do so, the UV radiation experiment was repeated and cells undergoing apoptosis were identified using Apoptosis kit from BMB (Indianapolis, Iowa). Results are presented in FIG. 20.

As shown in FIG. 20C, a 17 fold increase in the number of cells undergoing apoptosis was observed. These results clearly suggest that antisense hNr-CAM over-expression caused 5GB glioblastoma cells to become more sensitive to UV radiation.

7.2.8. Antisense hNr-CAM Inhibits GB Tumor Growth In Vivo

In one experiment, designated "Experiment 1", 5 nude mice were subcutaneously with $3.0\times10^6$ 5GB glioblastoma cells (pCMV-neo or pCMV-1/3Nr-AS transfected). Results are presented in Table 4.

As shown in Table 4, tumor growth was observed in three of the five mice that were injected with 5GB (pCMV-neo transfected) cells. No tumor growth was observed in mice injected with pCMV-1/3Nr-AS transfected 5GB cells.

To increase the efficiency of this type of experiment, in another experiment, designated "Experiment 2", $1\times10^7$ 5GB cells (transfected with pCMV-neo or pCMV1/3Nr-AS) were injected into seven nude mice. Tumor size was measured 38 days post-injection. Results are presented in Table 4.

In Experiment 2, six of seven mice injected with cells transfected with pCMV-neo developed tumor. No tumor growth was observed in mice that were injected with cells transfected with pCMV-1/3Nr-AS vector.

Photographic illustration of three examples (each) of mice injected with pCMV-neo or pCMV-1/3Nr-AS vectors is presented in FIG. 21.

Results from this experiment clearly demonstrated that anti-sense hNr-CAM inhibits tumorigenic properties of 5GB glioblastoma cells in vivo. Injection of antisense hNr-CAM expressing glioblastoma cells caused inhibition of tumor formation.

TABLE 4

THE EFFECT OF ANTISENSE NNR-CAM
EXPRESSION ON TUMOR FORMATION IN VIVO

| Experiment 1 Mice injected (5 GB glioblastoma cells) | | Experiment 2 Mice injected (5 GB glioblastoma cells) | |
|---|---|---|---|
| pCMV-neo Tumor Volume (mm³) | pCMV1/3Nr-AS Tumor Volume (mm³) | pCMV-neo Tumor Volume (mm³) | pCMV1/3Nr-AS Tumor Volume (mm³) |
| 400 | NT | 75 | NT |
| 726 | NT | 650 | NT |
| 936 | NT | 63 | NT |
| NT | NT | 196 | NT |
| NT | NT | 365 | NT |
| | | 196 | NT |
| | | NT | NT |

NT = No Tumor
[1]= In experiment 1, tumor size was measured 70 days post injection.
[2]= In experiment 2, tumor size was measured 38 days post injection.

7.2.9. Intratumoral Inoculation of Plasmid-expressing Antisense hNR-CAM Caused Reduction in Glioblastoma Tumor Growth To determine if antisense hNr-CAM could cause reduction in tumor growth in vivo, the effect of direct intratumoral injection of an antisense hNr-CAM expressing plasmid mixed with liposomes was analyzed.

In a first set of experiments, three athymic nude mice were injected with $1\times10^5$ 5GB (glioblastoma) cells subcutaneously. 72 days post-implantation, 50 μg of either pCMVneo (control) (one animal) or pCMV1/3Nr-AS (two animals) plasmids were mixed with DMRIE (liopsomes) reagent (Gibco/BRL) and injected twice a week for four weeks around the tumor site. Tumor size was measured twice a week with a caliper and tumor volume was determined. Results are shown in FIG. 22A.

As demonstrated in FIG. 22A, animals which received anti-sense hNr-CAM injected directly into tmor showed not only slower tumor growth but also tumor regression compared to the control animal.

In another set of experiments, 20 athymic nude mice were implanted with 3×3 mm pieces of glioblastoma tumor. 28 days post implantation, 300 μg of either pCMVneo or pCMV1/3Nr-AS plasmids were mixed with DMRIE reagent (Gibco/BRL) to a final of 300 μl volume and injected twice a week for four weeks around the tumor. Control mice were injected with the same volume of 1×PBS or no treatment. Tumor size was measured twice a week with a caliper and tumor volume was determined. Results are shown in FIG. 22B.

As shown in FIG. 22B, direct intra-tumoral injection of plasmid expressing the antisense hNr-CAM caused slower tumor growth. Results from this set of experiments demonstrate that targeting of the hNr-CAM gene is an advantageous strategy for treating human glioblastoma tumors.

7.2.10. Role of hNr-CAM is not Confined to One Cell Line

As a model to study the role of hNr-CAM in malignant gliomas, we used the 5GB glioblastoma cell line. Glioblastoma tumor cells are heterogeneous and tumors isolated from different patients show different genetic characteristics. Thus, in order to demonstrate the fact that hNr-CAM is a good genetic target for gene therapy of human glioblastomas we demonstrated the anti-tumorigenic properties of anti-sense hNr-CAM in different glioblastoma cell lines.

Using the antisense hNr-CAM expressing vector (pCMV-1/3Nr-AS), we have not been able to block nHr-CAM expression in GB 1690 glioblastoma cells. This could possibly be due to cellular factors interfering with the binding of the antisense molecule to the appropriate site on hNr-CAM message.

To overcome this problem, we decided to target a different region of the hNr-CAM gene.

We have PCR amplified 1360 bases of the hNr-CAM gene (position 1410–2746) and cloned it in the antisense direction into precut pCMV-neo vector. This clone was termed as pCMV-2/3Nr-AS (Spanning the 2/3$^{rd}$ region of hNr-CAM gene). Preliminary results are shown in FIGS. 23(A–C).

The results obtained have demonstrated that pCMV-2/3Nr-AS transfected GB1690 cells changed in cell morphology and formed fewer numbers of soft agar colonies as compared to pCMV-neo transfected cells (FIG. 17).

On the basis of this result, it is concluded that hNr-CAM expression requirement for glioblastoma cell proliferation and tumorigenic properties is not confined to just one cell line.

7.2.11. Additional Studies

It is envisaged that anti-sense hNr-CAM can be overexpressed in other human malignant glioma cell lines, such as 1690-CRL, 16-HTB, 138-HTB and other species cells such as, e.g., two rat glioma cell lines, C6 glioma and 9L gliosarcoma. To demonstrate the fact that antisense human Nr-CAM can bind to rat Nr-CAM and inhibit its function, we performed a nucleotide sequence comparison between the rat and human Nr-CAM sequence. As shown in FIG. 24, 87% sequence similarity was observed between the human and rat Nr-CAM nucleotide sequence. On the basis of this result, we conclude that human Nr-CAM antisense molecule is capable of binding to rat Nr-CAM.

It is further envisaged that antisense phosphorothioate oligonucleotides can be used to inhibit the expression of hNr CAM in glioblastoma cells.

Antisense phosphorothioate oligonucleotides can be delivered effectively to several different regions of the brain using high-flow microinfusion technology. Targeting of the hNrCAM gene using antisense phosphorothioate oligonucleotides will be an effective way of treating human glioblastoma tumors in a clinical setting.

As a non-limiting illustrative example, the following is presented. Briefly, we have designed three phosphorothioate oligonucleotides (ODNs) against the translational initiation site of hNr-CAM (see Table 5 below).

Table 5 schematicly illustrates phosphorothioate oligonucleotides (ODAs) for hNr-CAM gene. ODNs H-1, H-2 and H-3 are designed against hNr-CAM; OL-4, OL-5 and OL-6 are random ODNs that can be used as controls. ATG sequence is indicated in bold. Three random ODNs that can serve as controls (OL-4, OL-5 and OL-6) are available commercially from Oliogos Etc. Inc. (Wilsonville, Oreg.).

The effect of ODNs on inhibition of hNr-CAM expression can be evaluated using the methodology described previously (Anfossi, et al., 1989 *Proc Natl Acad Sci USA*, 86:3379–3383). Briefly, 5GB, HTB-16 and GB1690 cells are plated per well in 96-well plates in media without ODNs. Twenty-four hours later, the culture media is changed to contain a final concentration of 1 mmole/L, 3 mmole/L, or 10 mmole/L ODNs. Control cultures received fresh culture media without ODNs. After 4–5 days post-transfection, cell proliferation is analyzed using a cell proliferation assay kit from Promega (Madison, Wis.). Expression is analyzed using immunocytochemistry methods, described previously (Sehgal, et al., 1998, *Int. J. Cancer,* 76(4):451–458). These oligonucleotides are tagged with fluorescent tags to ensure their entry into the cells.

TABLE 5

ILLUSTRATIVE ODN'S FOR hNr-CAM

| | | SEQ. ID. No. |
|---|---|---|
| 5'AGGAGTTAAGATGCTAATGCAGCTTAAAATA ATGCCGAAAAAGAAGCGCTTATCTGCGGGC3' | hNr-CAM | 22 |
| 3'TCCTCAATTCTACGATTAC5' | H-1 | 23 |
| 3'ACGTCGAATTTTATTACGGCT5' | H-2 | 24 |
| 3'TTCTTCGCGAATAGACG5' | H-3 | 25 |
| 5'ACTAGAGATACAGATCATAT3' | OL-4 | 26 |
| 5'CATATACGATCGATCGATGC3' | OL-5 | 27 |
| 5'GATAGTGCTGATCGATGCTA3' | OL-6 | 28 |

It is further envisaged that the expression of hNr-CAM gene can be blocked using a replication defective retroviral system to deliver antisense hNr-CAM. Replication defective retroviral systems have been used in the past to deliver genes to a variety of tumor cell types (see, Kondo, et al., 1998, Cancer Res. 68:962–967; Boviaisis, et al., 1994, Human Gene Ther. 5:183–191).

The current state of retroviral gene transfer technology stems from the coordinated design of retroviral vectors and packaging cell lines. The development of packaging cell lines that package retroviral RNAs into infectious particles without the concomitant production of replication-competent virus created a new level of safety and control. To do this, the structural genes necessary for particle formation and replication, gag, pol, and env, were integrated into cell lines without the RNA packaging signal, psi+. Subsequent introduction of a retroviral vector containing psi+, transcription and processing elements, and the gene of interest produces high-titer, replication-incompetent infectious virus. In other words, these retroviral particles can infect target cells and transmit the gene of interest, but cannot replicate within these cells since they lack the viral structural genes. The separate introduction and integration of the structural genes into the packaging cell line minimizes the chances of producing replication-competent virus due to recombination events during cell proliferation.

As a non-limiting, illustrative example the following is presented. A Retro-X™ system is used to deliver and over-express antisense hNr-CAM gene in glioblastoma cells. Retro-X™ system is a complete retroviral gene expression system that can transduce up to 100% of cells. Together with the RetroPack™, PT67 cell line, the Retro-X Vectors produce infectious, replication-incompetent retrovirus that can be used to introduce a gene of interest into a wide variety of mammalian cell types in vitro or in vivo. The highly efficient transduction machinery of retroviruses can stably integrate the cloned gene into the host genome of nearly all mitotically dividing cells. A retroviral vector containing the gene of interest (hNr-CAM) is first transfected into the packaging cell line. Antibiotic selection can then be used to obtain a population of cells that satably expresses the integrated vector and, if desired, high-titer clones can be isolated from this population. Virus produced by either stably transfected cells can be used to infect target cells.

The hNr-CAM gene (first 1.3 Kb) is cloned into the EcoRI and BamHI site of the pLXSN retroviral vector in antisense direction. Human hNr-CAM specific primers (BT306, 5' CATACG<u>AATTC</u>TAGATA CAACTAGTCTAATGCAGCT-TAAAATAATGCC 3' SEQ. ID. No.: 29; and BT307, 5' AGATAGATCCGCGGATATCCATATT CATTAGAG-GCATTG<u>GGATCC</u>CATAC 3' SEQ. ID. No.: 30) are used to PCR amplify 1/3$^{rd}$ portion of the hNr-CAM gene. PCR is carried out using Gene Amp PCR kit from Perkin Elmer (Branchburg, N.J.) under the following conditions: 4 μl of dNTP mix, 2 μl (100 mg/μl) each of hNr-CAM specific primers, 4 μl of 25 μM MgCl$_2$, 125 ng of cDNA template and 5 units of Amplitaq DNA polymerase. PCR amplification is carried out for 1 cycle at 94° C. 3 min, 61° C. 1 min, 72° C. 4 min, then for 30 cycles at 94° C. 1 min 61° C. 1 min, 72° C. 4 min followed by 1 cycle at 94° C. 1 min, 61° C. 1 min, 72° C. 10 min.

The PCR product is run on a 1% agarose gel. The band is then cut out and DNA was purified using gene clean system. DNA fragment is then digested with 5 units/μl EcoRI and BamHI for 2 hours at 37° C. Digested DNA is then run on a 2% agarose gel. The 1.3 Kb fragment is then cut out, purified and cloned in the antisense direction into EcoRI and BamHI sites of the pLXSN retroviral vector. Orientation of the cloned hNr-CAM gene is confirmed by sequencing. These particular plasmids containing hNr-CAM anti-sense direction are termed "pLXSN-1/3Nr-AS". PLXSN and pLXSN-1/3Nr vectors are transfected into Retropack™ PT67 cell line using the lipofectamine reagent. Cell lines are plated at a density of $3 \times 10^4$ cells/60 mm. Twenty four hours after plating the cells are washed with serum-free media and transfected with lipofectamine reagent plus plasmid DNA (5 μg) diluted in 1 ml of serum-free media. Cells are incubated at 37° C. for 5 hours after which the reagent is replaced with media containing 10% FBS and cultures were incubated at 37° C. for 72 hours. Media is then changed to an identical medium but containing adding 1000 μg/ml G418 and incubated at 37° C. for 96 hours. At this point, the medium is changed to one containing 200 μg/ml G418. Cultures are subsequently maintained in a medium containing 200 μg/ml G418, changing the medium every 72–96 hours. Retroviral particles are then harvested by aspirating the cell culture media into a sterile tube (approximately $10^5$–$10^6$ recombinant virus particles/ml).

Viral titer is then determined using a protocol recommended by Clontech. Human glioblastoma cell lines (5GB, 1690-CRL, 1620-CRL) and two rat glioma cell lines C6 and 9L gliosarcoma cells are plated at a density of $3 \times 10^5$ in two 100 mm plates. Viral particles harvested from PT67 cell line culture are filtered through a 0.45 μm filter and added on to human and rat glioma cell lines. Polybrene is added to a final concentration of 4μg/ml and incubated for 48 hours at 37° C. Cells are harvested and analyzed for hNr-CAM expression using Northern blot analysis. Cells that are expressing low levels of hNr-CAM are expanded in culture.

Northern blot analysis for the expression of hNr-CAM. Cell clones that are expressing low level of hNr-CAM are expanded in culture. Approximately $1 \times 10^7$ glioblastoma cells (1690-CRL, 1620-CRL, HTB-16, C6, 9L gliosarcoma) will be injected subcutaneously into the flanks often female athymic nude mice (two sites each). Tumor growth will be analyzed every week for at least fourteen weeks and compared between anti-sense hNr-CAM and mock infected glioma cell lines.

It is appreciated that the physiological conditions under which a tumor develops in brain can be quite different from when it develops subcutaneously. As a non-limiting, illustrative example, the following is presented. The effect of hNr-CAM (antisense in 1690-CRL, 1620-CRL, HTB-16, C6, 9L cells) on tumor formation in brain can be assessed as described previously for a mutant EGFR (Nishikawa, et al., 1994, Proc. Natl. Acad. Sci. USA 91:7727–7731). Briefly, $5 \times 10^5$ cells transfected or infected with the antisense hNr-CAM in 50–100 μl of 1×PBS are inoculated into the cerebral hemisphere (using stereotectic instrument) of eight nude mice for each cell line. As a positive control for tumor growth, U87MGΔEGFR cells that are known to form tumors in nude mice brains, can be used (Nishikawa, supra). $5 \times 10^5$ U87MGΔEGFR cells are inoculated into the cerebral hemisphere of nude mice. Another group of nude nice are injected with pCMV-neo transfected or mock infected 1690-CRL, 1620-CRL, HTB-16, C6, 9L cells. Brains from all of these mice are removed at two week intervals, embedded in OCT compound, frozen in liquid nitrogen and stored at –80° C. 6 μm sections are cut on a cryostat and immunocytochemistry are performed, for example, using the three markers described below.

GFAP (Glial Fibrillary Acidic Protein): Malignant glioma cells are known to cause gliosis of the surrounding tissue upon invasion (Mikkelsen, et al., 1998, Brain Tumor, Invasion, Bilogical, Clinical and Therapeutic Considerations, Wiley Liss, N.Y.). Thus, the tissue area at the edge of originally transplanted glioblastoma cells and the mice brain tissue, can be stained by performing immunocytochemistry for the GFAP protein. After recovery of the brain tissue it is embedded in OCT blocks. Several 6 μm sections are cut on a cryostat. After washing sections in 1×PBS buffer, 200 μm of diluted (1:80) rabbit anti-human GFAP are applied to slides. Slides are incubated for 18 hours at 4° C. in a humid chamber. After washing in 1×PBS, FITC conjugated anti-rabbit immunoglobulins (1:50) (DAKO, A/S, Denmark) are applied and the slides are incubated at 24° C. for 30 minutes in a humid chamber. Cells are washed with 1×PBS and then stained with Hematoxylin (Richard Allen Scientific, Richland Mich.) for 30 seconds. Slides are then treated with a clarifying agent (Richard Allen Scientific, Richland Mich.) for 2 seconds and then in bluing agent (Richard Allen Scientific, Richland Mich.). After washing in water, slides are coverslipped with 2% DABCO (Sigma, St. Louis Mo.) in 50% glycerol/1×PBS, and visualized with a Zeiss Axioskop UV microscope.

Cathepsin B (CB): CB is a cysteine protease that is expressed in gliomas directly in relation to grade of malignancy. CB is capable of degrading proteoglycans, a major component of the brain extracellular matrix, and could be involved in the process of glial tumor cell invasion into peritumoral normal brain (Mikkelsen, supra). Each of the inoculated glioma cells (GB1690, C6, 9L cells transfected with pCMV-neo or pCMV-1/3Nr-AS) can examined for CB expression by performing immunocytochemistry for CB protein. It has been shown that the relative degree of granular stain for glioma cell lines immunocytochemically in vivo correlates directly to the agree of invasiveness of the tumor displayed. To study the CB expression by immunocytochemistry, the same protocol as described above for the GEAP protein is followed. Human glioblastoma cell line U251MGn can be used as a positive control for CB staining.

Ki67: Ki67 is a protein that is expressed at high levels in actively dividing cells (Mikkelsen, supra). Immunocytochemistry can be performed on mouse brain sections against the Ki67 antigen using a rabbit anti-human antibody. The protocol for immunocytochemistry is the same as described above for the GFAP protein. U251MGn glioblastoma injected mice brain sections can be used as positive control for Ki67 specific staining. Direct comparison of the staining of these three markers provides the information about the extent of invasion of inoculated tumor cells.

8. EXAMPLE

Identification of Genes Altered by hNr-CAM

In order to identify genes that are altered by the hNr-Cam gene product in 5GB glioblastoma cells, we compared the expression of 5000 genes in pCMV-neo or pCMV-1/3Nr-AS transfected 5GB glioblastoma cells using the Array technique. Two identical Human GeneFilters™ were differentially hybridized with cDNA prepared from pCMV-neo or pCMV-1/3Nr-AS transfected 5GB glioblastoma cells. Two identical array membranes containing 5000 genes were purchased from Research Genetics. The membranes were prehybridized in a pre-hybridization solution for 12 hours. Hybridization was done with a $1 \times 10^5$ cpm/ml cDNA probe. This probe was prepared by carrying out 1st strand synthesis from pCMV-neo or pCMV-1/3Nr-AS transfected 5GB glioblastoma cells 1 µg polyA$^+$ mRNA. First strand cDNA synthesis was carried out using the Advantage cDNA synthesis kit from Clontech. The membranes were washed in a wash solution (0.1%SDS/1×SSC) for 30 minutes at room temperature and then at 50°. Membranes were then exposed to X-ray film. Results are presented in FIGS. 26(A and B).

As shown in FIGS. 26(A and B), two genes were identified that were differentially expressed. Selectin (endothelial adhesion molecule 2) was detected in pCMV-neo transfected cells (FIG. 26B) and not in pCMV-1/3Nr-AS (FIG. 26A) transfected 5GB cells. A novel gene (accession#H7785) was detected in pCMV-1/3Nr-AS (FIG. 26A) transfected and not in pCMV-neo transfected (FIG. 26B) 5GB cells. We are not only interested in exploring the role of these genes in glioblastoma cells in the context of hNr-CAM over-expression but also in understanding the mechanism by which hNr-CAM modulates the expression of these genes.

The present invention is not to be limited in scope by the microorganism deposited or the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

---

What is claimed is:

1. A method of inhibiting proliferation of a human tumor cell overexpressing Nr-CAM in a subject comprising administering locally to the subject, at the site or former site of a tumor, a Nr-CAM antisense nucleic acid comprising the complement of nucleotides 119 to 1434 of SEQ ID NO.: 1; wherein the human tumor cell overexpressing Nr-CAM is from a glioblastoma, a glioma, an astrocytoma, or an oligodendroglioma, and wherein the Nr-CAM antisense nucleic acid is administered in an amount effective to inhibit tumorigenesis by inhibiting proliferation of the human tumor cell overexpressing Nr-CAM.

2. The method according to claim 1 in which the subject is a human.

3. The method according to claim 1 in which the glioblastoma is glioblastoma multiforme.

4. The method of claim 1, wherein the local administration is by direct injection.

5. The method of claim 4, wherein the Nr-CAM antisense nucleic acid is administered locally by direct injection at the site or former site of the tumor.

6. The method of claim 5, wherein the administration is intratumoral.

7. A composition for the inhibition of tumorigenesis comprising a carrier and an antisense nucleic acid that comprises the complement of nucleotides 119 to 1434 of SEQ ID NO: 1 in an amount effective to inhibit tumorigenesis by inhibiting proliferation of a human tumor cell overexpressing Nr-CAM.

8. A composition for the inhibition of tumorigenesis comprising a carrier and an antisense nucleic acid that comprises the complement of nucleotides 1410 to 2746 of SEQ ID NO: 1 in an amount effective to inhibit tumorigenesis by inhibiting proliferation of a human tumor cell overexpressing Nr-CAM.

* * * * *

SEQUENCE LISTING

```
<160> NUMBER OF SEQ ID NOS: 32

<210> SEQ ID NO 1
<211> LENGTH: 4134
<212> TYPE: DNA
<213> ORGANISM: Homo sapiens
<220> FEATURE:
<221> NAME/KEY: CDS
<222> LOCATION: (130)..(4029)

<400> SEQUENCE: 1
cttcaaagtt ccccgcatga aaattactta aacgttgcac acaacgtttc agaaaatctt      60
ttgtgaaaga agaaaaggaa attcagtgtg tgagtctcag caggagttaa gctaatgcag     120 cttaaaata atg ccg aaa aag aag cgc tta tct gcg ggc aga gtg ccc ctg    171
         Met Pro Lys Lys Lys Arg Leu Ser Ala Gly Arg Val Pro Leu
           1               5                  10 att ctc ttc ctg tgc cag atg att agt gca ctg gaa gta cct ctt gat      219
Ile Leu Phe Leu Cys Gln Met Ile Ser Ala Leu Glu Val Pro Leu Asp
 15              20                  25                  30 cca aaa ctt ctt gaa gac ttg gta cag cct cca acc atc acc caa cag      267
Pro Lys Leu Leu Glu Asp Leu Val Gln Pro Pro Thr Ile Thr Gln Gln
                 35                  40                  45 tct cca aaa gat tac att att gac cct cgg gag aat att gta atc cag      315
Ser Pro Lys Asp Tyr Ile Ile Asp Pro Arg Glu Asn Ile Val Ile Gln
             50                  55                  60
```

-continued

| | | |
|---|---|---|
| tgt gaa gcc aaa ggg aaa ccg ccc cca agc ttt tcc tgg acc cgt aat<br>Cys Glu Ala Lys Gly Lys Pro Pro Pro Ser Phe Ser Trp Thr Arg Asn<br>        65                        70                       75 | 363 | |
| ggg act cat ttt gac atc gat aaa gac cct ctg gtc acc atg aag cct<br>Gly Thr His Phe Asp Ile Asp Lys Asp Pro Leu Val Thr Met Lys Pro<br>    80                        85                       90 | 411 | |
| ggc aca gga acg ctc ata att aac atc atg agc gaa ggg aaa gct gag<br>Gly Thr Gly Thr Leu Ile Ile Asn Ile Met Ser Glu Gly Lys Ala Glu<br>95                     100                   105                 110 | 459 | |
| acc tat gaa gga gtc tat cag tgt aca gca agg aac gaa cgc gga gct<br>Thr Tyr Glu Gly Val Tyr Gln Cys Thr Ala Arg Asn Glu Arg Gly Ala<br>                  115                   120                 125 | 507 | |
| gca gtt tct aat aac att gtt gtc cgc cca tcc aga tca cca ttg tgg<br>Ala Val Ser Asn Asn Ile Val Val Arg Pro Ser Arg Ser Pro Leu Trp<br>          130                   135                 140 | 555 | |
| acc aaa gaa aaa ctt gaa cca atc aca ctt caa agt ggt cag tct tta<br>Thr Lys Glu Lys Leu Glu Pro Ile Thr Leu Gln Ser Gly Gln Ser Leu<br>               145                   150                 155 | 603 | |
| gta ctt ccc tgc aga ccc cca att gga tta cca cca cct ata ata ttt<br>Val Leu Pro Cys Arg Pro Pro Ile Gly Leu Pro Pro Pro Ile Ile Phe<br>160                   165                   170 | 651 | |
| tgg atg gat aat tcc ttt caa aga ctt cca caa agt gag aga gtt tct<br>Trp Met Asp Asn Ser Phe Gln Arg Leu Pro Gln Ser Glu Arg Val Ser<br>175                     180                   185                 190 | 699 | |
| caa ggt ttg aat ggg gac ctt tat ttt tcc aat gtc ctc cca gag gac<br>Gln Gly Leu Asn Gly Asp Leu Tyr Phe Ser Asn Val Leu Pro Glu Asp<br>                  195                   200                 205 | 747 | |
| acc cgc gaa gac tat atc tgt tat gct aga ttt aat cat act caa acc<br>Thr Arg Glu Asp Tyr Ile Cys Tyr Ala Arg Phe Asn His Thr Gln Thr<br>          210                   215                 220 | 795 | |
| ata cag cag aag caa cct att tct gtg aag gtg att tca gtg gat gaa<br>Ile Gln Gln Lys Gln Pro Ile Ser Val Lys Val Ile Ser Val Asp Glu<br>               225                   230                 235 | 843 | |
| ttg aat gac act ata gct gct aat ttg agt gac act gag ttt tat ggt<br>Leu Asn Asp Thr Ile Ala Ala Asn Leu Ser Asp Thr Glu Phe Tyr Gly<br>240                   245                   250 | 891 | |
| gct aaa tca agt aga gag agg cca cca aca ttt tta act cca gaa ggc<br>Ala Lys Ser Ser Arg Glu Arg Pro Pro Thr Phe Leu Thr Pro Glu Gly<br>255                     260                   265                 270 | 939 | |
| aat gca agt aac aaa gag gaa tta aga gga aat gtg ctt tca ctg gag<br>Asn Ala Ser Asn Lys Glu Glu Leu Arg Gly Asn Val Leu Ser Leu Glu<br>               275                   280                 285 | 987 | |
| tgc att gca gaa gga ctg cct acc cca att att tac tgg gca aag gaa<br>Cys Ile Ala Glu Gly Leu Pro Thr Pro Ile Ile Tyr Trp Ala Lys Glu<br>          290                   295                 300 | 1035 | |
| gat gga atg cta ccc aaa aac agg aca gtt tat aag aac ttt gag aaa<br>Asp Gly Met Leu Pro Lys Asn Arg Thr Val Tyr Lys Asn Phe Glu Lys<br>               305                   310                 315 | 1083 | |
| acc ttg cag atc att cat gtt tca gaa gca gac tct gga aat tac caa<br>Thr Leu Gln Ile Ile His Val Ser Glu Ala Asp Ser Gly Asn Tyr Gln<br>320                   325                   330 | 1131 | |
| tgt ata gca aaa aat gca tta gga gcc atc cac cat acc att tct gtt<br>Cys Ile Ala Lys Asn Ala Leu Gly Ala Ile His His Thr Ile Ser Val<br>335                     340                   345                 350 | 1179 | |
| aga gtt aaa gcg gct cca tac tgg atc aca gcc cct caa aat ctt gtg<br>Arg Val Lys Ala Ala Pro Tyr Trp Ile Thr Ala Pro Gln Asn Leu Val<br>               355                   360                 365 | 1227 | |
| ctg tcc cca gga gag gat ggg acc ttg atc tgc aga gct aat ggc aac<br>Leu Ser Pro Gly Glu Asp Gly Thr Leu Ile Cys Arg Ala Asn Gly Asn | 1275 | |

-continued

```
                    370                 375                 380
ccc aaa ccc aga att agc tgg tta aca aat gga gtc cca ata gaa att      1323
Pro Lys Pro Arg Ile Ser Trp Leu Thr Asn Gly Val Pro Ile Glu Ile
        385                 390                 395 gcc cct gat gac ccc agc aga aaa ata gat ggc gat acc att att ttt      1371
Ala Pro Asp Asp Pro Ser Arg Lys Ile Asp Gly Asp Thr Ile Ile Phe
400                 405                 410 tca aat gtt caa gaa aga tca agt gca gta tat cag tgc aat gcc tct      1419
Ser Asn Val Gln Glu Arg Ser Ser Ala Val Tyr Gln Cys Asn Ala Ser
    415                 420                 425                 430 aat gaa tat gga tat tta ctg gca aac gca ttt gta aat gtg ctg gct      1467
Asn Glu Tyr Gly Tyr Leu Leu Ala Asn Ala Phe Val Asn Val Leu Ala
                435                 440                 445 gag cca cca cga atc ctc aca cct gca aac aca ctc tac cag gtc att      1515
Glu Pro Pro Arg Ile Leu Thr Pro Ala Asn Thr Leu Tyr Gln Val Ile
            450                 455                 460 gca aac agg cct gct tta cta gac tgt gcc ttc ttt ggg tct cct ctc      1563
Ala Asn Arg Pro Ala Leu Leu Asp Cys Ala Phe Phe Gly Ser Pro Leu
        465                 470                 475 cca acc atc gag tgg ttt aaa gga gct aaa gga agt gct ctt cat gaa      1611
Pro Thr Ile Glu Trp Phe Lys Gly Ala Lys Gly Ser Ala Leu His Glu
    480                 485                 490 gat att tat gtt tta cat gaa aat gga act ttg gaa atc aaa gat gct      1659
Asp Ile Tyr Val Leu His Glu Asn Gly Thr Leu Glu Ile Lys Asp Ala
495                 500                 505                 510 aca tgg atc gtt aaa gaa att cct gtg gcc caa aag gac agt aca gga      1707
Thr Trp Ile Val Lys Glu Ile Pro Val Ala Gln Lys Asp Ser Thr Gly
                515                 520                 525 act tat acg tgt gtt gca agg aat aaa tta ggg atg gca aag aat gaa      1755
Thr Tyr Thr Cys Val Ala Arg Asn Lys Leu Gly Met Ala Lys Asn Glu
            530                 535                 540 gtt cac tta cag ccc gaa tat gca gtt gtg caa aga ggg agc atg gtg      1803
Val His Leu Gln Pro Glu Tyr Ala Val Val Gln Arg Gly Ser Met Val
        545                 550                 555 tcc ttt gaa tgc aaa gtg aaa cat gat cac acc tta tcc ctc act gtc      1851
Ser Phe Glu Cys Lys Val Lys His Asp His Thr Leu Ser Leu Thr Val
    560                 565                 570 ctg tgg ctg aag gac aac agg gaa ctg ccc agt gat gaa agg ttc act      1899
Leu Trp Leu Lys Asp Asn Arg Glu Leu Pro Ser Asp Glu Arg Phe Thr
575                 580                 585                 590 gtt gac aag gat cat cta gtg gta gct gat gtc agt gac gat gac agc      1947
Val Asp Lys Asp His Leu Val Val Ala Asp Val Ser Asp Asp Asp Ser
                595                 600                 605 ggg acc tac acg tgt gtg gcc aac acc act ctg gac agc gtc tcc gcc      1995
Gly Thr Tyr Thr Cys Val Ala Asn Thr Thr Leu Asp Ser Val Ser Ala
            610                 615                 620 agc gct gtg ctt agc gtt gtt gct cct act cca act cca gct ccc gtt      2043
Ser Ala Val Leu Ser Val Val Ala Pro Thr Pro Thr Pro Ala Pro Val
        625                 630                 635 tac gat gtc cca aat cct ccc ttt gac tta gaa ctg aca gat caa ctt      2091
Tyr Asp Val Pro Asn Pro Pro Phe Asp Leu Glu Leu Thr Asp Gln Leu
    640                 645                 650 gac aaa agt gtt cag ctg tca tgg acc cca ggc gat gac aac aat agc      2139
Asp Lys Ser Val Gln Leu Ser Trp Thr Pro Gly Asp Asp Asn Asn Ser
655                 660                 665                 670 ccc att aca aaa ttc atc atc gaa tat gaa gat gca atg cac aag cca      2187
Pro Ile Thr Lys Phe Ile Ile Glu Tyr Glu Asp Ala Met His Lys Pro
                675                 680                 685 ggg ctg tgg cac cac caa act gaa gtt tct gga aca cag acc aca gcc      2235
Gly Leu Trp His His Gln Thr Glu Val Ser Gly Thr Gln Thr Thr Ala
```

-continued

```
Gly Leu Trp His His Gln Thr Glu Val Ser Gly Thr Gln Thr Thr Ala
            690                 695                 700 cag ctg aag ctg tct cct tac gtg aac tac tcc ttc cgc gtg atg gca      2283
Gln Leu Lys Leu Ser Pro Tyr Val Asn Tyr Ser Phe Arg Val Met Ala
            705                 710                 715 gtg aac agc att ggg aag agc ttg ccc agc gag gcg tct gag cag tat      2331
Val Asn Ser Ile Gly Lys Ser Leu Pro Ser Glu Ala Ser Glu Gln Tyr
            720                 725                 730 ttg acg aaa gcc tca gaa cca gat aaa aac ccc aca gct gtg gaa gga      2379
Leu Thr Lys Ala Ser Glu Pro Asp Lys Asn Pro Thr Ala Val Glu Gly
735                 740                 745                 750 ctg gga tca gag cct gat aat ttg gag att acg tgg aag ccc ttg aat      2427
Leu Gly Ser Glu Pro Asp Asn Leu Glu Ile Thr Trp Lys Pro Leu Asn
            755                 760                 765 ggt ttc gaa tct aat ggg cca ggc ctt cag tac aaa gtt agc tgg cgc      2475
Gly Phe Glu Ser Asn Gly Pro Gly Leu Gln Tyr Lys Val Ser Trp Arg
            770                 775                 780 cag aaa gat ggt gat gat gaa tgg aca tct gtg gtt gtg gca aat gta      2523
Gln Lys Asp Gly Asp Asp Glu Trp Thr Ser Val Val Val Ala Asn Val
            785                 790                 795 tcc aaa tat att gtc tca ggc acg cca acc ttt gtt cca tac ctg atc      2571
Ser Lys Tyr Ile Val Ser Gly Thr Pro Thr Phe Val Pro Tyr Leu Ile
            800                 805                 810 aaa gtt cag gcc ctg aat gac atg ggg ttt gcc ccc gag cca gct gta      2619
Lys Val Gln Ala Leu Asn Asp Met Gly Phe Ala Pro Glu Pro Ala Val
815                 820                 825                 830 gtc atg gga cat tct gga gaa gac ctc cca atg gtg gct cct ggg aac      2667
Val Met Gly His Ser Gly Glu Asp Leu Pro Met Val Ala Pro Gly Asn
            835                 840                 845 gtg cgt gtg aat gtg gtg aac agt acc tta gcc gag gtg cac tgg gac      2715
Val Arg Val Asn Val Val Asn Ser Thr Leu Ala Glu Val His Trp Asp
            850                 855                 860 cca gta cct ctg aaa agc atc cga gga cac cta caa ggc tat cgg att      2763
Pro Val Pro Leu Lys Ser Ile Arg Gly His Leu Gln Gly Tyr Arg Ile
            865                 870                 875 tac tat tgg aag acc cag agt tca tct aaa aga aac aga cgt cac att      2811
Tyr Tyr Trp Lys Thr Gln Ser Ser Ser Lys Arg Asn Arg Arg His Ile
            880                 885                 890 gag aaa aag atc ctc acc ttc caa ggc agc aag act cat ggc atg ttg      2859
Glu Lys Lys Ile Leu Thr Phe Gln Gly Ser Lys Thr His Gly Met Leu
895                 900                 905                 910 ccg ggg cta gag ccc ttt agc cac tac aca ctg aat gtc cga gtg gtc      2907
Pro Gly Leu Glu Pro Phe Ser His Tyr Thr Leu Asn Val Arg Val Val
            915                 920                 925 aat ggg aaa ggg gag ggc cca gcc agc cct gac aga gtc ttt aat act      2955
Asn Gly Lys Gly Glu Gly Pro Ala Ser Pro Asp Arg Val Phe Asn Thr
            930                 935                 940 cca gaa gga gtc ccc agt gct ccc tcg tct ttg aag att gtg aat cca      3003
Pro Glu Gly Val Pro Ser Ala Pro Ser Ser Leu Lys Ile Val Asn Pro
945                 950                 955 aca ctg gac tct ctc act ttg gaa tgg gat cca ccg agc cac ccg aat      3051
Thr Leu Asp Ser Leu Thr Leu Glu Trp Asp Pro Pro Ser His Pro Asn
            960                 965                 970 ggc att ttg aca gag tac acc tta aag tat cag cca att aac agc aca      3099
Gly Ile Leu Thr Glu Tyr Thr Leu Lys Tyr Gln Pro Ile Asn Ser Thr
975                 980                 985                 990 cat gaa tta ggc cct ctg gta gat ttg aaa att cct gcc aac aag aca      3147
His Glu Leu Gly Pro Leu Val Asp Leu Lys Ile Pro Ala Asn Lys Thr
            995                 1000                1005
```

-continued

| | |
|---|---|
| cgg tgg act tta aaa aat tta aat ttc agc act cga tat aag ttt tat<br>Arg Trp Thr Leu Lys Asn Leu Asn Phe Ser Thr Arg Tyr Lys Phe Tyr<br>        1010                 1015                 1020 | 3195 |
| ttc tat gca caa aca tca gca gga tca gga agt caa att aca gag gaa<br>Phe Tyr Ala Gln Thr Ser Ala Gly Ser Gly Ser Gln Ile Thr Glu Glu<br>        1025                 1030                 1035 | 3243 |
| gca gta aca act gtg gat gaa gct ggt att ctt cca cct gat gta ggt<br>Ala Val Thr Thr Val Asp Glu Ala Gly Ile Leu Pro Pro Asp Val Gly<br>1040                 1045                 1050 | 3291 |
| gca ggc aaa gtt caa gct gta aat acc agg atc agc aat ctt act gct<br>Ala Gly Lys Val Gln Ala Val Asn Thr Arg Ile Ser Asn Leu Thr Ala<br>1055                 1060                 1065                 1070 | 3339 |
| gca gct gct gag acc tat gcc aat atc agt tgg gaa tat gag gga cca<br>Ala Ala Ala Glu Thr Tyr Ala Asn Ile Ser Trp Glu Tyr Glu Gly Pro<br>        1075                 1080                 1085 | 3387 |
| gag cat gtg aac ttt tat gtt gaa tat ggt gta gca ggc agc aaa gaa<br>Glu His Val Asn Phe Tyr Val Glu Tyr Gly Val Ala Gly Ser Lys Glu<br>        1090                 1095                 1100 | 3435 |
| gaa tgg aga aaa gaa att gta aat ggt tct cgg agc ttc ttt ggg tta<br>Glu Trp Arg Lys Glu Ile Val Asn Gly Ser Arg Ser Phe Phe Gly Leu<br>        1105                 1110                 1115 | 3483 |
| aag ggt cta atg cca gga aca gca tac aaa gtt cga gtt ggt gct gtg<br>Lys Gly Leu Met Pro Gly Thr Ala Tyr Lys Val Arg Val Gly Ala Val<br>        1120                 1125                 1130 | 3531 |
| ggg gac tct ggt ttt gtg agt tca gag gat gtg ttt gag aca ggc cca<br>Gly Asp Ser Gly Phe Val Ser Ser Glu Asp Val Phe Glu Thr Gly Pro<br>1135                 1140                 1145                 1150 | 3579 |
| gcg atg gca agc cgg cag gtg gat att gca act cag ggc tgg ttc att<br>Ala Met Ala Ser Arg Gln Val Asp Ile Ala Thr Gln Gly Trp Phe Ile<br>        1155                 1160                 1165 | 3627 |
| ggt ctg atg tgt gct gtt gct ctc ctt atc tta att ttg ctg att gtt<br>Gly Leu Met Cys Ala Val Ala Leu Leu Ile Leu Ile Leu Leu Ile Val<br>        1170                 1175                 1180 | 3675 |
| tgc ttc atc aga aga aac aag ggt ggt aaa tat cca gtt aaa gaa aag<br>Cys Phe Ile Arg Arg Asn Lys Gly Gly Lys Tyr Pro Val Lys Glu Lys<br>        1185                 1190                 1195 | 3723 |
| gaa gat gcc cat gct gac cct gaa atc cag cct atg aag gaa gat gat<br>Glu Asp Ala His Ala Asp Pro Glu Ile Gln Pro Met Lys Glu Asp Asp<br>1200                 1205                 1210 | 3771 |
| ggg aca ttt gga gaa tac agt gat gca gaa gac cac aag cct ttg aaa<br>Gly Thr Phe Gly Glu Tyr Ser Asp Ala Glu Asp His Lys Pro Leu Lys<br>1215                 1220                 1225                 1230 | 3819 |
| aaa gga agt cga act cct tca gac agg act gtg aaa aaa gaa gat agt<br>Lys Gly Ser Arg Thr Pro Ser Asp Arg Thr Val Lys Lys Glu Asp Ser<br>        1235                 1240                 1245 | 3867 |
| gac gac agc cta gtt gac tat gga gaa ggg gtt aat ggc cag ttc aat<br>Asp Asp Ser Leu Val Asp Tyr Gly Glu Gly Val Asn Gly Gln Phe Asn<br>        1250                 1255                 1260 | 3915 |
| gag gat ggc tcc ttt att gga caa tac agt ggt aag aaa gag aaa gag<br>Glu Asp Gly Ser Phe Ile Gly Gln Tyr Ser Gly Lys Lys Glu Lys Glu<br>        1265                 1270                 1275 | 3963 |
| ccg gct gaa gga aac gaa agc tca gag gca cct tct cct gtc aac gcc<br>Pro Ala Glu Gly Asn Glu Ser Ser Glu Ala Pro Ser Pro Val Asn Ala<br>1280                 1285                 1290 | 4011 |
| atg aat tcc ttt gtt taa tttttaagct caaagccaat attccatttc<br>Met Asn Ser Phe Val<br>1295                 1300 | 4059 |
| tctagaatgt ttatcctaag ctcttgtttg tcagccctct catactatga acatatgggt | 4119 |
| agagagtata ttttc | 4134 |

<210> SEQ ID NO 2
<211> LENGTH: 1299
<212> TYPE: PRT
<213> ORGANISM: Homo sapiens

<400> SEQUENCE: 2

```
Met Pro Lys Lys Arg Leu Ser Ala Gly Arg Val Pro Leu Ile Leu
 1               5                  10                  15

Phe Leu Cys Gln Met Ile Ser Ala Leu Glu Val Pro Leu Asp Pro Lys
             20                  25                  30

Leu Leu Glu Asp Leu Val Gln Pro Thr Ile Thr Gln Gln Ser Pro
             35                  40                  45

Lys Asp Tyr Ile Ile Asp Pro Arg Glu Asn Ile Val Ile Gln Cys Glu
         50                  55                  60

Ala Lys Gly Lys Pro Pro Ser Phe Ser Trp Thr Arg Asn Gly Thr
 65                  70                  75                  80

His Phe Asp Ile Asp Lys Asp Pro Leu Val Thr Met Lys Pro Gly Thr
                 85                  90                  95

Gly Thr Leu Ile Ile Asn Ile Met Ser Glu Gly Lys Ala Glu Thr Tyr
                100                 105                 110

Glu Gly Val Tyr Gln Cys Thr Ala Arg Asn Glu Arg Gly Ala Ala Val
            115                 120                 125

Ser Asn Asn Ile Val Val Arg Pro Ser Arg Ser Pro Leu Trp Thr Lys
130                 135                 140

Glu Lys Leu Glu Pro Ile Thr Leu Gln Ser Gly Gln Ser Leu Val Leu
145                 150                 155                 160

Pro Cys Arg Pro Pro Ile Gly Leu Pro Pro Ile Ile Phe Trp Met
                165                 170                 175

Asp Asn Ser Phe Gln Arg Leu Pro Gln Ser Glu Arg Val Ser Gln Gly
                180                 185                 190

Leu Asn Gly Asp Leu Tyr Phe Ser Asn Val Leu Pro Glu Asp Thr Arg
            195                 200                 205

Glu Asp Tyr Ile Cys Tyr Ala Arg Phe Asn His Thr Gln Thr Ile Gln
    210                 215                 220

Gln Lys Gln Pro Ile Ser Val Lys Val Ile Ser Val Asp Glu Leu Asn
225                 230                 235                 240

Asp Thr Ile Ala Ala Asn Leu Ser Asp Thr Glu Phe Tyr Gly Ala Lys
                245                 250                 255

Ser Ser Arg Glu Arg Pro Pro Thr Phe Leu Thr Pro Glu Gly Asn Ala
            260                 265                 270

Ser Asn Lys Glu Glu Leu Arg Gly Asn Val Leu Ser Leu Glu Cys Ile
        275                 280                 285

Ala Glu Gly Leu Pro Thr Pro Ile Ile Tyr Trp Ala Lys Glu Asp Gly
    290                 295                 300

Met Leu Pro Lys Asn Arg Thr Val Tyr Lys Asn Phe Glu Lys Thr Leu
305                 310                 315                 320

Gln Ile Ile His Val Ser Glu Ala Asp Ser Gly Asn Tyr Gln Cys Ile
                325                 330                 335

Ala Lys Asn Ala Leu Gly Ala Ile His His Thr Ile Ser Val Arg Val
            340                 345                 350

Lys Ala Ala Pro Tyr Trp Ile Thr Ala Pro Gln Asn Leu Val Leu Ser
        355                 360                 365

Pro Gly Glu Asp Gly Thr Leu Ile Cys Arg Ala Asn Gly Asn Pro Lys
```

```
                      370             375             380
Pro Arg Ile Ser Trp Leu Thr Asn Gly Val Pro Ile Glu Ile Ala Pro
385                 390                 395                 400

Asp Asp Pro Ser Arg Lys Ile Asp Gly Asp Thr Ile Ile Phe Ser Asn
                405                 410                 415

Val Gln Glu Arg Ser Ser Ala Val Tyr Gln Cys Asn Ala Ser Asn Glu
                420                 425                 430

Tyr Gly Tyr Leu Leu Ala Asn Ala Phe Val Asn Val Leu Ala Glu Pro
                435                 440                 445

Pro Arg Ile Leu Thr Pro Ala Asn Thr Leu Tyr Gln Val Ile Ala Asn
450                 455                 460

Arg Pro Ala Leu Leu Asp Cys Ala Phe Phe Gly Ser Pro Leu Pro Thr
465                 470                 475                 480

Ile Glu Trp Phe Lys Gly Ala Lys Gly Ser Ala Leu His Glu Asp Ile
                485                 490                 495

Tyr Val Leu His Glu Asn Gly Thr Leu Glu Ile Lys Asp Ala Thr Trp
                500                 505                 510

Ile Val Lys Glu Ile Pro Val Ala Gln Lys Asp Ser Thr Gly Thr Tyr
                515                 520                 525

Thr Cys Val Ala Arg Asn Lys Leu Gly Met Ala Lys Asn Glu Val His
                530                 535                 540

Leu Gln Pro Glu Tyr Ala Val Val Gln Arg Gly Ser Met Val Ser Phe
545                 550                 555                 560

Glu Cys Lys Val Lys His Asp His Thr Leu Ser Leu Thr Val Leu Trp
                565                 570                 575

Leu Lys Asp Asn Arg Glu Leu Pro Ser Asp Glu Arg Phe Thr Val Asp
                580                 585                 590

Lys Asp His Leu Val Val Ala Asp Val Ser Asp Asp Ser Gly Thr
                595                 600                 605

Tyr Thr Cys Val Ala Asn Thr Thr Leu Asp Ser Val Ser Ala Ser Ala
                610                 615                 620

Val Leu Ser Val Val Ala Pro Thr Pro Thr Pro Ala Pro Val Tyr Asp
625                 630                 635                 640

Val Pro Asn Pro Pro Phe Asp Leu Glu Leu Thr Asp Gln Leu Asp Lys
                645                 650                 655

Ser Val Gln Leu Ser Trp Thr Pro Gly Asp Asp Asn Asn Ser Pro Ile
                660                 665                 670

Thr Lys Phe Ile Ile Glu Tyr Glu Asp Ala Met His Lys Pro Gly Leu
                675                 680                 685

Trp His His Gln Thr Glu Val Ser Gly Thr Gln Thr Thr Ala Gln Leu
                690                 695                 700

Lys Leu Ser Pro Tyr Val Asn Tyr Ser Phe Arg Val Met Ala Val Asn
705                 710                 715                 720

Ser Ile Gly Lys Ser Leu Pro Ser Glu Ala Ser Glu Gln Tyr Leu Thr
                725                 730                 735

Lys Ala Ser Glu Pro Asp Lys Asn Pro Thr Ala Val Glu Gly Leu Gly
                740                 745                 750

Ser Glu Pro Asp Asn Leu Glu Ile Thr Trp Lys Pro Leu Asn Gly Phe
                755                 760                 765

Glu Ser Asn Gly Pro Gly Leu Gln Tyr Lys Val Ser Trp Arg Gln Lys
                770                 775                 780

Asp Gly Asp Asp Glu Trp Thr Ser Val Val Val Ala Asn Val Ser Lys
785                 790                 795                 800
```

-continued

```
Tyr Ile Val Ser Gly Thr Pro Thr Phe Val Pro Tyr Leu Ile Lys Val
            805                 810                 815
Gln Ala Leu Asn Asp Met Gly Phe Ala Pro Glu Pro Ala Val Val Met
            820                 825                 830
Gly His Ser Gly Glu Asp Leu Pro Met Val Ala Pro Gly Asn Val Arg
            835                 840                 845
Val Asn Val Val Asn Ser Thr Leu Ala Glu Val His Trp Asp Pro Val
            850                 855                 860
Pro Leu Lys Ser Ile Arg Gly His Leu Gln Gly Tyr Arg Ile Tyr Tyr
865                 870                 875                 880
Trp Lys Thr Gln Ser Ser Ser Lys Arg Asn Arg Arg His Ile Glu Lys
            885                 890                 895
Lys Ile Leu Thr Phe Gln Gly Ser Lys Thr His Gly Met Leu Pro Gly
            900                 905                 910
Leu Glu Pro Phe Ser His Tyr Thr Leu Asn Val Arg Val Val Asn Gly
            915                 920                 925
Lys Gly Glu Gly Pro Ala Ser Pro Asp Arg Val Phe Asn Thr Pro Glu
            930                 935                 940
Gly Val Pro Ser Ala Pro Ser Ser Leu Lys Ile Val Asn Pro Thr Leu
945                 950                 955                 960
Asp Ser Leu Thr Leu Glu Trp Asp Pro Ser His Pro Asn Gly Ile
            965                 970                 975
Leu Thr Glu Tyr Thr Leu Lys Tyr Gln Pro Ile Asn Ser Thr His Glu
            980                 985                 990
Leu Gly Pro Leu Val Asp Leu Lys Ile Pro Ala Asn Lys Thr Arg Trp
            995                 1000                1005
Thr Leu Lys Asn Leu Asn Phe Ser Thr Arg Tyr Lys Phe Tyr Phe Tyr
            1010                1015                1020
Ala Gln Thr Ser Ala Gly Ser Gly Ser Gln Ile Thr Glu Glu Ala Val
1025                1030                1035                1040
Thr Thr Val Asp Glu Ala Gly Ile Leu Pro Pro Asp Val Gly Ala Gly
                    1045                1050                1055
Lys Val Gln Ala Val Asn Thr Arg Ile Ser Asn Leu Thr Ala Ala Ala
            1060                1065                1070
Ala Glu Thr Tyr Ala Asn Ile Ser Trp Glu Tyr Glu Gly Pro Glu His
            1075                1080                1085
Val Asn Phe Tyr Val Glu Tyr Gly Val Ala Gly Ser Lys Glu Glu Trp
            1090                1095                1100
Arg Lys Glu Ile Val Asn Gly Ser Arg Ser Phe Phe Gly Leu Lys Gly
1105                1110                1115                1120
Leu Met Pro Gly Thr Ala Tyr Lys Val Arg Val Gly Ala Val Gly Asp
                    1125                1130                1135
Ser Gly Phe Val Ser Ser Glu Asp Val Phe Glu Thr Gly Pro Ala Met
                    1140                1145                1150
Ala Ser Arg Gln Val Asp Ile Ala Thr Gln Gly Trp Phe Ile Gly Leu
            1155                1160                1165
Met Cys Ala Val Ala Leu Leu Ile Leu Ile Leu Leu Ile Val Cys Phe
            1170                1175                1180
Ile Arg Arg Asn Lys Gly Gly Lys Tyr Pro Val Lys Glu Lys Glu Asp
1185                1190                1195                1200
Ala His Ala Asp Pro Glu Ile Gln Pro Met Lys Glu Asp Asp Gly Thr
            1205                1210                1215
```

-continued

```
Phe Gly Glu Tyr Ser Asp Ala Glu Asp His Lys Pro Leu Lys Lys Gly
            1220                1225                1230
Ser Arg Thr Pro Ser Asp Arg Thr Val Lys Lys Glu Asp Ser Asp Asp
        1235                1240                1245
Ser Leu Val Asp Tyr Gly Glu Gly Val Asn Gly Gln Phe Asn Glu Asp
    1250                1255                1260
Gly Ser Phe Ile Gly Gln Tyr Ser Gly Lys Lys Glu Lys Glu Pro Ala
1265                1270                1275                1280
Glu Gly Asn Glu Ser Ser Glu Ala Pro Ser Pro Val Asn Ala Met Asn
                1285                1290                1295
Ser Phe Val

<210> SEQ ID NO 3
<211> LENGTH: 38
<212> TYPE: DNA
<213> ORGANISM: Homo sapiens

<400> SEQUENCE: 3
tctcatacta tgaacatatg ggtagagagt atattttc                              38

<210> SEQ ID NO 4
<211> LENGTH: 123
<212> TYPE: DNA
<213> ORGANISM: Rattus norvegicus

<400> SEQUENCE: 4
tctcatacta tggacatatg ggtagaaaga atgttttctg cggtatatga gtattataag      60
aacagagcaa gaacataact cagtcagtca gatgatacgt taatatgaac tggggtgaaa     120
agg                                                                   123

<210> SEQ ID NO 5
<211> LENGTH: 176
<212> TYPE: DNA
<213> ORGANISM: Artificial Sequence
<220> FEATURE:
<223> OTHER INFORMATION: Description of Artificial Sequence: clone D4-1

<400> SEQUENCE: 5
tctcatacta tgaacatatg ggtagagagt atattttctg ctgtatgtta gtattatgag      60
aatagttaca gcaaaaacat aactcagtca agtatatgt taatatgaac tggaatgcaa      120
aagtgcatac tttttcattc aaaatgggta ttcttgattt cctaaaaaaa aaaaaa         176

<210> SEQ ID NO 6
<211> LENGTH: 38
<212> TYPE: DNA
<213> ORGANISM: Artificial Sequence
<220> FEATURE:
<223> OTHER INFORMATION: Description of Artificial Sequence: primer

<400> SEQUENCE: 6
tagatacaac tagtcaatgc ctctaatgaa tatggata                              38

<210> SEQ ID NO 7
<211> LENGTH: 38
<212> TYPE: DNA
<213> ORGANISM: Artificial Sequence
<220> FEATURE:
<223> OTHER INFORMATION: Description of Artificial Sequence: primer

<400> SEQUENCE: 7
```
agatagatcc gcggaatagt aaatccgata gccttgta                                 38

<210> SEQ ID NO 8
<211> LENGTH: 15
<212> TYPE: DNA
<213> ORGANISM: Artificial Sequence
<220> FEATURE:
<223> OTHER INFORMATION: Description of Artificial Sequence: primer
<220> FEATURE:
<221> NAME/KEY: CDS
<222> LOCATION: (1)
<223> OTHER INFORMATION: n=a, c, g, or t

<400> SEQUENCE: 8
ngctgctctc atact                                                          15

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 9
aacatatggg tagagagtat attt                                                24

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 10
ctttgcattc cagttcatat taa                                                 23

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 11
tgtggtgaca gatcacggct                                                     20

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 12
cagctcaaac ctgtgatttc c                                                   21

<210> SEQ ID NO 13
<211> LENGTH: 60
<212> TYPE: DNA
<213> ORGANISM: Artificial Sequence
<220> FEATURE:
<223> OTHER INFORMATION: Description of Artificial Sequence: primer

<400> SEQUENCE: 13
aataggtatt ggtgaattta aagactcact ctccataaat gctacgaata ttaaacactt         60

```
<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 14
cggagcaata tgaaatgatc t                                              21

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 15
gcaaatacag ctcctattg                                                 19

<210> SEQ ID NO 16
<211> LENGTH: 43
<212> TYPE: DNA
<213> ORGANISM: Artificial Sequence
<220> FEATURE:
<223> OTHER INFORMATION: Description of Artificial Sequence: primer

<400> SEQUENCE: 16
gctgtatgtt agtattatga gaatagttac agcaaaaaca taa                      43

<210> SEQ ID NO 17
<211> LENGTH: 40
<212> TYPE: DNA
<213> ORGANISM: Artificial Sequence
<220> FEATURE:
<223> OTHER INFORMATION: Description of Artificial Sequence: primer

<400> SEQUENCE: 17
taggcctgac tggcattgta ttagcaaact catcactaga                          40

<210> SEQ ID NO 18
<211> LENGTH: 37
<212> TYPE: DNA
<213> ORGANISM: Artificial Sequence
<220> FEATURE:
<223> OTHER INFORMATION: Description of Artificial Sequence: primer

<400> SEQUENCE: 18
tagatacaac tagtctaatg cagcttaaaa taatgcc                             37

<210> SEQ ID NO 19
<211> LENGTH: 39
<212> TYPE: DNA
<213> ORGANISM: Artificial Sequence
<220> FEATURE:
<223> OTHER INFORMATION: Description of Artificial Sequence: primer

<400> SEQUENCE: 19
agatagatcc gcggatatcc atattcatta gaggcattg                           39

<210> SEQ ID NO 20
<211> LENGTH: 38
<212> TYPE: DNA
<213> ORGANISM: Artificial Sequence
<220> FEATURE:
<223> OTHER INFORMATION: Description of Artificial Sequence: primer
```

```
<400> SEQUENCE: 20
tagatacaac tagtcaatgc ctctaatgaa tatggata                               38

<210> SEQ ID NO 21
<211> LENGTH: 38
<212> TYPE: DNA
<213> ORGANISM: Artificial Sequence
<220> FEATURE:
<223> OTHER INFORMATION: Description of Artificial Sequence: primer

<400> SEQUENCE: 21
agatagatcc gcggaatagt aaatccgata gccttgta                               38

<210> SEQ ID NO 22
<211> LENGTH: 61
<212> TYPE: DNA
<213> ORGANISM: Homo sapiens
<220> FEATURE:
<223> OTHER INFORMATION: Description of Artificial Sequence: primer

<400> SEQUENCE: 22
aggagttaag atgctaatgc agcttaaaat aatgccgaaa agaagcgct tatctgcggg        60 c                                                                      61

<210> SEQ ID NO 23
<211> LENGTH: 19
<212> TYPE: DNA
<213> ORGANISM: Homo sapiens

<400> SEQUENCE: 23
cattagcatc ttaactcct                                                   19

<210> SEQ ID NO 24
<211> LENGTH: 21
<212> TYPE: DNA
<213> ORGANISM: Homo sapiens

<400> SEQUENCE: 24
tcggcattat tttaagctgc a                                                21

<210> SEQ ID NO 25
<211> LENGTH: 17
<212> TYPE: DNA
<213> ORGANISM: Homo sapiens

<400> SEQUENCE: 25
gcagataagc gcttctt                                                     17

<210> SEQ ID NO 26
<211> LENGTH: 20
<212> TYPE: DNA
<213> ORGANISM: Homo sapiens

<400> SEQUENCE: 26
actagagata cagatcatat                                                  20

<210> SEQ ID NO 27
<211> LENGTH: 20
<212> TYPE: DNA
<213> ORGANISM: Homo sapiens

<400> SEQUENCE: 27
catatacgat cgatcgatgc                                                  20
```

<210> SEQ ID NO 28
<211> LENGTH: 20
<212> TYPE: DNA
<213> ORGANISM: Homo sapiens

<400> SEQUENCE: 28
gatagtgctg atcgatgcta                                              20

<210> SEQ ID NO 29
<211> LENGTH: 48
<212> TYPE: DNA
<213> ORGANISM: Artificial Sequence
<220> FEATURE:
<223> OTHER INFORMATION: Description of Artificial Sequence: primer

<400> SEQUENCE: 29
catacgaatt ctagatacaa ctagtctaat gcagcttaaa ataatgcc               48

<210> SEQ ID NO 30
<211> LENGTH: 50
<212> TYPE: DNA
<213> ORGANISM: Artificial Sequence
<220> FEATURE:
<223> OTHER INFORMATION: Description of Artificial Sequence: primer

<400> SEQUENCE: 30
agatagatcc gcggatatcc atattcatta gaggcattgg gatcccatac             50

<210> SEQ ID NO 31
<211> LENGTH: 1371
<212> TYPE: DNA
<213> ORGANISM: Homo sapiens

<400> SEQUENCE: 31
atgccgaaaa agaagcgctt atctgcgggc agagtgcccc tgattctctt cctgtgccag    60
atgattagtg cactggaagt acctcttgat ccaaaacttc ttgaagactt ggtacagcct   120
ccaaccatca cccaacagtc tccaaaagat tacattattg ccctcgggga gaatattgta   180
atccagtgtg aagccaaagg gaaaccgccc caagcttttt cctggacccg taatgggact   240
cattttgaca tcgataaaga ccctctggtc accatgaagc ctggcacagg aacgctcata   300
attaacatca tgagcgaagg gaaagctgag acctatgaag gagtctatca gtgtacagca   360
aggaacgaac gcggagctgc agtttctaat aacattgttg tccgcccatc cagatcacca   420
ttgtggacca agaaaaaact tgaaccaatc acacttcaaa gtggtcagtc tttagtactt   480
ccctgcagac ccccaattgg attaccacca cctataatat tttggatgga taattccttt   540
caaagacttc cacaaagtga gagagtttct caaggtttga atggggacct ttattttttcc   600 aatgtcctcc cagaggacac ccgcgaagac tatatctgtt atgctagatt taatcatact   660
caaaccatac agcagaagca acctatttct gtgaaggtga tttcagtgga tgaattgaat   720
gacactatag ctgctaattt gagtgacact gagtttttatg gtgctaaatc aagtagagag   780
aggccaccaa cattttttaac tccagaaggc aatgcaagta caaagagga attaagagga   840 aatgtgcttt cactggagtg cattgcagaa ggactgccta cccccaattat ttactgggca   900 aaggaagatg gaatgctacc caaaaacagg acagtttata gaactttga gaaaccttg   960 cagatcattc atgtttcaga agcagactct ggaaattacc aatgtatagc aaaaaatgca  1020
ttaggagcca tccaccatac catttctgtt agagttaaag cggctccata ctggatcaca  1080

-continued

```
gcccctcaaa atcttgtgct gtccccagga gaggatggga ccttgatctg cagagctaat    1140
ggcaacccca aacccagaat tagctggtta acaaatggag tcccaataga aattgccct     1200
gatgacccca gcagaaaaat agatggcgat accattattt tttcaaatgt tcaagaaaga    1260
tcaagtgcag tatatcagtg caatgcctct aatgaatatg gatatttact ggcaaacgca    1320
tttgtaaatg tgctggctga gccaccacga atcctcacac ctgcaaacac a             1371
```

<210> SEQ ID NO 32
<211> LENGTH: 1371
<212> TYPE: DNA
<213> ORGANISM: Rattus norvegicus

<400> SEQUENCE: 32

```
atgccgaaga agaagccctt gtctgcaggc agagcgcccc tgtttctctt cctgtgccag     60
atgatcagcg ctctggatgt tcctcttgat ccaaagctcc ttgatgactt ggtacagcct    120
ccaactatca ctcaacagtc accaaaagac tacatcattg acccacggga gaatattgta    180
atccaatgtg aggccaaagg gaaacctcct ccaagctttt cctggactcg taacggaaca    240
cattttgaca tagacaaaga ccctctggtc actatgaagc ctggctcagg aacccttgtc    300
atcaacatca tgagtgaagg aaaggcggag acctatgaag gggtttacca gtgcactgca    360
aggaatgagc gcggagctgc tgtctccaat aacattgttg tccgcccctc taggtcaccc    420
ttgtggacca aggaaagact tgaaccaata atcctccgaa gtggtcagtc actagtacta    480
ccatgtaggc ctccaattgg attaccaccg gccataatat tttggatgga taactccttt    540
caaagactgc cacagagtga gcgggtttcc caaggactga atggagacct ttacttctcc    600
aatgtcctcc cagaggacac ccgtgaggac tacatctgct atgccagatt taatcacact    660
caaacaattc aacagaaaca acctatttct ctgaaggtga tttcagtgga tgaattgaat    720
gacactatag ctgctaattt gagtgacact gagttttatg gtgctaaatc tagtaaagag    780
aggccaccaa catttctaac tccagagggc aatgaaagtc acaaggaaga attaagagga    840
aacgtgcttt ccctggagtg cattgcagaa ggcctaccta ctccagttat ttactggatc    900
aaggaagatg gaacgcttcc tgtcaaccgg acgttttatc ggaactttaa gaaaaccttg    960
cagatcattc atgtctctga agcagactct ggaaattatc agtgcatagc aaaaaacgca   1020
ttgggagccg tccatcatac catttctgtc acagttaaag cggctcccta ctggattgtt   1080
gcacctcaca acctcgtgct ttccccaggg gagaatggga ccctcatctg cagagctaac   1140
ggcaacccaa aacccagaat tagctggtta acaaatggag tcccagtaga aattgctctc   1200
gatgacccca gccgaaaaat cgatggtgat accattatgt tttcaaatgt tcaagaaagc   1260
tcaagtgcgg tttatcagtg caatgcctct aacaaatatg gatatttact agcaaatgca   1320
tttgtaaatg tgctcgctga accacctcgg attcttacct cagcaaacac a             1371
```